US010809259B2

(12) United States Patent
Isailovic et al.

(10) Patent No.: US 10,809,259 B2
(45) Date of Patent: *Oct. 20, 2020

(54) PROTOCOL FOR PRECONCENTRATION AND QUANTIFICATION OF MICROCYSTINS USING LC-MS

(71) Applicant: The University of Toledo, Toledo, OH (US)

(72) Inventors: Dragan Isailovic, Toledo, OH (US); Dilrukshika Palagama, Toledo, OH (US); David Baliu-Rodriguez, Toledo, OH (US); Bruce S. Levison, Toledo, OH (US); David J. Kennedy, Toledo, OH (US); Steven T. Haller, Toledo, OH (US); Kenneth Hensley, Toledo, OH (US)

(73) Assignee: The University of Toledo, Toledo, OH (US)

( * ) Notice: Subject to any disclaimer, the term of this patent is extended or adjusted under 35 U.S.C. 154(b) by 78 days.

This patent is subject to a terminal disclaimer.

(21) Appl. No.: 16/033,496

(22) Filed: Jul. 12, 2018

(65) Prior Publication Data
US 2018/0321237 A1 Nov. 8, 2018

Related U.S. Application Data

(63) Continuation-in-part of application No. 15/331,240, filed on Oct. 21, 2016, now Pat. No. 10,436,794.

(51) Int. Cl.
*G01N 1/40* (2006.01)
*G01N 33/569* (2006.01)
*G01N 33/68* (2006.01)

(52) U.S. Cl.
CPC ....... *G01N 33/56911* (2013.01); *G01N 1/405* (2013.01); *G01N 33/6848* (2013.01); *G01N 2001/4027* (2013.01); *G01N 2333/195* (2013.01)

(58) Field of Classification Search
None
See application file for complete search history.

(56) References Cited

U.S. PATENT DOCUMENTS

| 10,436,794 B1* | 10/2019 | Isailovic | G01N 30/7233 |
| 2003/0178370 A1* | 9/2003 | Fisk | B01L 3/50255 |
| | | | 210/198.2 |
| 2013/0334415 A1* | 12/2013 | Sugawara | H01J 49/0009 |
| | | | 250/288 |

OTHER PUBLICATIONS

Miller et al., "Evidence for a Novel Marine Harmful Algal Bloom: Cyanotoxin (Microcystin) Transfer from Land to Sea Otters", PloS One 5(9): e12576.doI:10.1371/journal.pone.0012576 (Year: 2010).*
Beck et al., "Fast and Accurate Determination of Algal Toxins in Water Using On-line Preconcentration and UHPLC-HRAM-MS" Oct. 6, 2014, The Column, vol. 10, Issue 18, pp. 2-10 (Year: 2014).*
Spoof et al., "Screening for cyanobacterial hepatotoxins, microcystins and nodularin in environmental water samples by reversed-phase liquid chromatography—electrospray ionisation mass spectrometry" (2003) Journal of Chromatography A, 1020, pp. 105-119 (Year: 2003).*
Howard et al., "Adduct simplification in the analysis of cyanobacterial toxins by matrix-assisted laser desorption/ionization mass spectrometry" Rapid Communications in Mass Spectrometry 21:699-706 (Year: 2007).*

* cited by examiner

*Primary Examiner* — Paul S Hyun
(74) *Attorney, Agent, or Firm* — MacMillan, Sobansky & Todd, LLC

(57) ABSTRACT

Methods for detecting and quantifying one or more microcystin compounds in a sample are described. The methods may include a preconcentration step, and generally utilize an LC-MS or LC-MS/MS analysis with an Orbitrap Fusion mass spectrometer or a QqQ mass spectrometer. The methods provide excellent recoveries and limits of quantification of microcystins.

Figure 1:
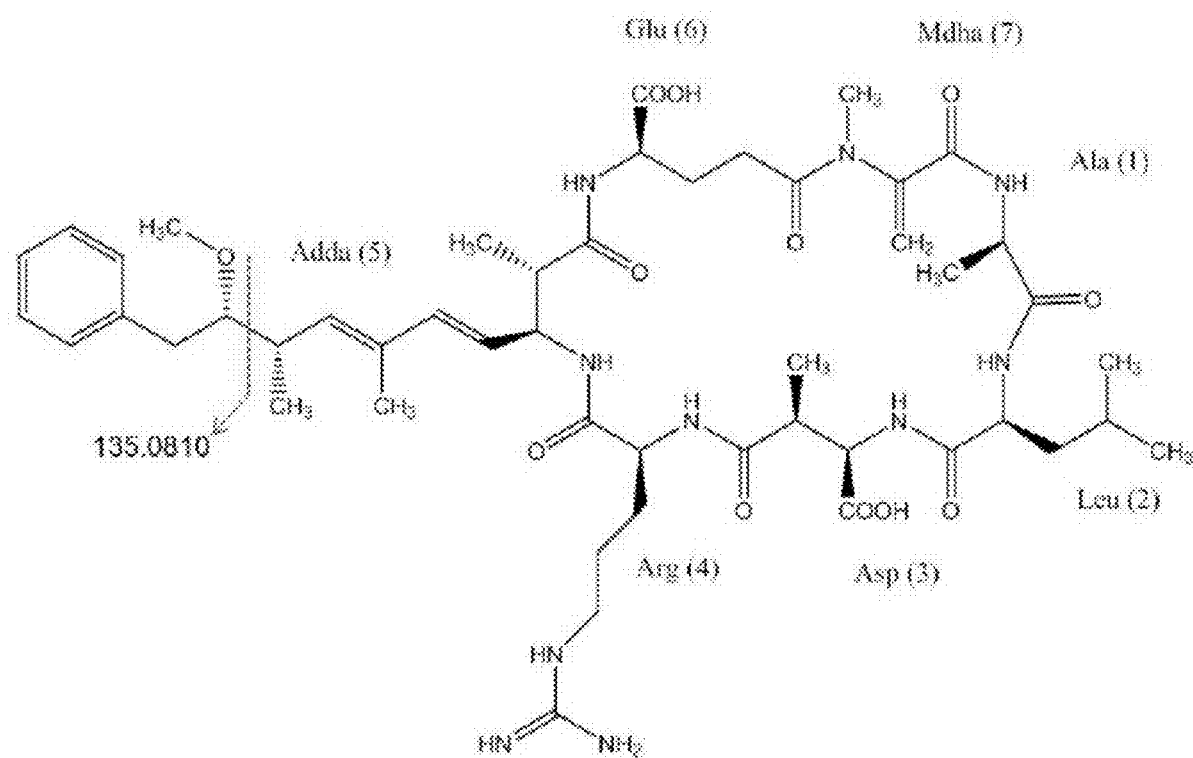

17 Claims, 64 Drawing Sheets
(42 of 64 Drawing Sheet(s) Filed in Color)

| Time | Module | Event | Parameter |
|---|---|---|---|
| 0.01 | Controller | Start | |
| 2.00 | Pumps | Pump B Conc. | 60 |
| 7.00 | Pumps | Pump B Conc. | 70 |
| 12.00 | Pumps | Pump B Conc. | 90 |
| 14.00 | Pumps | Pump B Conc. | 10 |
| 18.00 | Controller | Stop | |

FIG. 13A – Table 4

| Concentration | | LR | LA | LW | RR | YR | LF |
|---|---|---|---|---|---|---|---|
| Individual | | | | | | | |
| 500 ppq | Recovery | 99.98 | 98.07 | 98.23 | 99.05 | 98.17 | 99.12 |
| | RSD | 2.13 | 3.25 | 1.24 | 3.87 | 2.65 | 1.98 |
| 25 ppt | Recovery | 98.39 | 99.25 | 98.65 | 99.56 | 98.27 | 99.45 |
| | RSD | 2.89 | 1.26 | 2.56 | 3.48 | 2.98 | 2.15 |
| 600 ppt | Recovery | 98.99 | 99.62 | 99.02 | 99.14 | 98.41 | 98.06 |
| | RSD | 2.09 | 3.14 | 2.56 | 2.89 | 2.47 | 4.51 |
| As a Mixture | | | | | | | |
| 500 ppq | Recovery | 98.15 | 98.46 | 98.21 | 98.99 | 98.16 | 99.45 |
| | RSD | 3.45 | 3.56 | 4.15 | 2.99 | 2.98 | 2.48 |
| 200 ppt | Recovery | 98.99 | 99.74 | 99.05 | 98.26 | 98.45 | 98.05 |
| | RSD | 2.78 | 4.69 | 3.87 | 3.85 | 3.41 | 3.96 |
| 600 ppt | Recovery | 98.26 | 98.56 | 98.47 | 98.26 | 99.15 | 98.58 |
| | RSD | 3.89 | 3.48 | 4.63 | 4.12 | 3.79 | 3.02 |

FIG. 16 – Table 5

| MS method | Data acquisition mode | SPE percent recover (%) | Linear range (μg/L) | R² | LOD (μg/L) | LOQ (μg/L) |
|---|---|---|---|---|---|---|
| QqQ-MS/MS | MRM | - | 9.94-994.55 | 0.9952 | 7.96 | 24.86 |
| LIQ Orbitrap-MS/MS | SRM | - | 497.27-945.49 | 0.9763 | 149.18 | 517.16 |
| Orbitrap-full scan | Full scan | 113.7 | 0.1-1.0 | 0.9991 | 0.009 | 0.03 |
| QqQ-MS/MS | MRM | 88.0-98.0 | 0.5-10.0 | 0.999 | 0.11 | 0.029 |
| QqQ-MS/MS | MRM | 95.0-105.0 | 0.1 - 1 | 0.9997 | 0.012 | 0.04 |
| Ion trap-MS/MS[a] | MRM | 73.5-82.7 | 0.82-200 | 0.9992 | 4.9 ng/L | 15.8 ng/L |
| Q-ToF-MS/MS | DDA[b] | 80.1-85.0 | 0.1-50.0 | 0.994 | 0.01 | 0.1 |
| Ion trap-MS/MS | SRM | 72.6-96.5 | 10-100 | - | 0.1 | 0.5 |
| QqQ-MS/MS | SRM | 97-113 | 0.025-2.50 | 0.99 | 0.002 | 0.005 |
| LIQ-MS/MS | Full scan | - | 0.05-50 | 0.9994 | 0.025 | 0.05 |
| QqQ-MS/MS | MRM | - | 0.5-70 | 0.996 | 0.1 | 0.5 |
| QqQ-MS/MS | MRM | - | 0.2-20 | 0.9997 | 0.04 | 0.1 |
| QqQ-MS/MS | MRM | 79.8-104.0 | 1-750 | 0.99 | 0.002 | 0.006 |
| QqQ-MS/MS | MRM | - | 1-1000 | 0.9949 | 1.5 | 4.5 |
| Q-MS | | 89-104 | 200-2000 ng/L | 0.997 | 2 ng/L | - |
| LCQ-Ion trap | Full scan | - | 0.1-10 ng/L | 0.9992 | 2.6 ng/L | - |
| Orbitrap-MS | SIM | - | 0.025-10 | 0.9999 | ~0.010 | 0.025 |
| Orbitrap-MS | SIM | 97.55-99.85 | 0.50-35 ng/L | 0.9987 | ~0.30 ng/L | 0.50 ng/L |
| Orbitrap-MS/MS | SIM | - | 0.20-10 | 0.9999 | ~0.1 | 0.2 |
| Orbitrap-MS/MS | SIM | - | 7-35 ng/L | 0.9974 | ~5 ng/L | 7 ng/L |

[a] Negative ion mode
[b] Data dependent analysis
All units are converted in to μg/L

FIG. 20 – Table 6

| MC Variant | X | Y |
|---|---|---|
| MC-LR | Leu | Arg |
| MC-YR | Tyr | Arg |
| MC-RR | Arg | Arg |
| MC-LF | Leu | Phe |
| MC-LW | Leu | Trp |
| MC-LA | Leu | Ala |

PROTOCOL FOR PRECONCENTRATION AND QUANTIFICATION OF MICROCYSTINS USING LC-MS

RELATED APPLICATIONS

This is a continuation-in-part application of U.S. application Ser. No. 15/331,240, filed under 35 U.S.C. § 111(a) on Oct. 21, 2016, the entire disclosure of which is expressly incorporated herein by reference for all purposes.

STATEMENT REGARDING FEDERALLY SPONSORED RESEARCH

This invention was made with no government support. The government has no rights in this invention.

BACKGROUND OF THE INVENTION

Cyanobacteria are prokaryotic organisms that typically produce toxic metabolites called cyanotoxins. The most commonly encountered toxic compounds that are released by cyanobacteria are microcystins (MCs). MCs are a group of cyclic heptapeptides which have common amino acid sequences with a recurring motif of a 3-amino-9-methoxy-2,6,8-trimethyl-10-phenyldeca-4,6-dienoic acid (ADDA) group present. Over 200 variants of MCs, such as microcystin-LR (MC-LR), have been identified from different cyanobacterial species. MC-LR is the most common cyanobacterial hepatotoxin, which is often released in water during harmful cyanobacterial blooms.

MCs cause concerns due to both their acute toxicity and chronic effects on humans and wildlife. Due to these concerns, the U.S. Environmental Protection Agency (EPA) advises that the total concentration of MCs in drinking water should be ≤0.3 μg/L for children, and the state of Minnesota advises an even lower concentration (≤0.1 μg/L) of MC-LR in water. Similarly, the World Health Organization has set a provisional guideline limit for the maximum MC-LR concentration in drinking water of 1 ppb. As a result, robust and sensitive techniques are needed to detect sub-ppb concentrations of MCs in water samples.

MC-LR is one of the most hepatotoxic microcystins released by cyanobacteria. Besides ADDA, the MC-LR structure (FIG. 1) includes a leucine (L) at position 2 and an arginine (R) at position 4 (amino acids in these positions vary from one MC variant to another). In order to monitor the MC-LR concentration in water samples, robust techniques that can detect low concentration of MCs are needed. Determination of MCs is challenging because of a lack of MC standards, inconsistent recoveries during sample preparation, and matrix interferences. Several analytical techniques have been used to detect, identify, and quantify MCs. For example, enzyme-linked immunosorbent assay (ELISA) and protein phosphatase inhibition assay have been used to quantify these toxins. These high-throughput methods typically report total concentration of multiple MC variants, and are therefore limited for the identification and quantification of specific MC variants.

Separations of MCs by HPLC, as well as their detection and quantification, have been demonstrated using UV and fluorescence detectors. LC-MS has been used for the analysis of MCs in water samples since it can provide reliable detection, differentiation, and quantitation of MC congeners. LC-MS and MS/MS detection and quantification of MCs have been reported using several different mass analyzers, such as quadrupole (Q), triple quadrupole (QqQ), ion trap, linear ion trap (LIT), time-of-flight (TOF), and Q-TOF. Most LC-MS/MS quantification methods have been performed using multiple reaction monitoring (MRM) mode of QqQ mass spectrometers.

While LC-MS and LC-MS/MS methods enable highly selective and sensitive quantitation of individual MC variants, they commonly need to utilize some form of preconcentration before the analysis. The preconcentration improves limits of detection (LODs) and limits of quantification (LOQs) of MCs, but it may lead to incomplete or irreproducible recovery of MCs before the LC-MS analysis. Low LOQs (50 ng/L) of MC-LR, MC-YR, and MC-RR have been achieved without preconcentration of the samples before the LC-MS/MS analysis using a LIT MS in full scan mode. Considering the importance of detection and quantification of toxins in drinking water, it is important to continue developing LC-MS and LC-MS/MS methods that can employ modern HPLCs and mass spectrometers for quantification of MCs. There is a need in the art for new and improved methods and systems for the detection and quantification of MCs, such as MC-LR.

SUMMARY OF THE INVENTION

Provided is an improved method of detecting and quantifying a microcystin compound in a sample, the method comprising preconcentrating a sample containing a microcystin compound at a first concentration through a solid-phase extraction (SPE) to obtain a preconcentrated sample containing the microcystin at a second concentration, where the second concentration is higher than the first concentration, and conducting a quantitative analysis on the preconcentrated sample to quantify the amount of microcystin in the preconcentrated sample, where the quantitative analysis comprises a liquid chromatography step and a mass spectrometry step using an Orbitrap Fusion mass spectrometer, and using a calibration curve to determine the concentration of the microcystin compound in the sample.

In certain embodiments, the sample contains multiple microcystin compounds, and the liquid chromatography step separates the multiple microcystin compounds. In particular embodiments, the liquid chromatography step comprises gradient high-performance liquid chromatography.

In certain embodiments, the preconcentrating comprises conditioning a solid-phase extraction cartridge with methanol containing formic acid (such as 90% methanol containing 0.1% formic acid), equilibrating the cartridge in formic acid (such as 0.1% formic acid), loading the sample in the conditioned solid-phase extraction cartridge, and eluting the loaded sample with acetonitrile and formic acid (such as 90% acetonitrile and 0.1% formic acid). In particular embodiments, the preconcentrating further comprises desalting the loaded sample with formic acid prior to eluting the loaded sample with acetonitrile and formic acid (such as 90% acetonitrile and 0.1% formic acid).

In certain embodiments, the method is capable of quantifying the microcystin compound at a concentration in the sample as low as about 500 ppq. In certain embodiments, the microcystin compound is selected from the group consisting of MC-LR, MC-LA, MC-LF, MC-LW, MC-YR, and MC-RR.

Further provided is a method for detecting and quantifying a microcystin compound in a sample, the method comprising separating a microcystin species in a sample containing a plurality of microcystin species through high-performance liquid chromatograph (HPLC), where the HPLC comprises a gradient mobile phase composition created by acetonitrile and 0.1% formic acid, to produce separated microcystin samples, and conducting mass spectrometry on at least one of the separated microcystin samples to quantify the amount of a microcystin species in the at least one separated microcystin sample, where the mass spectrometry uses an Orbitrap Fusion mass spectrometer, and using a calibration curve to determine the concentration of the at least one microcystin species in the sample. In certain embodiments, the plurality of microcystin species includes two or more of MC-LR, MC-LA, MC-LF, MC-LW, MC-YR, and MC-RR.

In certain embodiments, the method further comprises a preconcentrating step prior to the separating, where the preconcentrating step comprises preconcentrating the sample containing the plurality of microcystin species at a first concentration through a solid-phase extraction to obtain a preconcentrated sample containing the plurality of microcystin species at a second concentration, where the second concentration is higher than the first concentration. In particular embodiments, the preconcentrating step comprises conditioning a solid-phase extraction cartridge with methanol containing formic acid (such as 90% methanol containing 0.1% formic acid), equilibrating the sample in formic acid (such as 0.1% formic acid), loading the sample in the conditioned solid-phase extraction cartridge, optionally desalting the loaded sample with formic acid (such as 0.1% formic acid), and eluting the loaded sample with acetonitrile and formic acid (such as 90% acetonitrile containing 0.1% formic acid).

Further provided is a method of preconcentrating microcystin in a sample, the method comprising conditioning a solid-phase extraction cartridge with methanol containing formic acid (such as 90% methanol containing 0.1% formic acid), loading a sample containing a microcystin at a first concentration onto the solid-phase extraction cartridge, eluting the sample with acetonitrile containing formic acid (such as 90% acetonitrile containing 0.1% formic acid), and collecting the eluted sample, evaporating solvent from the eluted sample to obtain an evaporated sample, and redissolving the evaporated sample in a solvent (such as 90% methanol containing 0.1% formic acid) to obtain a preconcentrated sample, where the preconcentrated sample contains microcystin at a second concentration, the second concentration being greater than the first concentration. In certain embodiments, the method further comprises equilibrating the SPE cartridge with 0.1% formic acid. In certain embodiments, the method further comprises a washing step. In certain embodiments, the method further comprises subjecting the preconcentrated sample to LC-MS analysis. In certain embodiments, the SPE cartridge is a C18 cartridge. In certain embodiments, the sample comprises a plurality of microcystin species. In particular embodiments, the plurality of microcystin species includes two or more of MC-LR, MC-LA, MC-LF, MC-LW, MC-YR, and MC-RR.

Further provided is a method for separating a plurality of microcystin compounds in a mixture, the method comprising introducing a solvent containing a sample mixture into a column filled with a solid adsorbent material, where the sample mixture comprises a plurality of microcystin compounds, using a first pump to pass a first mobile phase through the column, and using a second pump to pass a second mobile phase through the column, thereby creating a gradient mobile phase in the column to separate the plurality of microcystin compounds in the column, and allowing one or more separated microcystin compounds to elute out of the column. In certain embodiments, the first mobile phase comprises acetonitrile and the second mobile phase comprises 0.1% formic acid. In other embodiments, the first mobile phase comprises 0.1% formic acid with 20 mM ammonium formate, and the second mobile phase comprises methanol with 0.1% formic acid. In certain embodiments, the gradient mobile phase is created over 30 minutes by a solvent profile of 10% methanol with 0.1% formic acid for minutes 0-2, 80% methanol with 0.1% formic acid for minutes 2-16, 90% methanol with 0.1% formic acid for minutes 16-22, and 10% methanol with 0.1% formic acid for minutes 22-30. In certain embodiments, the gradient mobile phase is created over 18 minutes by a solvent profile of 10% acetonitrile for minutes 0-2, 60% acetonitrile for minutes 2-7, 70% acetonitrile for minutes 7-12, 90% acetonitrile for minutes 12-14, and 10% acetonitrile for minutes 14-18.

Further provided is a method for detecting and quantifying a microcystin compound in a sample, the method comprising purifying a sample containing a microcystin compound in plasma, serum, or urine; conducting a quantitative analysis on the purified sample to quantify the amount of microcystin in the purified sample, wherein the quantitative analysis comprises a liquid chromatography step and a mass spectrometry step; and using a calibration curve to determine the concentration of the microcystin compound in the sample. In certain embodiments, the quantitative analysis comprises HPLC-orbitrap-MS. In certain embodiments, the quantitative analysis comprises HPLC-QqQ-MS/MS. In certain embodiments, the method comprises preconcentrating the sample, wherein the purified sample comprises the microcystin at a concentration higher than the concentration of the microcystin in the original sample.

In certain embodiments, the sample contains a microcystin compound in plasma or serum, and the method further comprises adding $ZnSO_4$ to the sample. In particular embodiments, the $ZnSO_4$ is added at a concentration of about 100 mM. In particular embodiments, the method further comprises acidifying the sample with formic acid. In particular embodiments, the method further comprises subjecting the sample to SPE and analyzing the sample by HPLC-orbitrap-MS.

In certain embodiments, the sample contains a microcystin compound in plasma or serum, and the purifying comprises eluting the sample with methanol containing formic acid. In certain embodiments, the sample contains a microcystin compound in urine, and the purifying comprises eluting the sample with acetonitrile and formic acid. In certain embodiments, the sample contains multiple microcystin compounds, and the liquid chromatography step separates the multiple microcystin compounds. In particular embodiments, the liquid chromatography step comprises gradient high-performance liquid chromatography.

In certain embodiments, the purifying step is a preconcentrating step, and the purified sample contains the microcystin compound at a higher concentration than the original sample.

In certain embodiments, the method is capable of quantifying the microcystin compound at a concentration in the sample as low as about 500 ppq for MCs in water, as low as about 130 ppt for MCs in urine, or as low as about 250 ppt for MCs in plasma and serum. In certain embodiments, the microcystin compound is selected from the group consisting of MC-LR, MC-LA, MC-LF, MC-LW, MC-YR, and MC-RR.

Further provided is a method of preconcentrating mycrocystin in a sample, the method comprising conditioning a solid-phase extraction (SPE) cartridge with methanol containing formic acid, and equilibrating and washing the cartridge; loading a sample containing a microcystin at a first concentration onto the solid-phase extraction cartridge; eluting the sample with methanol containing formic acid, and collecting the eluted sample; evaporating solvent from the eluted sample to obtain an evaporated sample, and redissolving sample in the solvent to obtain a preconcentrated sample, wherein the preconcentrated sample contains microcystin at a second concentration, the second concentration being greater than the first concentration. In certain embodiments, the method further comprises equilibrating the SPE cartridge with formic acid. In certain embodiments, the method further comprises a washing step. In certain embodiments, the method further comprises subjecting the preconcentrated sample to LC-MS analysis. In certain embodiments, the SPE cartridge is a C18 cartridge. In certain embodiments, the sample comprises a plurality of microcystin species. In certain embodiments, the plurality of microcystin species includes two or more of MC-LR, MC-LA, MC-LF, MC-LW, MC-YR, and MC-RR.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 1: The structure of MC-LR and its most intense fragment ion (m/z ~135.0810), which is characteristic for MCs.

FIGS. 2A-2B: Extracted ion chromatogram (EIC) of singly-charged protonated MC-LR ion (m/z 995.5587) (FIG. 2A), and LC-mass spectrum of 1 μg/L standard solution of MC-LR (FIG. 2B).

FIG. 3: The LC-ESI-MS calibration curve for quantification of MC-LR in concentration range 25 ng/L-10 μg/L. The MC-LR samples were not preconcentrated before LC-MS analyses. Standard deviations are shown as error bars. The inset shows the region of the calibration curve in the concentration range from 0.025-1.0 μg/L.

FIGS. 4A-4B: The EIC (FIG. 4A) and mass spectrum (FIG. 4B) corresponding to LOQ of MC-LR (25 ng/L) determined by LC-MS. The MC-LR sample analyzed was not preconcentrated.

FIGS. 5A-5B: The LC-MS calibration curves for quantification of MC-LR in tap water (FIG. 5A) and river water (FIG. 5B) after purification of MC-LR standards using SPE and preconcentration. Standard deviations (n=3) are shown as error bars. The MC-LR concentration ranges analyzed were 500 pg/L-35 ng/L for tap water and 2 ng/L-35 ng/L for river water.

FIGS. 6A-6B: The EIC of singly-charged protonated MC-LR ion (m/z 995.5580) (FIG. 6A), and LC-mass spectrum of 20 ng/L standard solution of MC-LR obtained after 50× sample preconcentration (FIG. 6B). After preconcentration, the concentration of MC-LR in this solution was ~1 μg/L.

FIGS. 7A-7B: The EIC (FIG. 7A) and mass spectrum (FIG. 7B) corresponding to LOQ of MC-LR (500 pg/L) determined by LC-MS after 50× sample preconcentration. After preconcentration, the concentration of MC-LR in this solution was ~25 ng/L.

FIG. 8: Overlaid EICs of singly-charged MC-RR, MC-LR, and MC-LA ions with m/z values of 1038.57, 995.56, and 910.49, respectively. Each MC was analyzed by LC-ESI-MS individually.

FIGS. 9A-9B: Mass spectra of singly-charged MC-LA (FIG. 9A) and MC-RR (FIG. 9B) ions.

FIGS. 10A-10B: EIC of MC-LR fragment ion with m/z 135.0808 (FIG. 10A) and MS/MS spectrum of MC-LR ion with m/z 995.5587 (FIG. 10B). The concentration of MC-LR standard used to acquire these data was 1 μg/L.

FIG. 11: The LC-ESI-MS/MS calibration curve for quantification of MC-LR in the concentration range of 200 ng/L-10 μg/L. The MC-LR samples were not preconcentrated before LC-MS analyses. Standard deviations are shown as error bars. The inset shows the region of the calibration curve in the concentration range of 0.2-10.0 μg/L.

FIG. 12: The LC-MS/MS calibration curve for quantification of MC-LR after 50× preconcentration and purification of MC-LR standards using SPE. Standard deviations are shown as error bars. The MC-LR concentration range analyzed was 7-35 ng/L.

FIGS. 13A-13B: Table 4, showing the solvent parameters for an HPLC method for separation of MCs (FIG. 13A), and a graph showing the solvent gradient in Table 4 (FIG. 13B).

FIG. 14: Extracted ion chromatograms for a mixture of MCs.

FIGS. 15A-15F: Calibration curves without preconcentration for MC-LR (FIG. 15A), MC-LA (FIG. 15B), MC-YR (FIG. 15C), MC-LW (FIG. 15D), MC-LF (FIG. 15E), and MC-RR (FIG. 15F) in HPLC-grade water. The LOQ ranged from 25 ppt to 1 ppb without preconcentration.

FIG. 16: Table 5, displaying solid-phase extraction recovery data using one SPE cartridge for a mixture containing the MC species MC-LR, MC-LA, MC-LW, MC-RR, MC-YR, and MC-LF in HPLC-grade water.

FIGS. 17A-17F: Calibration curves with preconcentration MC-LR (FIG. 17A), MC-LA (FIG. 17B), MC-YR (FIG. 17C), MC-LW (FIG. 17D), MC-LF (FIG. 17E), and MC-RR (FIG. 17F) in HPLC-grade water. The LOQ ranged from 500 ppq to 20 ppt with preconcentration.

FIG. 18: EICs of doubly-charged MC-RR (top) and singly-charged MC-LR (middle) and MC-LA (bottom) ions with m/z values of 519.79, 995.56, and 910.49, respectively. Each MC was analyzed by LC-ESI-MS individually.

FIGS. 19A-19B: Mass spectra of doubly-charged MC-RR ion (FIG. 19A) and singly-charged MC-LA ion (FIG. 19B).

FIG. 20: Table 6, showing a comparison of LODs and LOQs of MC-LR obtained by different LC-ESI-MS and LC-ESI-MS/MS methods.

FIG. 21: General structure of six common MC variants.

FIGS. 22A-22F: Optimization of the amount of $ZnSO_4$ added and the acidity of the mouse plasma samples for extraction of MC-LR (FIG. 22A), MC-RR (FIG. 22B), MC-LA (FIG. 22C), MC-LF (FIG. 22D), MC-LW (FIG. 22E), and MC-YR (FIG. 22F). Relative abundances of MC ions using EIC chromatograms were compared. Samples were analyzed with HPLC-orbitrap-MS.

FIGS. 23A-23F: Optimization of the equilibration and elution solvents for SPE of MC-LR (FIG. 23A), MC-RR (FIG. 23B), MC-LA (FIG. 23C), MC-LF (FIG. 23D), MC-LW (FIG. 23E), and MC-YR (FIG. 23F) from plasma. Relative abundances of MC ions using EIC chromatograms were compared. Solvent combinations E-1 to E-8 are shown in Table 4 and the samples were analyzed in triplicate with HPLC-orbitrap-MS.

FIG. 24: Internal standard calibration curve for quantification of MC-LR in mouse plasma using peak areas of EIC chromatogram of MC monoisotopic ions obtained with HPLC-orbitrap-MS.

FIG. 25: Concentration of MC-LR in mouse plasma samples, analyzed using HPLC-orbitrap-MS instrument in triplicate runs.

Figure 26:
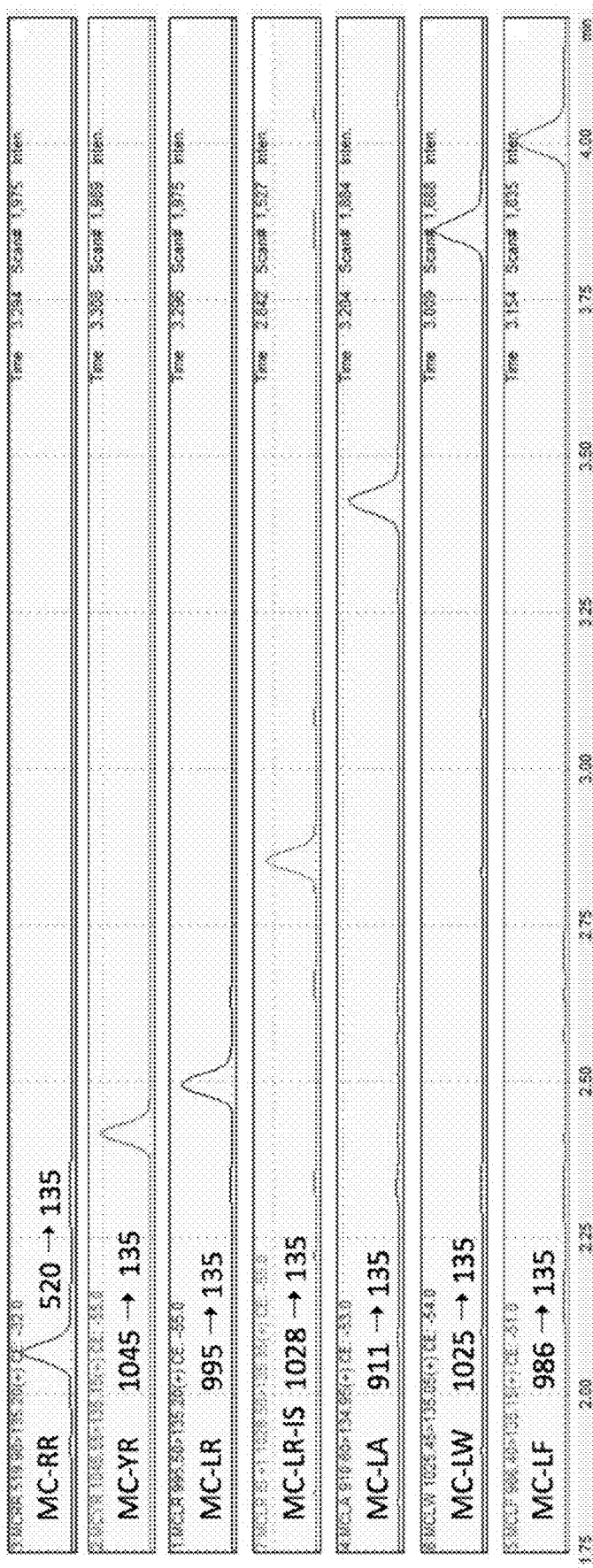

FIG. 26: MRM chromatograms of MC fragment ions (m/z 135) using UHPLC-QqQ-MS/MS. From top to bottom, analytes are MC-RR, MC-YR, MC-LR, MC-IS, MC-LA, MC-LW, and MC-LF.

Figure 27A:
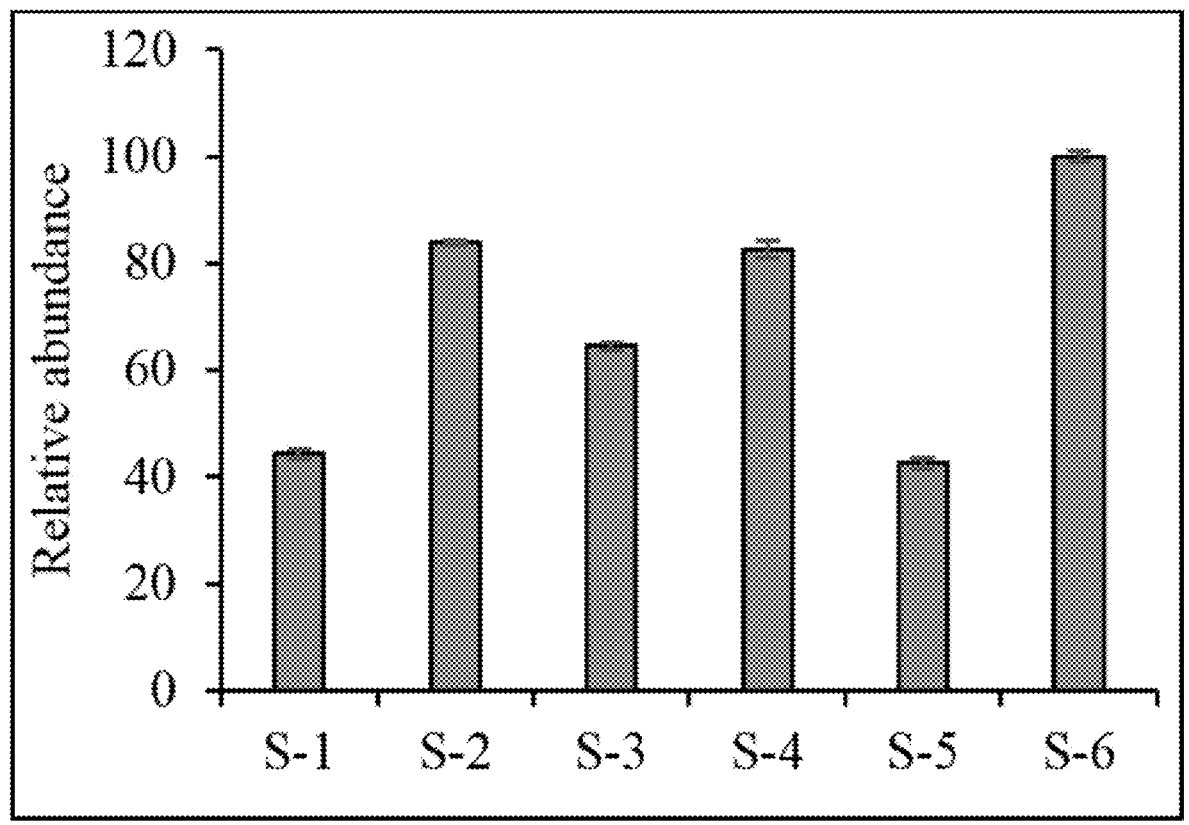
Figure 27B:
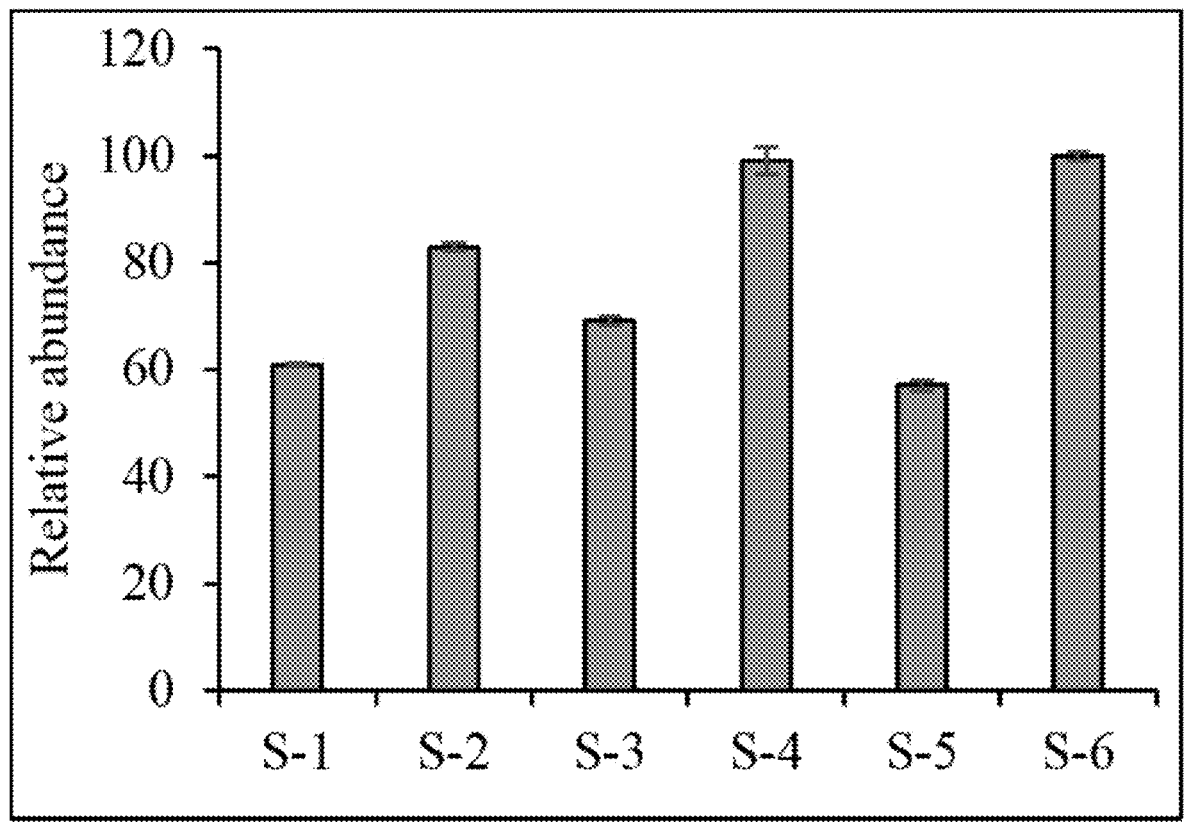
Figure 27C:
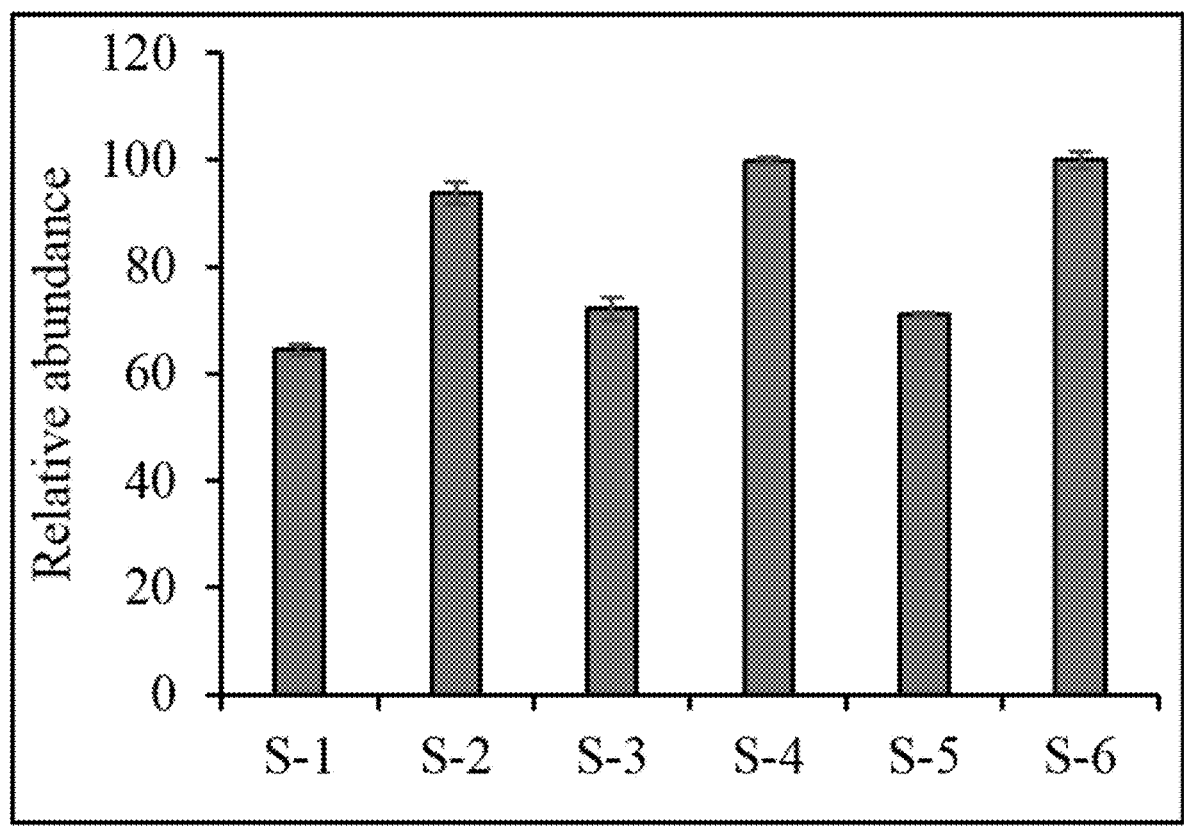
Figure 27D:
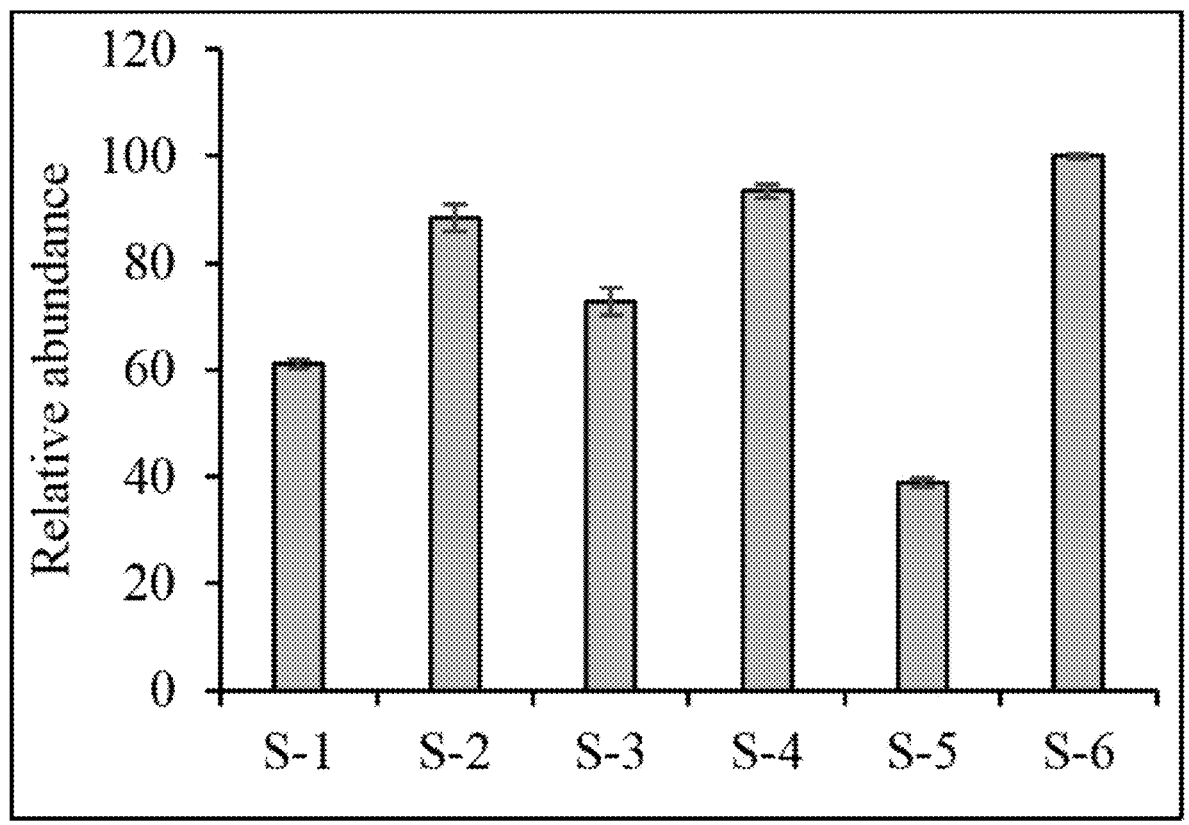
Figure 27E:
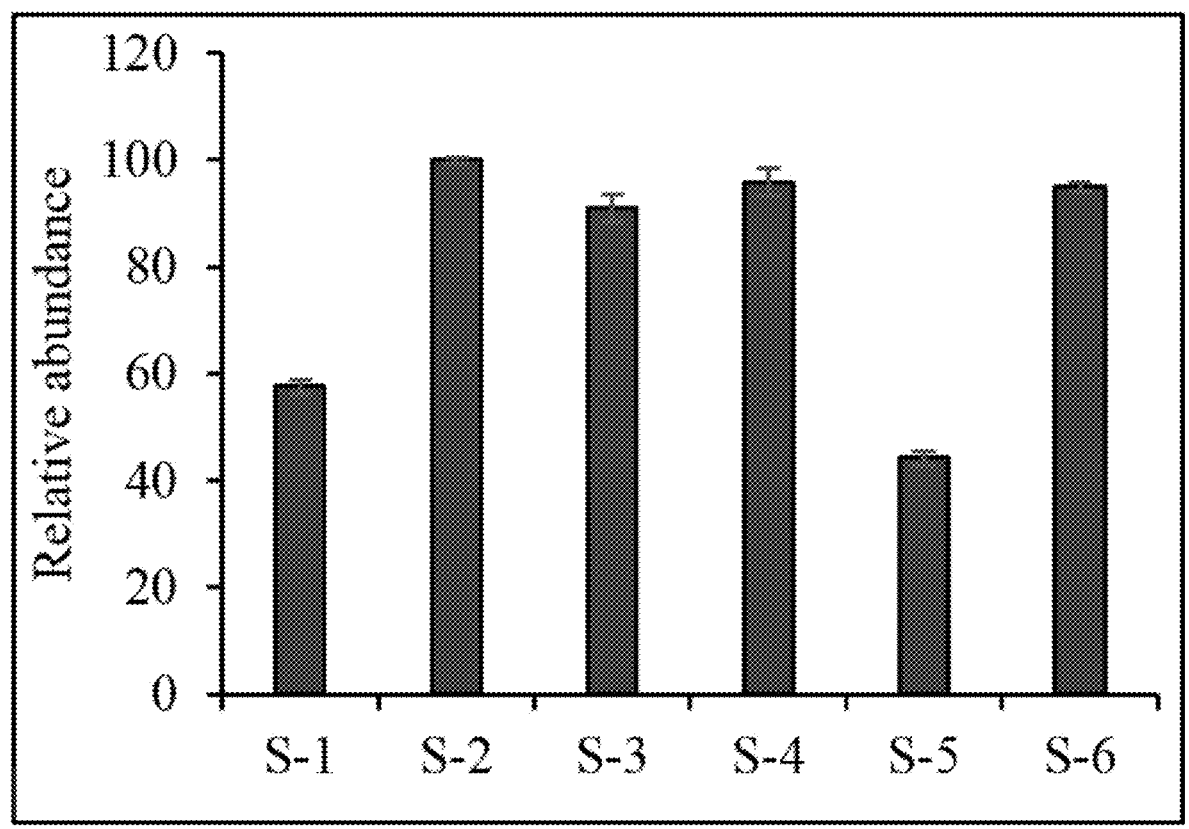
Figure 27F:
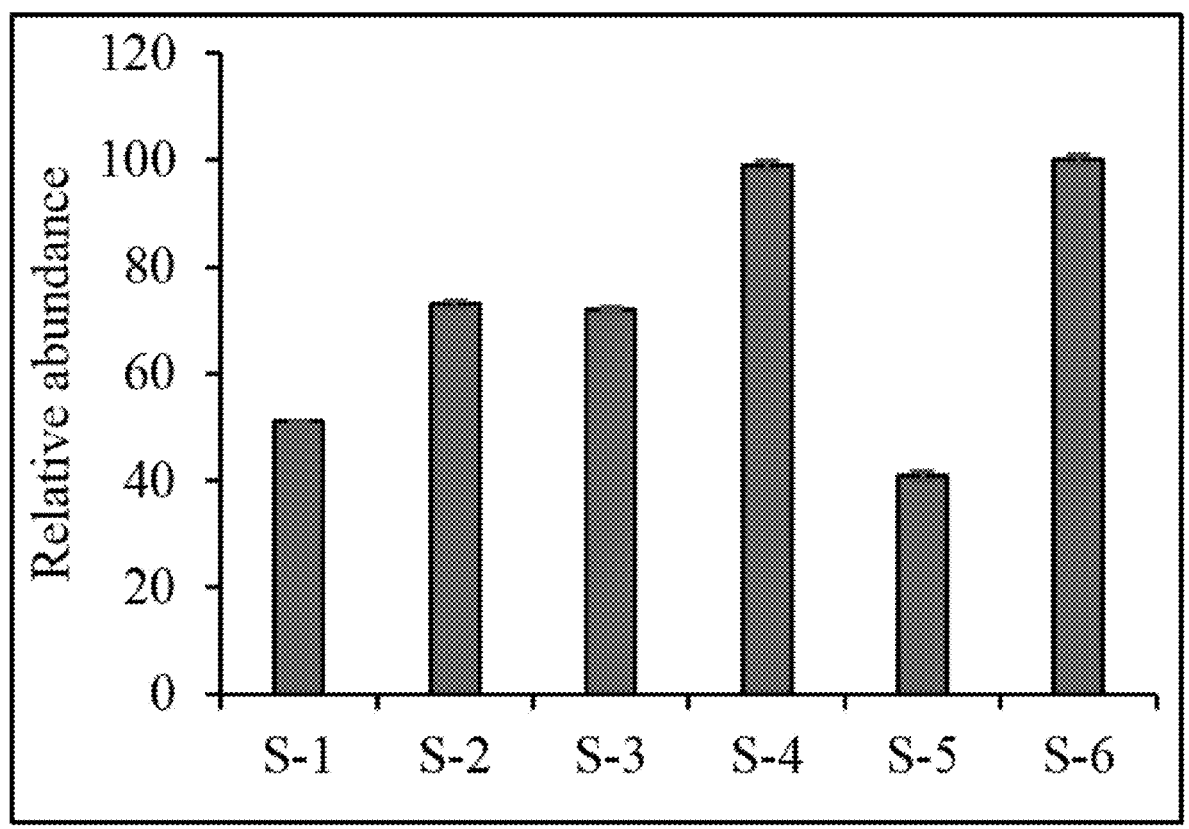

FIGS. 27A-27E: Tailoring of the elution solvent for MC-LR (FIG. 27A), MC-RR (FIG. 27B), MC-LA (FIG. 27C), MC-LF (FIG. 27D), MC-LW (FIG. 27E), and MC-YR (FIG. 27F) spiked in urine. Solvent compositions S-1 to S-6 are shown in Table 13 and the samples were analyzed in triplicate with UHPLC-QqQ-MS/MS.

Figure 28A:
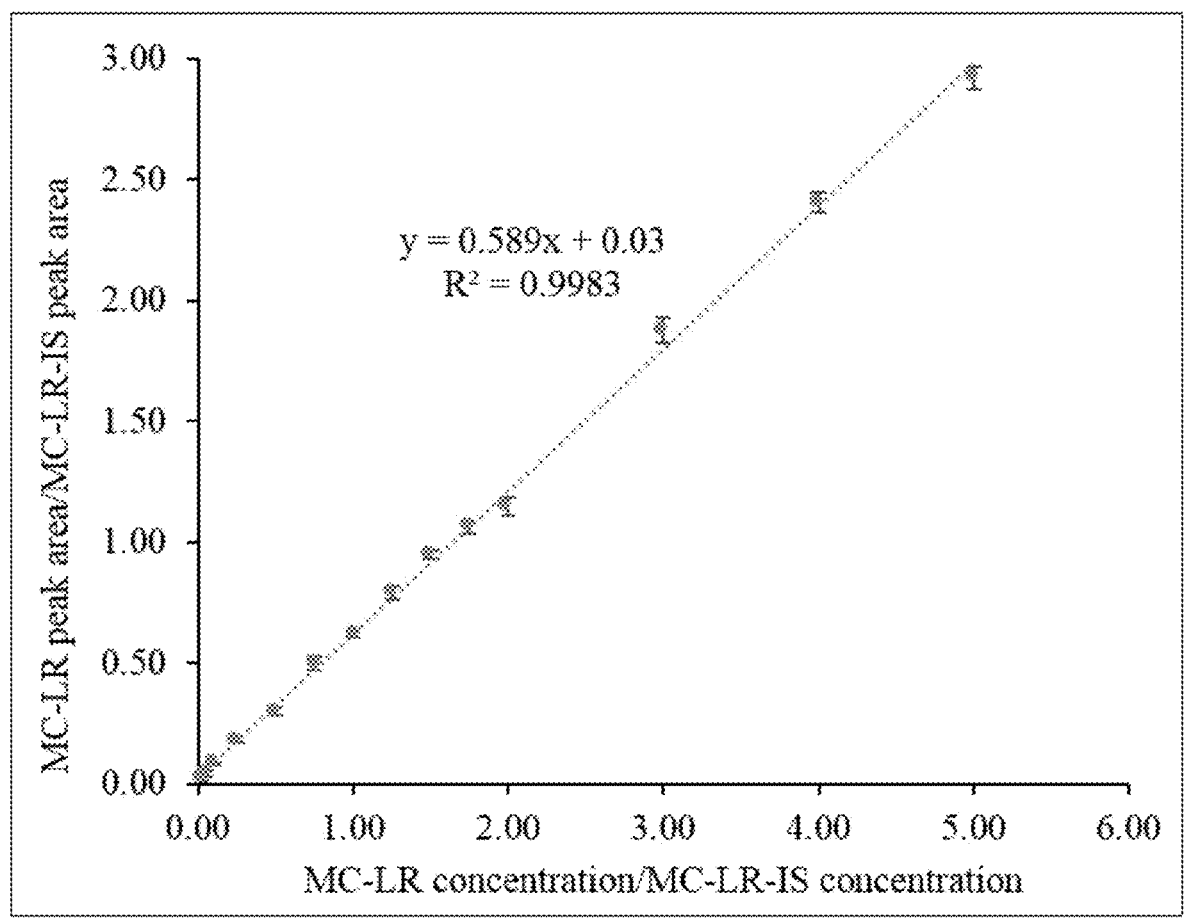
Figure 28B:
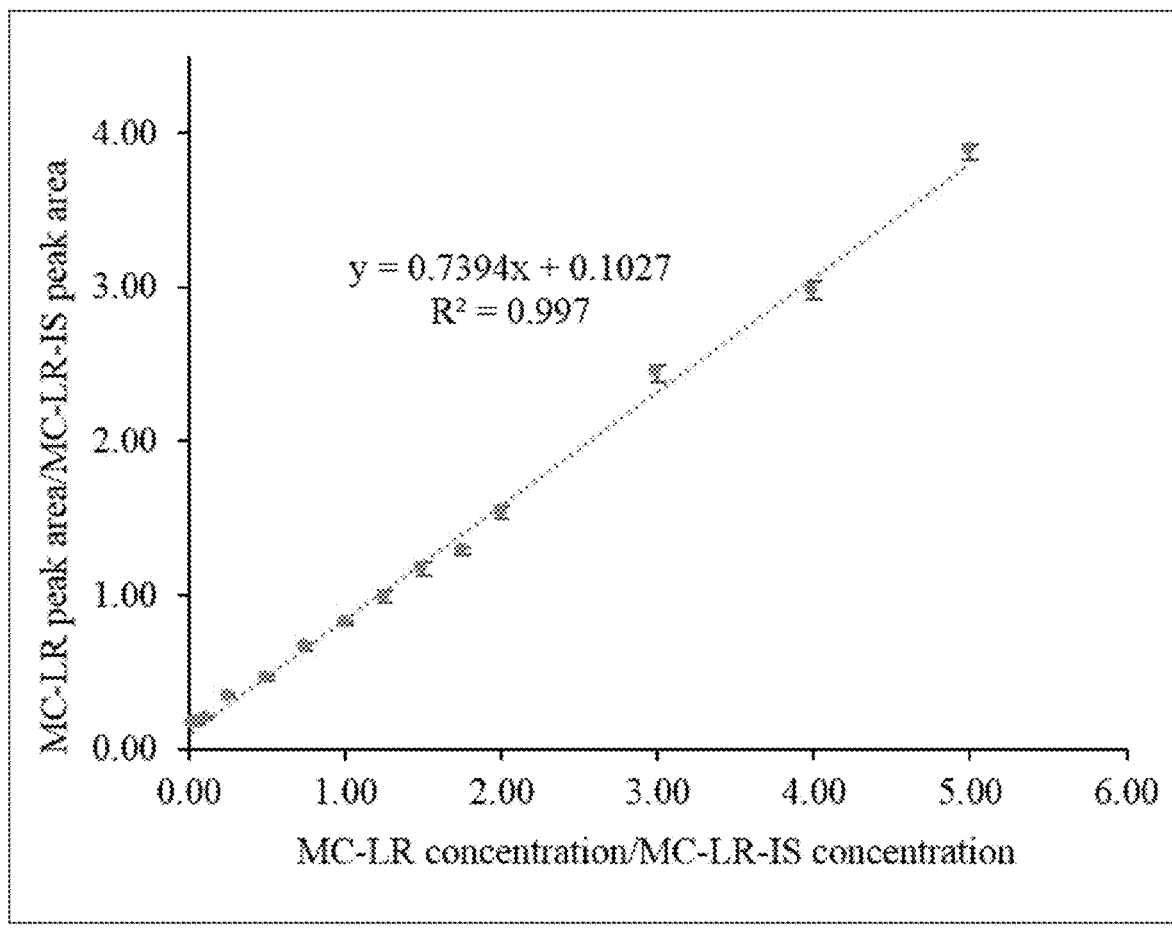

FIGS. 28A-28B: Internal standard calibration curve for quantification of MC-LR in mouse urine using peak areas of MRM chromatogram of MC fragment ions (m/z 135) obtained with UHPLC-QqQ-MS/MS (FIG. 28A), and peak areas of EIC chromatogram of MC monoisotopic ions obtained with HPLC-orbitrap-MS (FIG. 28B).

Figure 29:
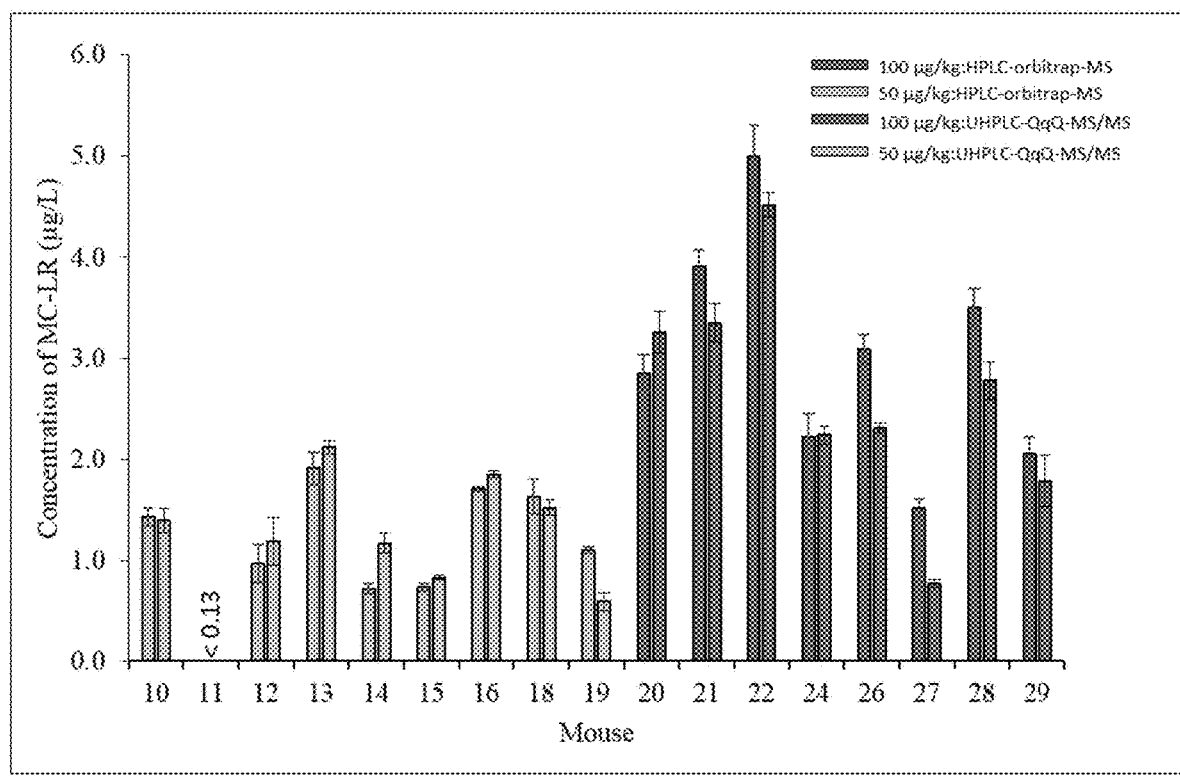

FIG. 29: Concentration of MC-LR in mouse urine samples analyzed using UHPLC-QqQ-MS/MS and HPLC-orbitrap-MS in triplicate runs.

DETAILED DESCRIPTION OF THE INVENTION

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

For convenience, various terms are defined before further description of the present disclosure.

The terms "limit of quantification", "quantification limit", or "LOQ" refer to the lowest concentration of an analyte which can be quantitatively determined with suitable precision and accuracy (i.e., at which the performance of a method or measurement system is acceptable for a specified use).

The terms "limit of detection", "detection limit", or "LOD" refer to the lowest quantity of a substance that can be distinguished from the absence of that substance within a certain confidence limit, but not necessarily quantitated as an exact value. A detection limit is generally determined by the analysis of samples with known concentrations of analyte and by establishing the minimum level at which the analyte can be reliably detected.

The acronym "LC" refers to liquid chromatography. The acronym "ESI" refers to electrospray ionization. The acronym "MS" refers to mass spectrometry. Thus, the term "LC-MS" refers to liquid chromatography-mass spectrometry, and the term "LC-ESI-MS" refers to liquid chromatography-electrospray ionization mass spectrometry.

The acronym "SIM" refers to selected-ion monitoring, which is a mode of operation for mass spectrometers wherein only one or more selected mass-to-charge ratios (m/z values) are detected in the analysis. Thus, the term "SIM-MS" refers to a mass spectrometry analysis wherein only one or more selected m/z values are detected in the analysis. Similarly, the term "LC-SIM-MS" refers to a liquid chromatography-mass spectrometry technique wherein only one or more selected m/z values are detected in the analysis.

The term "MS/MS" refers to a mass spectrometry technique that uses two mass analyzers in tandem with a collision gas cell between the two mass analyzers. Precursor ions selected by the first mass analyzer collide with a high pressure gas in the cell and undergo fragmentation, resulting in daughter ions that are analyzed by the second mass analyzer. Thus, the term "ESI-MS/MS" refers to electrospray mass spectrometry with two mass analyzers in tandem, and the term "LC-ESI-MS/MS" refers to liquid chromatography-electrospray mass spectrometry with two mass analyzers in tandem.

Though various solvent concentrations are described for exemplary purposes, it is understood that some modifications to these concentrations are entirely encompassed within the scope of the present disclosure. For example, where 0.1% formic acid is described, it is understood that 0.05% formic acid, or 0.2% formic acid, or 1.5% formic acid could also be used to obtain similar, though perhaps not optimal, results. Similarly, where 90% acetonitrile or 90% methanol are described, it is understood that these solvents could be utilized in the same manner at concentrations of, for example, 85% or 95%, and similar though perhaps not optimal results would be obtained.

Provided herein are methods for the quantification of one or more microcystin compounds using LC-MS or LC-MS/MS, along with an optional solid-phase extraction (SPE) preconcentration procedure beforehand. Structural characterization and quantification of MCs by orbitrap mass spectrometers indicates that high mass accuracy of these instruments can be beneficial for LC-MS and LC-MS/MS analyses of MC-LR. Thus, the method herein utilizes an orbitrap mass spectrometer, as will be explained in more detail.

In accordance with the present disclosure, a reproducible and efficient solid-phase extraction (SPE) method is provided for the purification and high-recovery preconcentration of MC-LR. Additionally, an LC-ESI-MS method using an HPLC orbitrap fusion MS system is provided for the accurate quantification of MC-LR. Together, the SPE method and the HPLC Orbitrap Fusion MS quantification yield a significantly improved ability to detect and quantify MCs. Moreover, provided is a method for separating a mixture of multiple MCs, and detecting each of at least six different MC species with a low LOQ.

In one aspect, the method for detecting and quantifying microcystin generally involves a SPE purification and preconcentration method, and a quantitative analysis step. The SPE purification and preconcentration method includes the steps of conditioning an SPE cartridge, equilibrating the cartridge, loading samples, desalting the loaded samples, and eluting the sample. The method may also include evaporating solvent from the eluted sample, and then redissolving the sample in a solvent. However, the desalting step is optional. The purpose of the desalting step is to remove salts and other impurities that would interfere with further analysis. Thus, the desalting step may be omitted, such as when ultrapure solvents are used for preparing the samples. However, the desalting step is particularly advantageous when natural water sources, such as lake water or river water, are being analyzed, because of the high amounts of impurities generally found in such water. Therefore, the desalting step is important for analyses of microcystins in complex (e.g., environmental) water samples.

In one non-limiting example, the conditioning step involves 3 mL of 90/10 methanol/water with 0.1% formic acid. In one non-limiting example, the equilibration step involves 2 mL of 0.1% formic acid in water. In one non-limiting example, the loading step involves loading 5 mL of samples in water. In one non-limiting example, the desalting step involves washing the samples with 1 mL of 0.1% formic acid in water. In one non-limiting example, the eluting step involves washing the cartridge with 1.5 mL of 90/10 acetonitrile/water with 0.1% formic acid. In some embodiments, the SPE cartridge is a C18 cartridge. Without wishing to be bound by theory, it is believed that the eluting step involving acetonitrile is particularly advantageous for the preconcentration of microcystins because acetonitrile is effective for the elution of peptides from SPE cartridges. Overall, the SPE purification and preconcentration of microcystins demonstrates excellent recoveries of MC-LR from dilute samples.

Following preconcentration, the quantitative analysis step generally involves LC/ESI-MS analysis with a high-resolution Orbitrap Fusion mass spectrometer or with a triple quadrupole (QqQ) mass spectrometer. An HPLC is coupled to a high-resolution orbitrap fusion mass spectrometer to perform targeted LC-MS and LC-MS/MS quantifications of microcystins. The term "Orbitrap Fusion mass spectrometer" is used herein to generically describe a mass spectrometer that combines an orbitrap mass analyzer with a quadrupole and a linear ion trap. An orbitrap mass analyzer is one in which ions combine rotation around an electrode system with harmonic oscillations along the axis of rotation at a frequency characteristic of their mass-to-charge (m/z) ratio. A time-domain signal is collected from coherently oscillating ions, and a Fourier transform of this signal provides a mass spectrum. Thus, an orbitrap mass analyzer is a type of Fourier transform mass analyzer. A quadrupole is a component of a mass analyzer that filters sample ions based on the stability of their trajectories in oscillating electric fields that are applied to four parallel, metals rods. A linear ion trap is one in which ions are confined radially by a two-dimensional radio frequency (RF) field, and axially by stopping potentials applied to end electrodes. The term "high-resolution" means the m/z for each ion is measured to several decimal places. The combination of these features results in a mass spectrometer that provides superior results in quantifying microcystins. Similarly, a QqQ mass spectrometer is a tandem mass spectrometer having two quadrupole mass analyzers in series with a RF-only quadrupole between them to act as a cell for collision-induced dissociation. As described in the examples herein, a QqQ mass spectrometer may be useful for analyzing MC levels in samples of urine, plasma, or serum.

Calibration curves can be constructed to quantify the MCs in a mixture. A calibration curve is a commonly used approach for determining the concentration of a substance in an unknown sample by comparing the unknown to a set of standard samples of known concentration. Without preconcentration, the method herein can result in quantification of MCs ranging from 25 ppt (LOQ) to 1 ppb or more. With preconcentration, the method herein can quantify MCs in the concentration range from 500 ppq (LOQ) to 20 ppt or more. The LOQs of MCs of 25 ppt (25 ng/L) without preconcentration, and 500 ppq (500 pg/L) with preconcentration, are among the lowest achieved using LC-MS. Thus, the method provided herein represents a substantial improvement over known methods.

Further provided is a liquid chromatography method to separate and quantify multiple MCs in a mixture. High-performance liquid chromatography (HPLC) is a separation method that uses pumps to pass a pressurized liquid solvent containing the sample mixture (referred to as the mobile phase) through a column filled with a solid adsorbent material (referred to as the stationary phase). Each component in the sample interacts differently with the adsorbent material, causing different flow rates for the different compounds and thereby leading to the separation of the components as they flow out of the column. The sample mixture is introduced into the mobile phase in the column, and the components of the sample then move through the column at different velocities, which are a function of each component's physical interactions with the adsorbent material. The time at which a specific analyte emerges from the column is known as the retention time of the analyte.

Gradient HPLC involves altering the mobile phase composition during the analysis. Gradient HPLC generally utilizes an initial mobile phase composition that is selected such that the strength is appropriate to retain and resolve early-eluting analytes, the elution strength is increased in a predetermined way to elute compounds with optimum resolution, and the final mobile phase composition is chosen to ensure elution of all compounds of interest from the column within a reasonable time. Typically, two solvents are used, and are referred to as solvents A and B. Solvent A is usually the weaker solvent, and solvent B is usually the stronger solvent. The elution strength usually increases with time. The mixing of the two mobile phases is achieved using HPLC pumps, either at low pressure, in which the solvents are proportioned on the low-pressure side of the pump using solenoid valves, or at high pressure, where two or more pumps are used to deliver the solvents at different flow rates into a mixing chamber. As the mobile phase strength increases, the analyte begins to partition into the mobile phase and move along the column. As the mobile phase strength is increasing continuously, the rate at which the analyte moves along the column accelerates. At a certain point within the column elution, the analyte may be wholly partitioned into the mobile phase, and may be moving with the same linear velocity as the mobile phase.

Figure 13B:
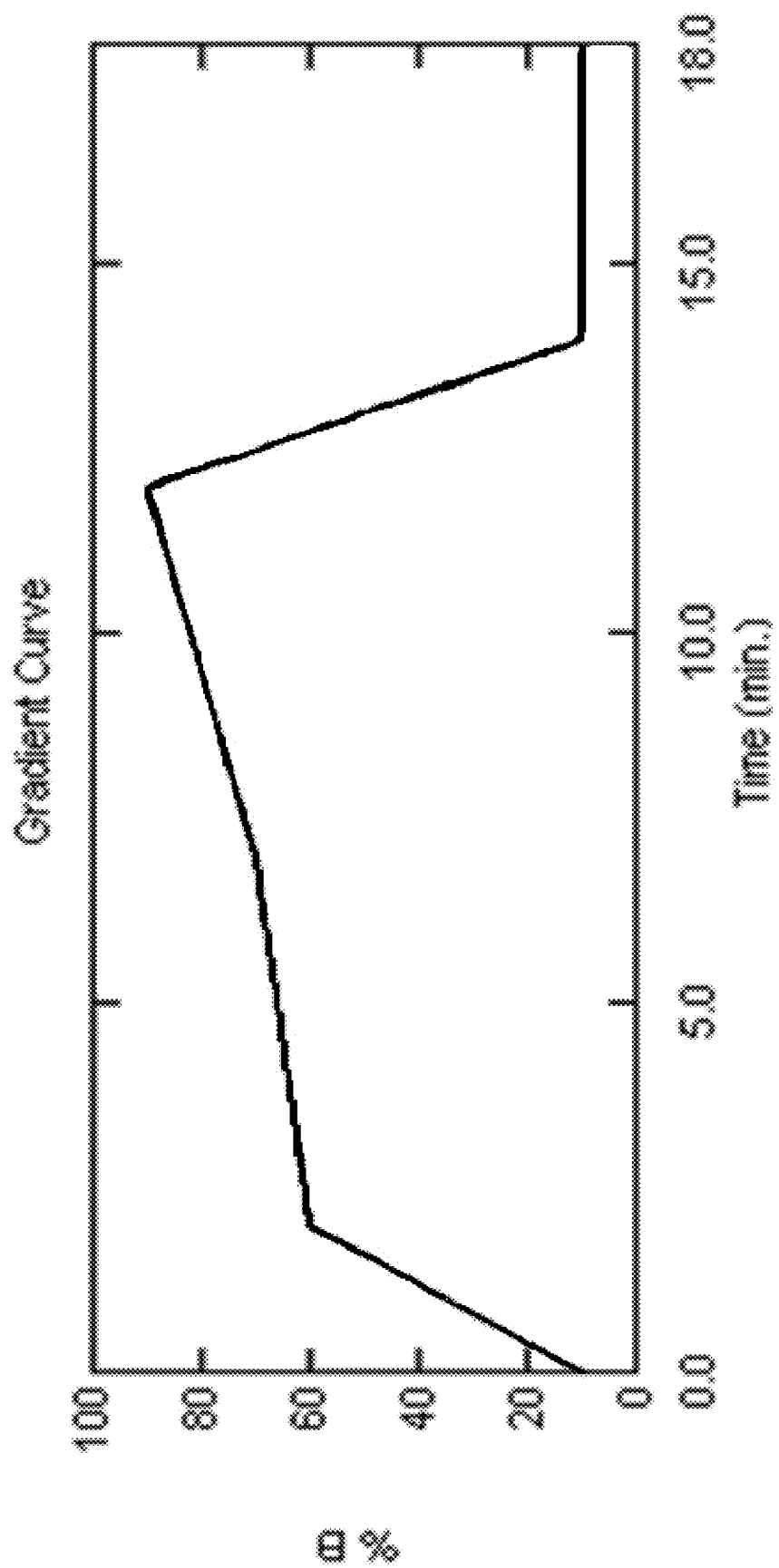

Provided herein is an HPLC method for the separation of multiple microcystin species in a sample. The HPLC method involves a gradient. Two pumps are utilized to produce a gradient that can separate multiple MC species in a mixture. For example, the liquid chromatography gradient can separate MC-LR, MC-YR, MC-RR, MC-LF, MC-LW, and MC-LA in a mixture. These six microcystin species are some of the most toxic and most common microcystins. To create the gradient mobile phase, a pump A pumps a solvent A, and a pump B pumps a solvent B. In some embodiment, solvent B is acetonitrile, and solvent A is 0.1% formic acid. In other embodiments, solvent B is 10% methanol with 0.1% formic acid, and solvent A is 0.1% formic acid with 20 mM ammonium formate. In one non-limiting example, the method involves the solvents acetonitrile in pump B and 0.1% formic acid in pump A, with the times and solvent parameters shown in Table 4 (FIG. 13A). This gradient curve is shown in FIG. 13B. In this example, the gradient mobile phase is created over 18 minutes by a solvent profile of 10% acetonitrile for minutes 0-2, 60% acetonitrile for minutes 2-7, 70% acetonitrile for minutes 7-12, 90% acetonitrile for minutes 12-14, and 10% acetonitrile for minutes 14-18. In another non-limiting example, the gradient mobile phase is created over 30 minutes by a solvent profile of 10% methanol with 0.1% formic acid for minutes 0-2, 80% methanol with 0.1% formic acid for minutes 2-16, 90% methanol with 0.1% formic acid for minutes 16-22, and 10% methanol with 0.1% formic acid for minutes 22-30.

The methods described herein are useful for analyzing microcystin content in dilute aqueous samples, as well as plasma, serum, or urine samples. The methods are particularly useful for the analysis of water samples from lakes, rivers, streams, and ponds, but may also be used for the analysis MC levels in human urine or human blood. The methods are also particularly useful for testing tap water samples to ensure the safety of drinking water. The sample can contain a plurality of microcystin species, which can be separated and quantified as described herein. The methods provided herein are capable of efficiently quantifying high-pg/L (ppq) concentrations of microcystin compounds by LC-MS after preconcentration, and ng/L (ppt) concentrations of microcystin compounds by LC-SIM-MS and LC-MS/MS without preconcentration. The methods provide limits of quantification (LOQs) and recoveries of MC-LR that are drastically improved over known methods.

It is further envisioned that the methods described herein may be embodied in the form of a kit or kits, such as a kit for the detection and quantification of microcystins in drinking water. Such a kit may include, for example, two or more of the SPE cartridges and solvents described herein, in separate containers, where the containers may or may not be present in a combined configuration. Many other kits are possible, such as kits further comprising one or more standard solutions for reference purposes, and kits including 96-well plates for high-throughput sample preparation and analyses, in which case multiple microcystins can be simultaneously purified and preconcentrated using SPE and sequentially analyzed by LC-MS using an autosampler. The kits may further include instructions for using the components of the kit to practice the subject methods. The instructions may describe, for example, a particular HPLC gradient useful for separating multiple microcystin species, and may further include example calibration curves. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Example 1

This example describes how an HPLC was coupled to an orbitrap fusion mass spectrometer to separate, identify, and quantify MC-LR at low concentration levels using high-mass accuracy, SIM-MS, and MS/MS capabilities of this instrument. The ng/L concentrations of MC-LR in water were quantified by LC-SIM-MS and LC-MS/MS. The LOQ of MC-LR was improved to pg/L levels by the development of an efficient SPE method for the recovery and preconcentration of MC-LR. Thus, this example demonstrates that the methods provided herein can be applied to efficiently and reproducibly preconcentrate, separate, and quantify MC-LR by a LC-orbitrap-MS system.

A high-performance liquid chromatography-electrospray ionization mass spectrometry (HPLC-ESI-MS) method was utilized for the quantification of the cyanobacterial toxin microcystin-LR (MC-LR) in water and in the aqueous solutions containing MC-LR, MC-LA, and MC-RR. While an HPLC binary gradient was applied for the separation of MCs in aqueous solutions and tap water, quantification of singly-charged MC-LR ion (m/z 995.56, z=+1) was achieved in selected ion monitoring (SIM) mode using an Orbitrap Fusion Tribrid mass spectrometer. All MC ions were detected with high mass accuracy of <3 parts per million (ppm) using the orbitrap mass analyzer and MC-LR was quantified using external calibration based on ion intensities. Calibration curves were linear, and limits of quantifications (LOQs) of MC-LR by LC-SIM-MS were 25 ng/L without preconcentration and 500 pg/L after MC-LR preconcentration. The percent recoveries of MC-LR after solid-phase extraction (SPE) and sample preconcentration were in the range from 98.35% to 99.85% with a relative standard deviation (RSD) of <3%, indicating that this is one of the most efficient and reproducible SPE methods for MC-LR recovery. Additionally, a LC-tandem mass spectrometry (MS/MS) method based on the measurement of the intensity of a characteristic MC-LR fragment ion (m/z 135.08) was established for quantification of MC-LR. Overall, MC-LR recovery and preconcentration method developed and LC-SIM-MS enable sensitive, selective, and reproducible quantification of MC-LR using MS and MS/MS capabilities of a high-mass accuracy orbitrap mass spectrometer.

Sample Preparation and Preconcentration

For sample preparation and preconcentration, MC-LR standards were made from a 500 ppm stock solution that was prepared by ethanol by the manufacturer. Other standard concentrations were prepared by diluting the 500 ppm stock in 90:10 (v:v) $CH_3OH$:$H_2O$ (HPLC-grade solvents). Initially, MC-LR standard samples were analyzed by LC-ESI-MS without preconcentration. In order to improve quantification limits, samples were preconcentrated using solid-phase extraction (SPE) before LC-MS analysis. SPE was performed using Sep-Pak C18 plus light cartridges (Waters). The cartridges were conditioned with 3 mL of 90:10 (v:v) $CH_3OH$:$H_2O$ with 0.1% FA and then equilibrated with 2 mL of 0.1% FA. The MC-LR sample was then diluted to 5 mL with water and loaded onto the cartridge. An optional sample desalting step was performed for the samples that were not prepared in HPLC-grade water (e.g., for tap water) by adding 1 mL of 0.1% FA onto the cartridge. The sample was then eluted and collected using 1.5 mL of 50:50 (v:v) $CH_3CN$:$H_2O$ containing 0.1% FA. The solvent was evaporated from the sample using a heated centrifuge at 45° C. for two hours. After evaporation, the sample was redissolved in 100 μL of 90:10 (v:v) $CH_3OH$:$H_2O$ containing 0.1% FA.

LC-ESI-ME Method

The HPLC method used was Method 544 developed by the EPA with various modifications. A selected ion monitoring (SIM) method (Thermo) was optimized for identification and quantification of MC-LR using Orbitrap Fusion-MS. SIM scans were set up for the singly-charged MC-LR ion (m/z 995.56), which were isolated using the quadrupole and an isolation width of 5 m/z units. The ions were detected using the orbitrap mass analyzer with the orbitrap resolution set to 120,000. External calibration curves were constructed to quantify MC-LR samples by analyzing standard MC-LR samples with concentrations from ~10 ppt-10 ppb (no sample preconcentration) and ~500 ppq-35 ppt (for preconcentrated samples).

Determination of SPE Preconcentration Recovery 1.25 ppb solution of MC-LR was prepared in 90:10 (v:v) $CH_3OH$:$H_2O$ by diluting a 500 ppm MC-LR stock solution. 100 μL of the 1.25 ppb MC-LR solution was transferred into a glass vial and diluted 50× to a final volume of 5.00 mL with HPLC-grade water (the after-dilution concentration of MC-LR was 25 ppt). The SPE protocol described above was used for the preconcentration experiments. To ensure that the results were reproducible from one cartridge to the next, each experiment was performed with three different SPE cartridges. Quantification of MC-LR eluted from each of the three SPE cartridges was performed by LC-ESI-MS in triplicate, and the percent recovery was calculated and averaged for MC-LR samples eluted from the three cartridges. The preconcentration procedure was also performed using an MC-LR sample with initial concentration of 750 ppt to ensure that the procedure was reproducible and efficient for samples containing lower concentrations of MC-LR. The limit of quantification (LOQ) of MC-LR in water samples that were not preconcentrated was ~10 ppt, which is comparable to the LOQ obtained using other similar instruments previously. The SPE method enabled high-recovery (>98%) preconcentration of MC-LR before LC-MS analyses. The recovery was better than reported in the literature (e.g., recovery ranged from ~82.4-117% in EPA method 544). The preconcentration improved the LOQ of MC-LR to ~500 ppq. Altogether, this example shows that the high-recovery SPE preconcentration method and LC-MS method characterized with high mass resolution, accuracy, and reproducibility, is useful for the detection of microcystin in water (e.g., in water plants), and is also useful in more complex samples (e.g., in environmental water samples).

Materials and Reagents

HPLC-grade acetonitrile ($CH_3CN$), methanol ($CH_3OH$), and water ($H_2O$) were obtained from Fisher Scientific (Pittsburgh, Pa., USA). Reagent-grade (≥95%) formic acid (FA) and ammonium formate were purchased from Sigma (St. Louis, Mo., USA). The stock solutions of 110 500 mg/L of MC-LR, 500 mg/L of MC-LA, and 100 mg/L of MC-RR prepared by the manufacturer in ethanol were purchased from Cayman Chemical Company (Ann Arbor, Mich., USA). Sep-Pak C18 Plus Light Cartridges were purchased from Waters (Milford, Mass., USA). Cellulose acetate membrane filters (0.2 μm pore size) were purchased from Fisher Scientific (Swedesboro, N.J., USA). 3 mL and 10 mL syringes were obtained from Becton, Dickinson and Company (Franklin Lakes, N.J., USA). 2 mL clear glass vials were purchased from Restek (Bellefonte, Pa., USA). The heated vacuum concentrator was from Eppendorf (Hamburg, Germany).

Standard Solution Preparation and SPE Protocol

MC-LR standards and blind standards were prepared by diluting the 500 mg/L stock solution using $CH_3OH:H_2O$ (90:10, v/v). Initially, MC-LR standard samples were analyzed by LC-ESI-MS without preconcentration. In order to improve the LOQ of MC-LR, the samples were purified using SPE and then preconcentrated before LC-MS analysis. The SPE cartridges were conditioned with 3 mL of $CH_3OH:H_2O$ (90:10, v/v) containing 0.1% FA and then equilibrated with 2 mL of 0.1% FA. The dilute aqueous solution containing MC-LR was loaded onto the SPE cartridge, although loading volume can be adjusted as needed. For the complex samples, such as tap water and river water, an optional washing step was performed after the loading step by adding 1 mL of 0.1% FA onto the cartridge. The sample was then eluted using 1.5 mL of $CH_3CN:H_2O$ (50:50, v/v) containing 0.1% FA, and collected in a glass vial. The sample was then preconcentrated by evaporating the solvent using a heated vacuum concentrator, and redissolved in a desired volume of $CH_3OH:H_2O$ (90:10, v/v) containing 0.1% FA before LC-MS analysis.

LC-MS

Initially, the HPLC (Shimadzu Technologies, Addison, Ill.) consisted of two LC-20AD pumps, DGU-20A3 degasser, a manual injector, and SCL-10A VP system controller. A CBM-20A system controller and an autosampler SIL-20A HT were then integrated into HPLC system to perform sequential automated injections of MC samples. Separation of MC-LR was performed on a 3.0 mm (i. d.)×100 mm (length) XBridge C8 column (Waters) packed with 3.5 μm-diameter C8 solid phase particles. HPLC binary gradient was established. The solvent flow rate was 0.3 mL/min and the sample injection volume was 20 μL. Mobile phase A consisted of water containing 0.1% FA and 20 mM ammonium formate while mobile phase B was methanol containing 0.1% FA. The gradient that was used for the separation and detection of MC-LR was 0-2 min 10% of B, 2-16 min 80% of B, 16-22 min 90% of B, 22-30 min 10% of B, and the run was stopped at 30 min.

For detection and quantification of MC-LR, the HPLC was coupled to an Orbitrap Fusion (Thermo Scientific, San Jose, Calif.) mass spectrometer, which contains a quadrupole, a linear ion trap, and an orbitrap mass analyzer. MS data were acquired using Xcalibur software (Thermo Scientific). The ESI-MS experiments were performed in positive ion mode using a heated ESI (HESI) source. Orbitrap mass analyzer was calibrated in the m/z range 100-2000 using a standard calibration mixture containing n-butylamine, caffeine, the peptide MRFA, and the synthetic polymer Ultramark 1621 (Thermo). A syringe pump (Chymex Inc, Stafford, Tex., USA) was used for direct sample infusion to optimize the HESI source conditions and instrument parameters prior to LC-MS. The spray voltage was 2400 V, sheath gas (nitrogen) flow rate was 35 arbitrary units (~4.1 L/min), auxiliary gas (nitrogen) flow rate was 10 arbitrary units (~8.0 L/min), ion transfer tube temperature was 325° C., and the vaporizer temperature was 285° C.

LC-ESI-MS and LC-ESI-MS/MS Quantification of MC-LR

The Orbitrap Fusion MS method was designed so that LC-SIM-MS and MS/MS scans were performed for the quantification of MC-LR during the same run for each sample. LC-SIM-MS utilized quadrupole to isolate singly-charged MC-LR ion (m/z 995.56) with an isolation width of 5 m/z units. Singly-charged protonated ions of MC-LA (m/z 910.49) and MC-RR (m/z 1038.57) were analyzed by LC-SIM-MS separately from MC-LR using also quadrupole isolation width of 5 m/z units. The intensity threshold was set to $1.0 \times 10^3$ with mass tolerance of 10 ppm. MC ions were detected using the orbitrap mass analyzer with the orbitrap resolution set to 120,000. The automatic gain control (AGC) target was $5.0 \times 10^4$ with the maximum injection time of 100 ms.

For quantification of MC-LR by LC-MS/MS, the precursor MC-LR ion (m/z 995.56) was selected by the quadrupole using an isolation window of 1.6 m/z units, and fragmented by higher-energy collisional dissociation (HCD) in the ion-routing multipole. MC-LR fragments were obtained using HCD collision energy of 45%, and the AGC target was set to $5.0 \times 10^4$ with the maximum injection time of 60 ms. Fragment ions were detected in the orbitrap mass analyzer with the orbitrap resolution set to 30,000. All samples were analyzed by LC-SIM-MS and LC-MS/MS in triplicate. The Qual Browser of Xcalibur software was used to display mass spectra and find ion intensities. Extracted ion chromatograms (EICs) were obtained using Xcalibur Quan Browser and displayed in the figures after performing a 5-point smoothing.

Quantification of MC-LR in Blind Standards and Tap Water

Two blind standards containing 2.00 µg/L and 22.50 ng/L of MC-LR were prepared, and the latter sample was purified by SPE and preconcentrated 50× before LC-MS analysis using the procedure described above. A sample of tap water (4.90 mL) was spiked with 100 µL of 1.25 µg/L solution of MC-LR yielding 25.00 ng/L solution of MC-LR, which was then purified by SPE and preconcentrated. The solutions of 3 µg/L MC-LR, 3 µg/L MC-LA, and 30 µg/L MC-RR were prepared by diluting MC stock solutions with $CH_3OH:H_2O$ (90:10, v/v). 100 µl of each of the three MC solutions was transferred into a 2 mL glass vial to prepare the sample containing 1 µg/L of MC-LR, 1 µg/L of MC-LA, and 10 µg/L of MC-RR. MC-LR in all of these samples was then quantified by LC-ESI-SIM-MS.

Quantification of MC-LR in Blind Samples and a Mixture with Other MCs by LC-ESI-MS A calibration curve was constructed by analyzing standard solutions in triplicate at eight concentration levels between 25 ng/L and 10 µg/L for the quantification of MC-LR in spiked HPLC-grade water samples. Blind samples containing 2.00 µg/L of MC-LR was prepared to validate the calibration curve.

The calibration curve was then applied to quantify MC-LR in a mixture with MC-LA and MC-RR. The solutions of 3 µg/L MC-lR, 3 µg/L MC-LA, and 3 µg/L MC-RR were prepared by diluting MC stock solutions with $CH_3OH:H_2O$ (90:10 v/v). 100 µl of each of the three MC solutions was transferred into a 2 mL glass vial to prepare the sample containing 1 µg/L of MC-LR, MC-LA, and MC-RR. MC-LR was then quantified by LC-ESI-SIM-MS.

Determination of Percent Recovery of MC-LR Using SPE

The percent recovery of the MC-LR was tested in HPLC-grade water and river water spiked with MC-LR. River water was collected from the Ottawa river (Toledo, Ohio, USA). River water was filtered through a cellulose membrane with a pore size of 0.20 µm.

The percent recovery was determined by spiking 1.25 µg/L and 750 ng/L solutions of MC-LR into HPLC-grade water and river water followed by using three C18 SPE cartridges for each concentration. The samples of MC-LR with concentrations of 1.25 µg/L and 750 ng/L were prepared by diluting 500 mg/L MC-LR stock solution in $CH_3OH:H_2O$ (90:10 v/v). Then, 100 µL of each solution (1.25 µg/L and 750 ng/L) was transferred into glass vials and diluted to a final volume of 5 mL with HPLC-grade or river water yielding 25 ng/L and 15 ng/L solutions of MC-LR, respectively. Three SPEs were performed for each concentration for both HPLC-grade water and river water samples as described in the SPE protocol. An additional washing step, also described above, was performed for the spiked river water samples to purify MC-LR further before the elution step. Each preconcentrated MC-LR sample was then redissolved in 100 µL of $CH_3OH:H_2O$ (90:10 v/v) and analyzed by LC-ESI-MS in triplicate. SPE was not performed for the control MC-LR solutions (1.25 µg/L and 750 ng/L).

To determine percent recovery, the intensity of the MC-LR ion (m/z 995.56) after SPE was divided by the intensity of this ion in a control sample and averaged for each concentration separately for both MC-LR spiked HPLC-grade and river water samples.

Quantification of MC-LR in Real World Samples

An LC-MS calibration curve was prepared after purifying and preconcentrating MC-LR solutions in tap water with concentrations between 500 pg/L and 35 ng/L. To validate the calibration curve, blind standards containing 22.50 ng/L and 25.00 ng/L of MC-LR were prepared in HPLC-grade water and tap water, respectively. 100 µL of 1.125 µg/L and 1.25 µg/L solutions of MC-LR were spiked into 4.90 mL of HPLC-grade and tap water to yield 22.50 ng/L and 25 ng/L concentrations of MC-LR respectively. Blind samples were purified by SPE and preconcentrated 50× before LC-MS analysis using the procedure described above for the SPE protocol.

The SPE method was further validated by quantifying MC-LR in spiked river water. The samples of MC-LR with concentrations of 100 ng/L, 250 ng/L, 500 ng/L, and 1 µg/L were prepared by diluting a 500 mg/L MC-LR stock solution in $CH_3OH:H_2O$ (90:10, v/v). Then, 100 µL of each solution was transferred into glass vials and diluted to a final volume of 5 mL with filtered river water yielding 2 ng/L, 5 ng/L, 10 ng/L, and 20 ng/L solutions of MC-LR, respectively. SPEs of MC-LR were performed for both calibration standards and river water samples. A calibration curve for quantification of MC-LR in spiked river water samples using LC-ESI-MS was constructed at eight concentration levels between 2 ng/L and 35 ng/L.

For all samples, LODs were obtained experimentally by analyzing spiked water samples with signal-to-noise (S/N) ratio ~3 from the extracted ion chromatograms, while LOQs were estimated from the chromatograms as the lowest validated concentration level that meets a S/N ratio equal to 10.

Results and Discussion

General Considerations Regarding MS and MS/MS Method

After optimizing ESI-MS detection of MC-LR using direct infusion, LC-SIM-MS analyses of MC-LR were performed. The singly-charged protonated MC-LR ion (m/z 995.56) was quantified by LC-MS in positive ion mode. SIM was chosen for the MS analyses because it enables detection and quantification of MC-LR with higher sensitivity than full MC scan. Selection of a SIM mass window was important because a narrow m/z window might result in the loss of the sensitivity, and a wide SIM range can cause interference from neighboring peaks. Therefore, a 5 m/z units window was selected using a quadrupole so that the mass range for SIM is centered at the exact precursor mass (m/z 995.56). MS and MS/MS were performed in parallel. In the SIM-MS scans, the orbitrap fusion mass spectrometer uses the quadrupole to isolate MC-LR ions, which are then stored in the IRM and injected using a C-trap into the orbitrap for mass analysis. For MS/MS, MC-LR ions were isolated within the specified mass range (1.6 m/z units), fragmented by HCD, and sent to the orbitrap for simultaneous mass analysis. Alternatively, targeted quantitation of MC-LR can be done using MS/MS in parallel to MS. ADDA fragment ion $[C_6H_5-CH_2CH(OCH_3)]^+ 200$ (m/z ~135.0810) formed due to the cleavage of the ADDA group (FIG. 1) and was used for quantification of MC-LR by LC-MS/MS. The high-throughput analysis was feasible since both SIM-MS and MS/MS scans were performed within the same method for each sample using the Orbitrap Fusion MS.

To improve parallel MS and MS/MS data acquisition by Orbitrap Fusion MS, parameters such as mass resolution, scan rate, AGC, and maximum injection time were adjusted starting from the default values. ~4 Hz orbitrap scan rate was set to obtain relatively high resolution during SIM scan. The AGC target value controls the number of ions that the ion optics injects into the orbitrap mass analyzer. Ions will stop filling orbitrap when AGC target is reached or when maximum ion injection time expires. A higher value of AGC target increases the sensitivity, but it might cause peak broadening due to space charging in the orbitrap. AGC and maximum injection time were balanced to obtain the best MC-LR signal in the method used.

Figure 2A:
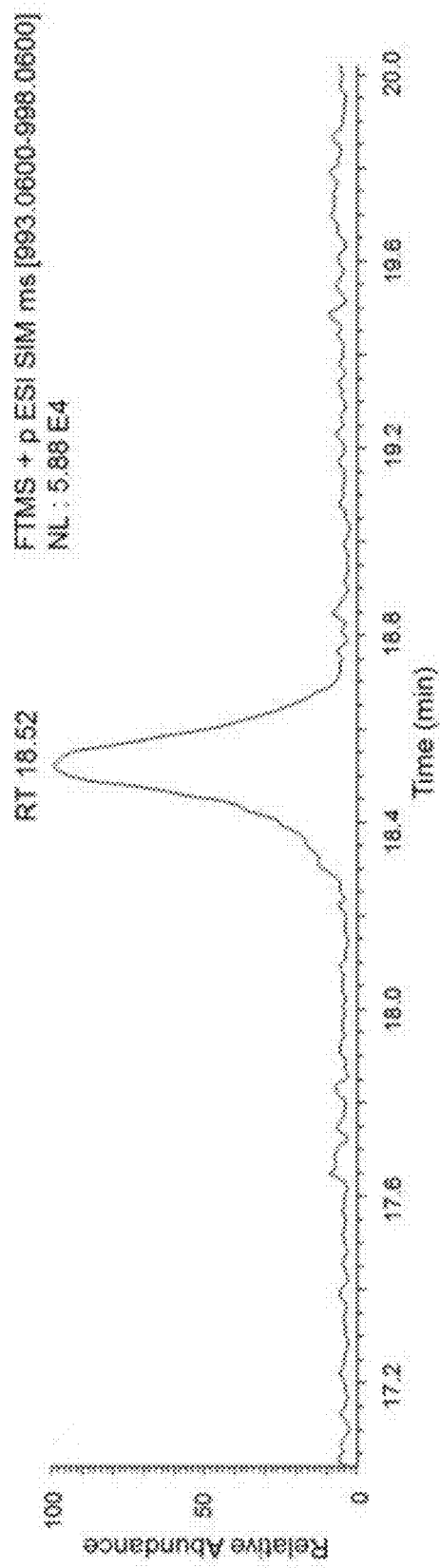
Figure 2B:
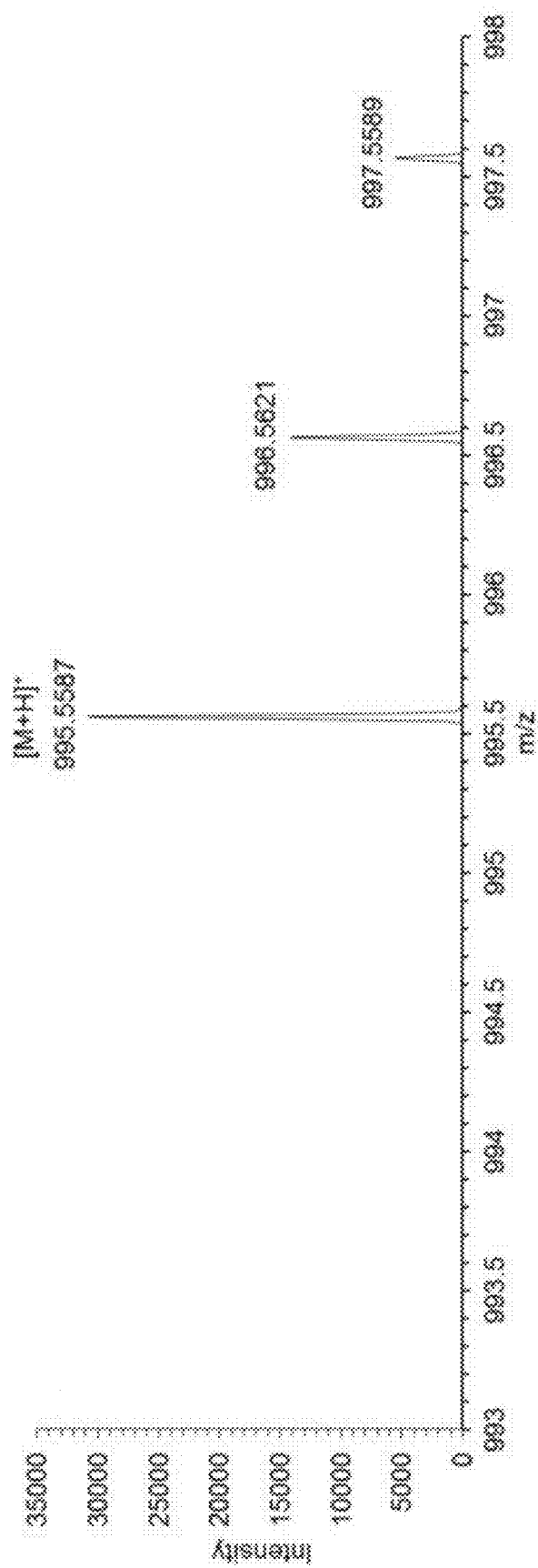

The EIC obtained upon LC-SIM-MS analysis of 1 µg/L solution of MC-LR indicates that its retention time is ~18.50 min (FIG. 2A). The ESI orbitrap mass spectrum clearly shows the monoisotopic peak of protonated MC-LR at m/z 995.5587 with other isotopic peaks resolved (FIG. 2B). Ions formed by ESI were analyzed using the orbitrap mass analyzer, which was externally calibrated to provide high-mass accuracy measurements. For example, m/z of monoisotopic MC-LR ion was measured with mass accuracy of ~2.1 ppm (Table 1), and this value falls within mass accuracy range (<3 ppm) of Orbitrap Fusion MS specified by the manufacturer (Thermo).

TABLE 1

Mass accuracies of singly-charged protonated ions of MC-LR, MC-LA, and MC-RR

| MC | Ion formula | Theoretical m/z | Experimental m/z[a] | Accuracy (ppm) |
| --- | --- | --- | --- | --- |
| MC-LR | $[C_{49}H_{74}N_{10}O_{12} + H]^+$ | 995.5566 | 995.5587 | −2.1094 |
| MC-LA | $[C_{46}H_{67}N_{7}O_{12} + H]^+$ | 910.4926 | 910.4934 | −0.8786 |
| MC-RR | $[C_{49}H_{75}N_{13}O_{12} + H]^+$ | 1038.5736 | 1038.5748 | −1.1554 |

[a]Values correspond to monoisotopic peaks in mass spectra shown in FIG. 2B

Quantification of MC-LR without Preconcentration

The intensity of the ion with m/z 995.56 was used for LC-SIM-MS quantification of MC-LR in water using external calibration. The MC-LR standards were prepared, analyzed in triplicate, and the intensities were averaged to generate each point of the calibration curve shown in FIG. 3. This calibration curve was obtained for MC-LR without preconcentration over the concentration range of 25 ng/L to 10 µg/L with the standard deviations included as error bars. The calibration curve was linear with an excellent $R^2$ value of 0.9999. Lower concentrations of MC-LR can be detected (LOD~10 ng/L), but cannot be quantified using orbitrap without preconcentration of the sample prior to analysis. Without sample preconcentration, the LOQ of MC-LR by LC-SIM-MS was 25 ng/L, and the EIC and mass spectrum of MC-LR corresponding to the LOQ are shown in FIG. 4. The LOQ of MC-LR obtained using Orbitrap Fusion Tribrid MS is improved compared to the LOQs measured by other models of orbitrap mass spectrometers.

The calibration curve was validated using a blind standard, which was made by one individual and then analyzed by a different individual. After LC-SIM-MS analyses were performed, it was determined that concentration of MC-LR in the blind standard was 1.92 µg/L while the actual concentration of MC-LR was 2.00 µg/L (Table 2). The results of this experiment indicate that the quantification of MC-LR using calibration curve in FIG. 3 was accurate (4.85% RSD).

TABLE 2

Validation of calibration curves for quantification of MC-LR using LC-MS

| MC-LR sample | MC-LR concentration | Calculated concentration | RSD (%) |
| --- | --- | --- | --- |
| Analyzed without preconcentration: | | | |
| Blind standard | 2.00 µg/L | 1.92 µg/L | 4.85 |
| Mixed with MC-RR and MC-LA | 1.00 µg/L | 0.97 µg/L | 2.18 |

TABLE 2-continued

Validation of calibration curves for quantification of MC-LR using LC-MS

| MC-LR sample | MC-LR concentration | Calculated concentration | RSD (%) |
| --- | --- | --- | --- |
| Analyzed after preconcentration: | | | |
| Blind standard | 22.50 ng/L | 22.77 ng/L | 7.92 |
| Spiked in tap water | 25.00 ng/L | 25.45 ng/L | 2.21 |
| Spiked in river water | 2.00 ng/L | 1.62 ng/L | 8.11 |
|  | 5.00 ng/L | 4.28 ng/L | 6.82 |
|  | 10.00 ng/L | 10.35 ng/L | 3.91 |
|  | 20.00 ng/L | 20.76 ng/L | 2.24 |

Figure 3:
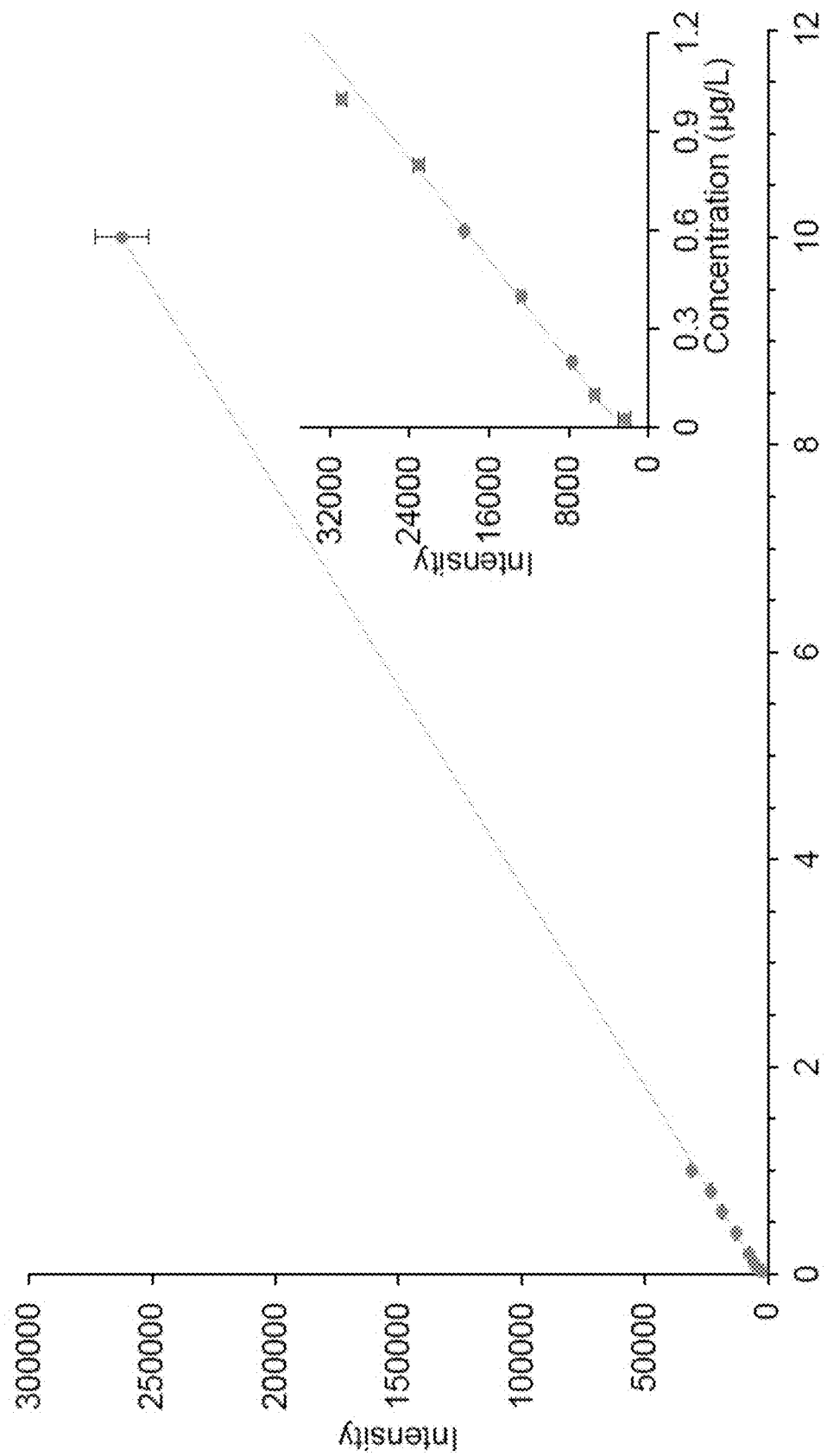
Figure 4A:
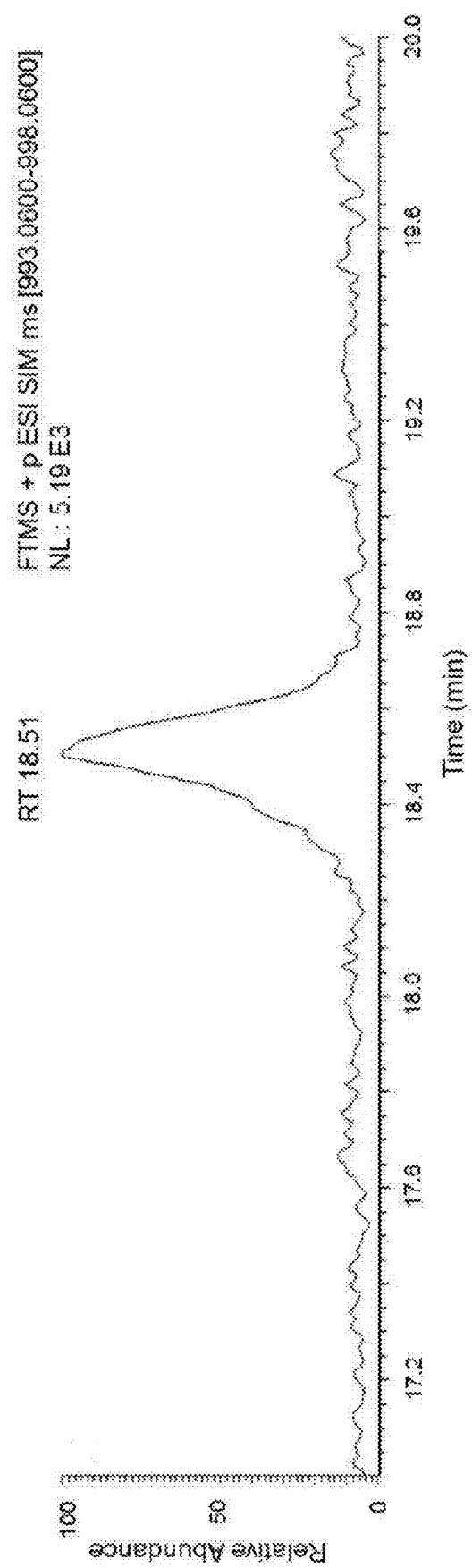
Figure 4B:
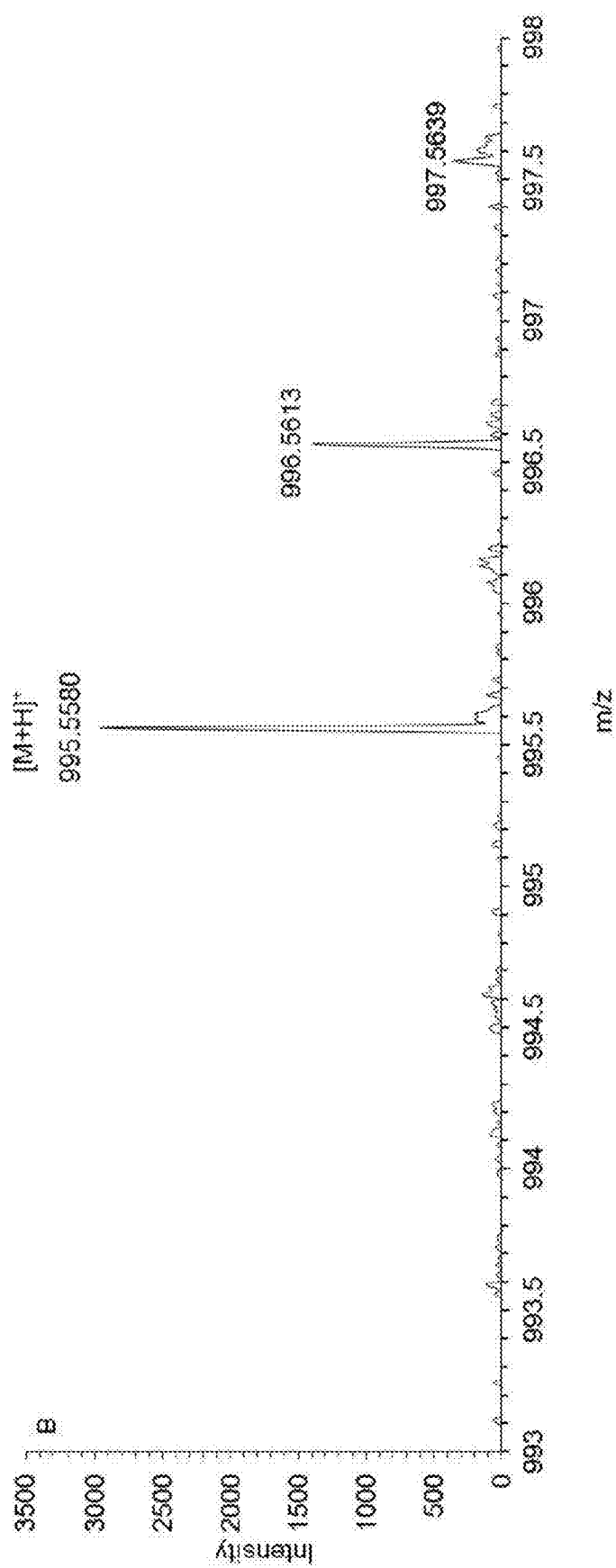
Figure 18:
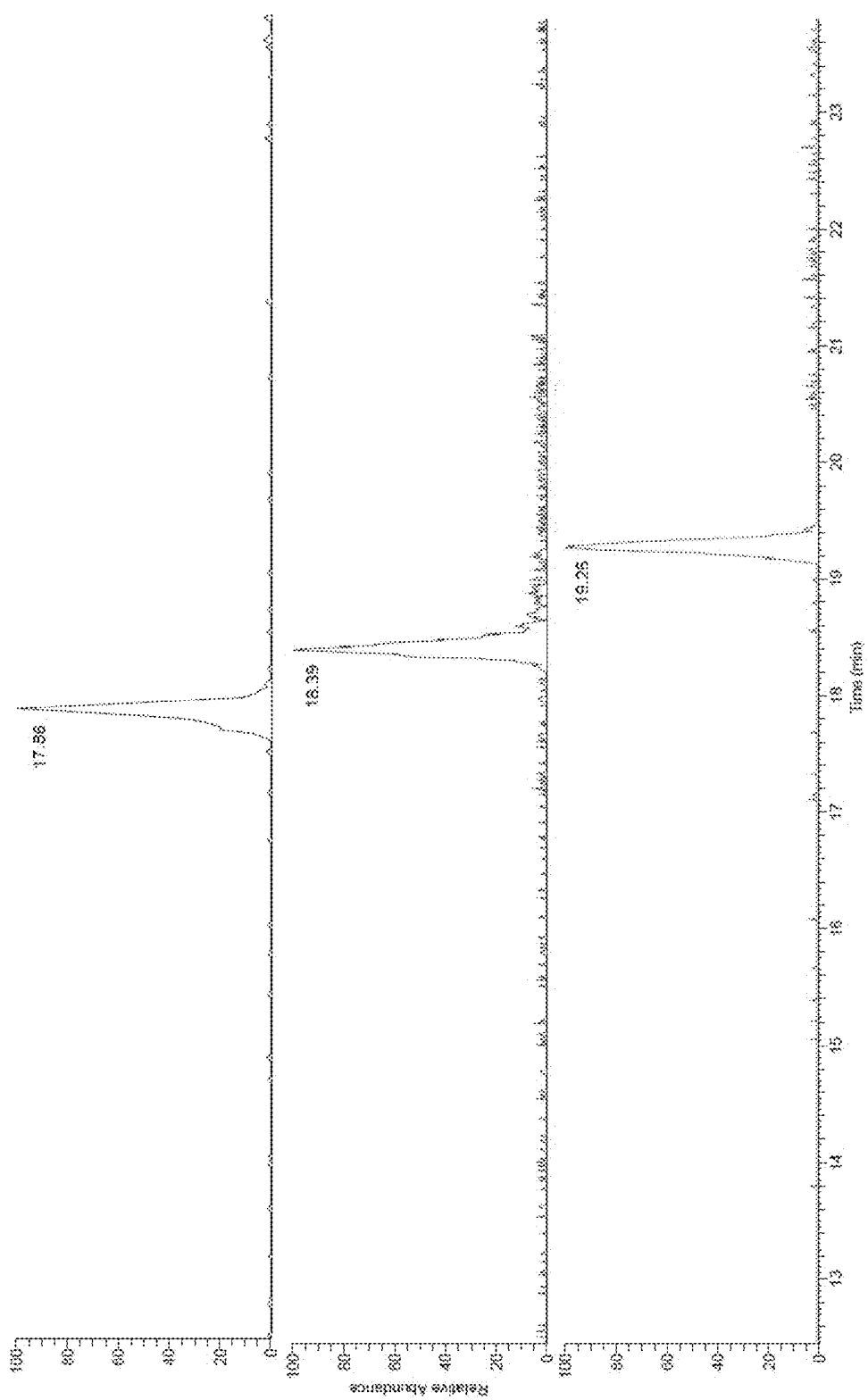
Figure 19A:
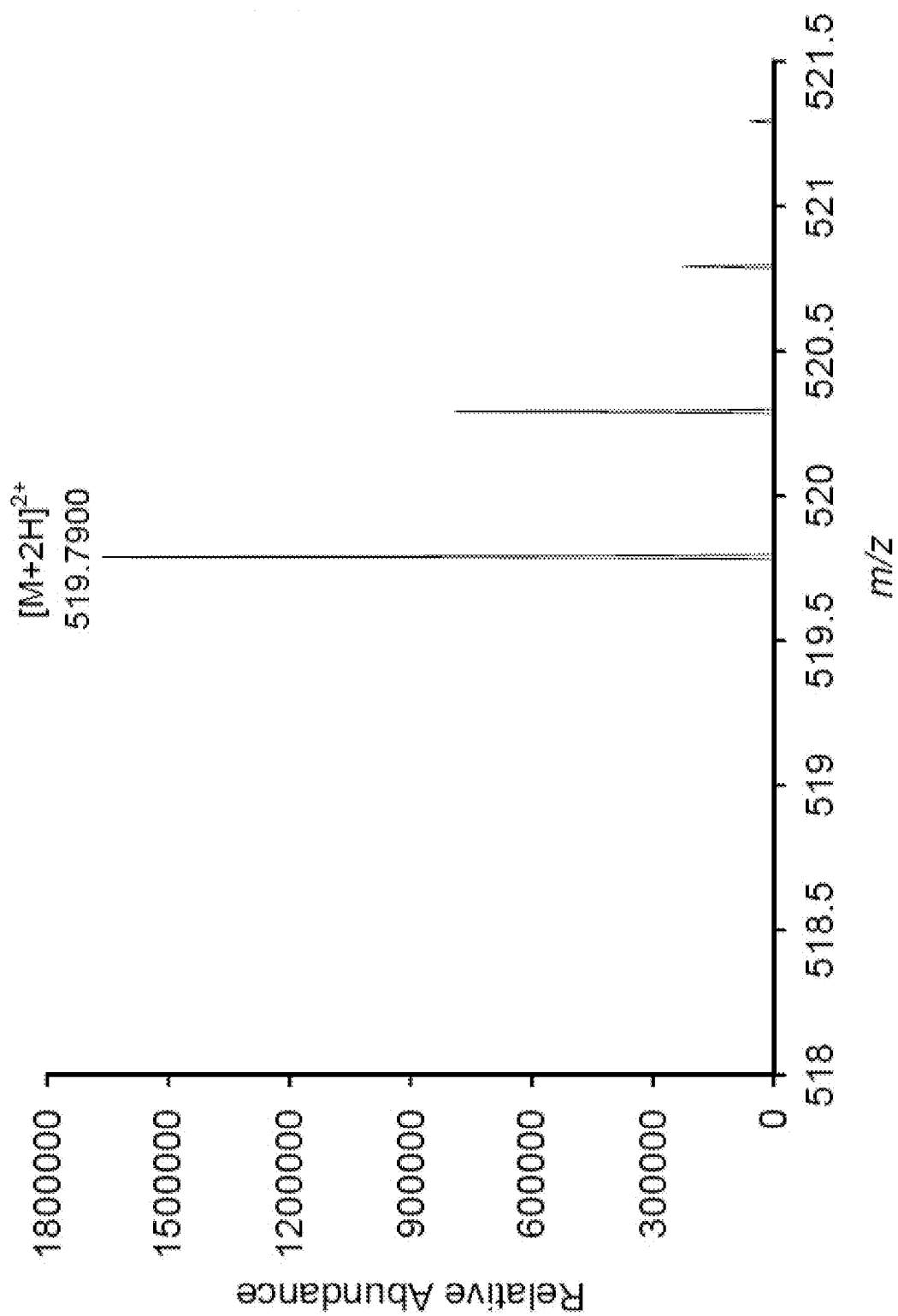
Figure 19B:
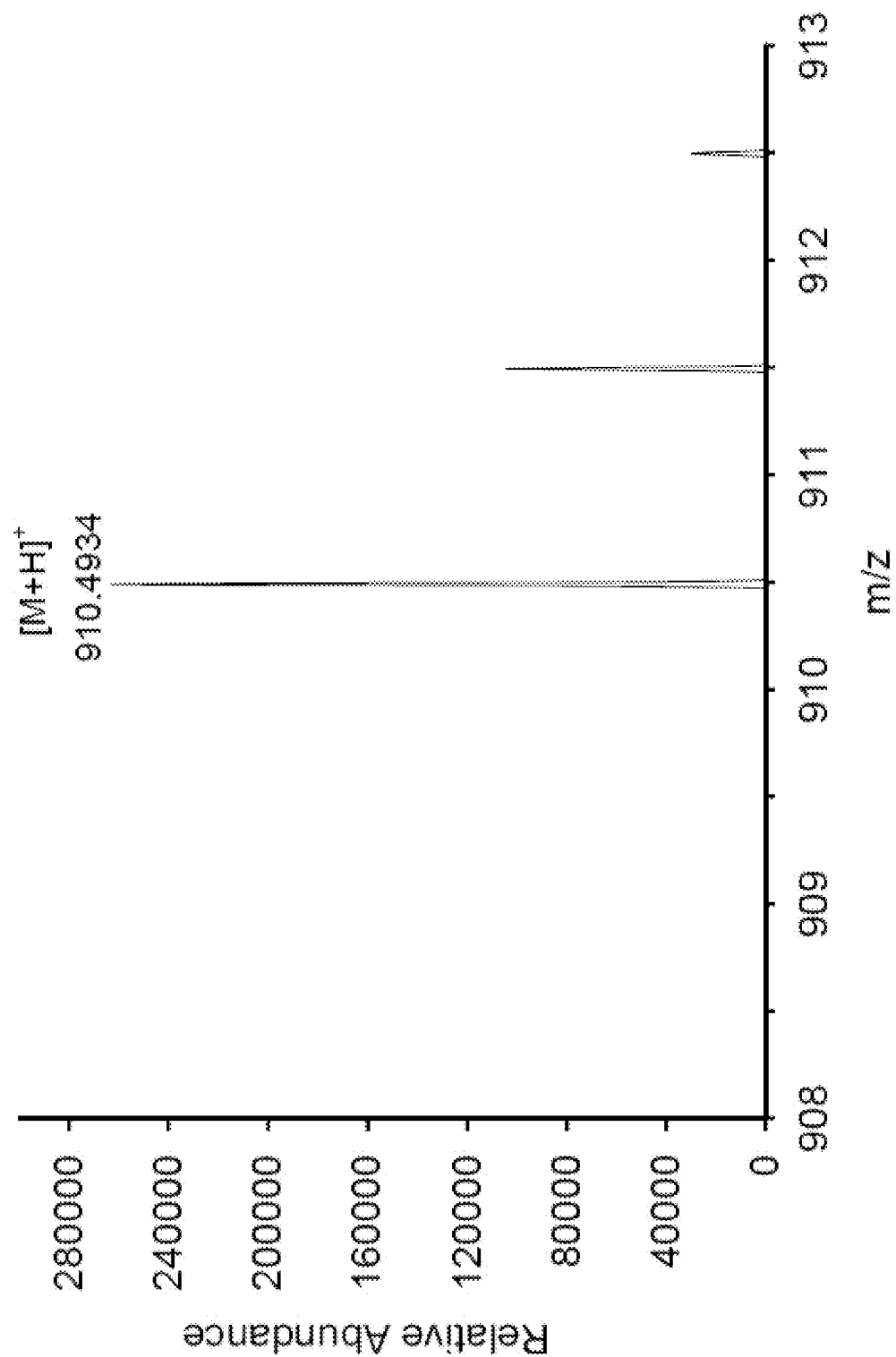

The calibration curve shown in FIG. 3 was then applied to quantify MC-LR in more complex samples. HPLC separation of MC-LR was performed in a mixture containing 1 µg/L of MC-LR, MC-LA, and MC-RR. The intensities of singly-charged MC-LR and MC-LA ions and doubly-charged MC-RR ion, whose m/z values are shown in Table 1, were monitored individually by SIM-MS. FIG. 18 shows the EICs for MC-RR ($t_R$=17.86 min), MC-LR ($t_R$=18.39 min), and MC-LA ($t_R$=19.26 min). FIGS. 19A-19B show the mass spectra of MC-LA and MC-RR, and m/z values of their singly and doubly charged ions, respectively, were measured with excellent mass accuracies <3 ppm (Table 1). Since pure stock solutions of MCs were used for preparation of the mixture, sample purification using SPE was not necessary before the LC-SIM-MS analysis. The concentration of MC-LR in the mixture with other MCs, measured using LC-SIM-MS of MC-LR ion with m/z 995.56 and the calibration curve in FIG. 3, was 0.97 µg/L (Table 2), showing 2.18% RSD in comparison to initial concentration of MC-LR (1.00 µg/L).

Quantification of MC-LR after Preconcentration

To analyze MC-LR samples of lower concentrations and higher complexity, a method for the purification of MC-LR using SPE was developed and used for the preconcentration of the sample. The accuracy and the precision of the developed SPE method were evaluated in a recovery experiment by analyzing MC-LR spiked HPLC-grade water and river water samples at two concentration levels (25 ng/L and 15 ng/L). River water was selected for the analyses to evaluate possible matrix effects on recovery of MC-LR using the developed SPE method.

MC-LR solutions were purified using C18 SPE cartridges and preconcentrated 50× as described above. The loading volume of the cartridge was kept at 5 mL, but it can be increased or decreased depending on the concentration of MC-LR in the solution. Low loading volumes minimize the sample preparation time and reduce potential losses of MC-LR in the SPE column during sample loading.

Average percent recovery was determined by comparing MS intensities of the protonated MC-LR ion (m/z 995.56) in preconcentrated samples and standard samples containing 1.25 µg/L and 750 ng/L of MC-LR (Table 3). Accuracy of the SPE method expressed as average recovery ranged from 98.35% to 99.85% and 97.55% to 98.52% for MC-LR spiked HPLC-grade water and river water, respectively, at the two concentrations. Precision of the developed SPE method expressed as RSD was calculated from three replicates on each concentration using three different SPE C18 cartridges for each water sample. In all cases, RSDs were below 3.00% for MC-LR spiked HPLC-grade water and river water samples (Table 3). RSD of the signal intensities of LC-ESI-MS trials was less than or equal to 4.68%, which shows excellent reproducibility of the MS method.

TABLE 3

Percent recovery of MC-LR after SPE purification and preconcentration of 25 ng/L and 15 ng/L solutions of MC-LR, which were preconcentrated 50x to yield ~1.25 µg/L and ~750 ng/L standard solutions of MC-LR, respectively

|  | Percent recovery (%) | RSD for signal intensity (%) |
| --- | --- | --- |
| MC-LR concentration- 750 ng/L | | |
| Spiked HPLC-grade water | | |
| Cartridge 1 | 99.01 | 2.65 |
| Cartridge 2 | 99.24 | 2.19 |
| Cartridge 3 | 99.84 | 2.64 |
| Average recovery (%) | 99.37 | |
| RSD for recovery (%) | 2.20 | |
| Spiked river water | | |
| Cartridge 1 | 98.00 | 2.02 |
| Cartridge 2 | 98.35 | 2.25 |
| Cartridge 3 | 98.52 | 2.92 |
| Average recovery (%) | 98.29 | |
| RSD for recovery (%) | 2.10 | |
| MC-LR concentration- 1.25 µg/L | | |
| Spiked HPLC-grade water | | |
| Cartridge 1 | 98.65 | 3.83 |
| Cartridge 2 | 99.85 | 0.79 |
| Cartridge 3 | 98.35 | 3.33 |
| Average recovery (%) | 98.95 | |
| RSD for recovery (%) | 2.63 | |
| Spiked river water | | |
| Cartridge 1 | 98.48 | 2.16 |
| Cartridge 2 | 98.12 | 4.68 |
| Cartridge 3 | 97.55 | 2.90 |
| Average recovery (%) | 97.89 | |
| RSD for recovery (%) | 3.00 | |

The SPE method demonstrates higher recovery of MC-LR as well as better reproducibility and accuracy than known methods for MC-LR preconcentration. In addition, the excellent percent recoveries of MC-LR in both HPLC-grade and river water indicate the developed SPE method can be used for quantification of MC-LR in more complex samples.

Figure 5A:
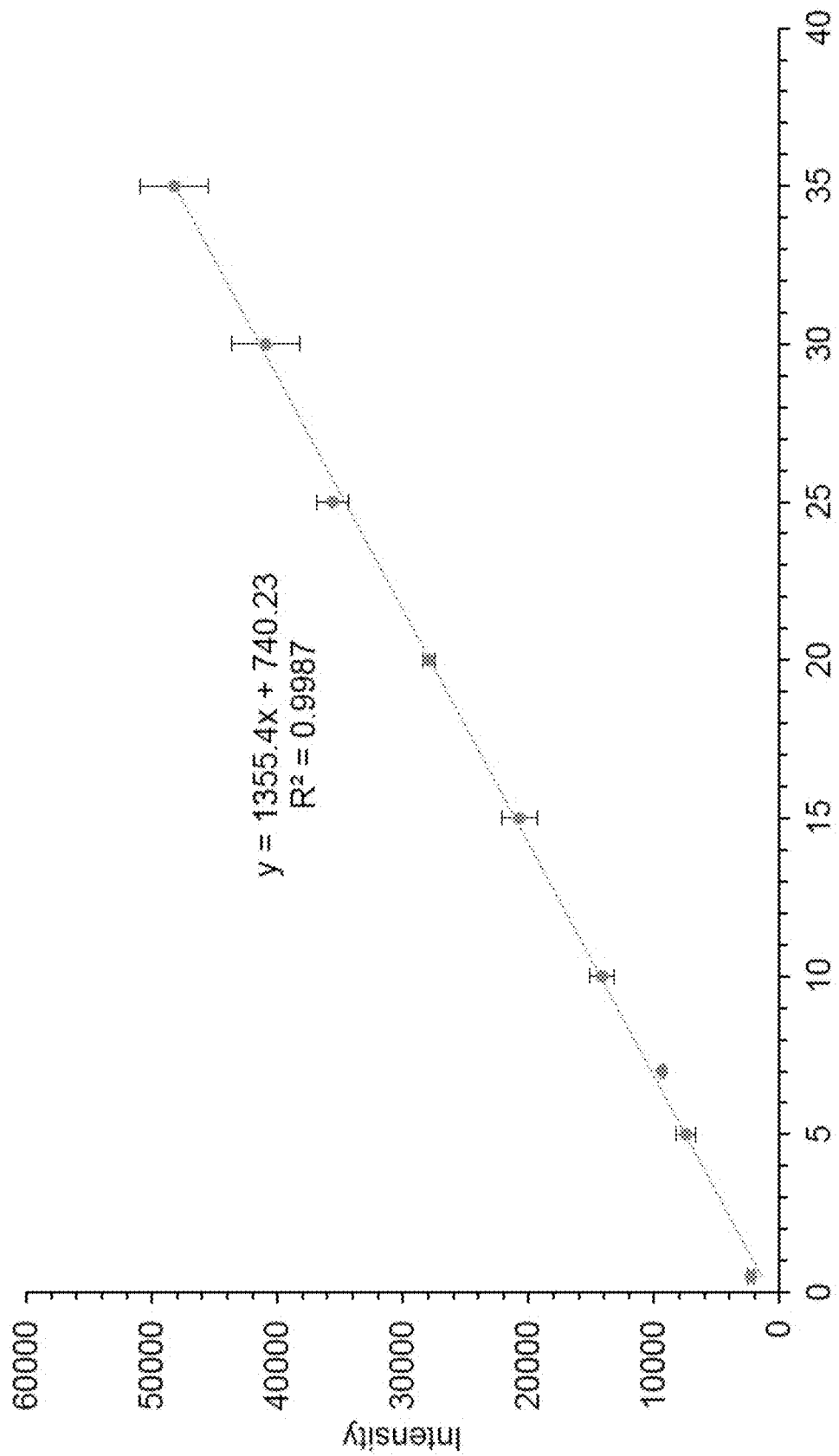
Figure 5B:
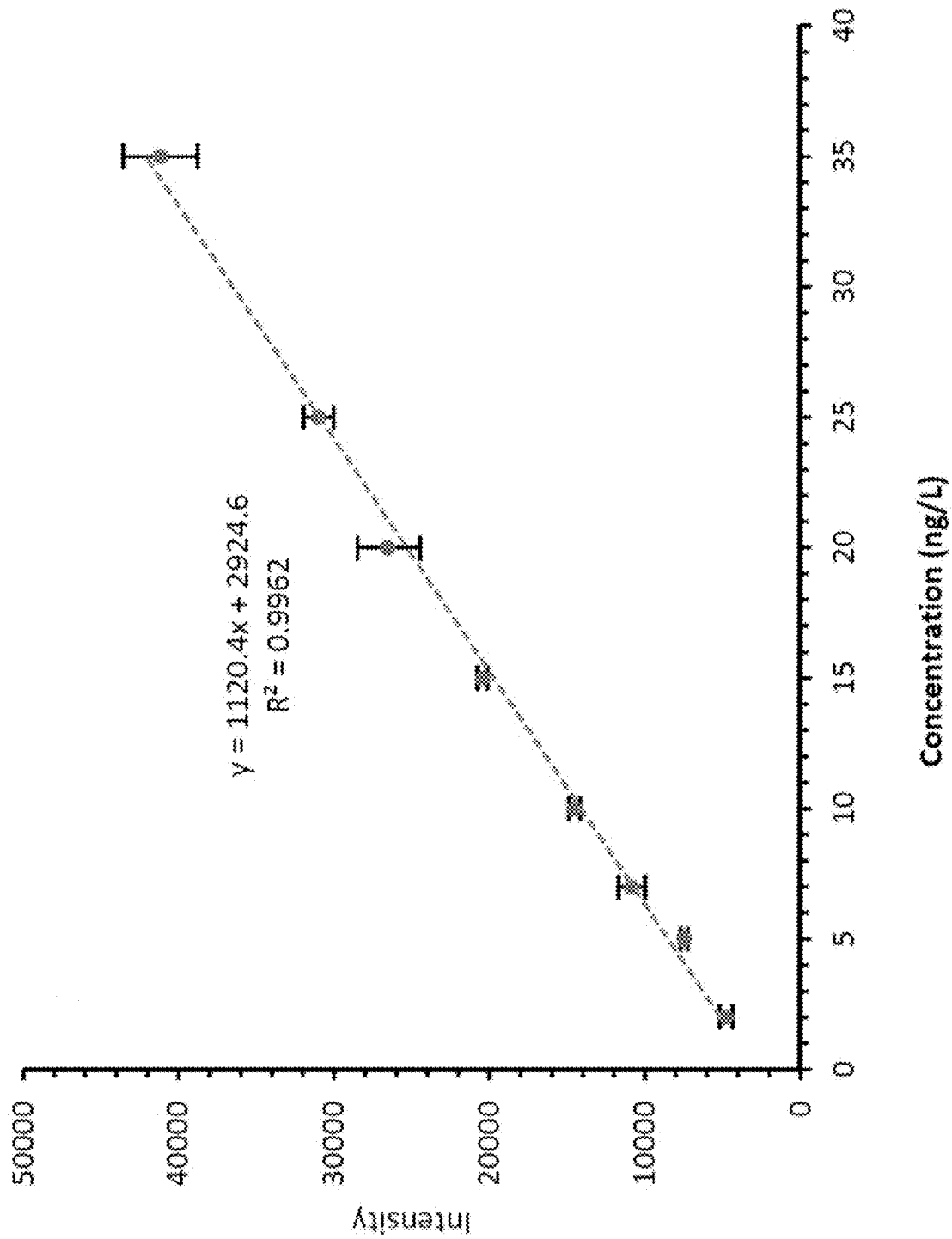
Figure 6A:
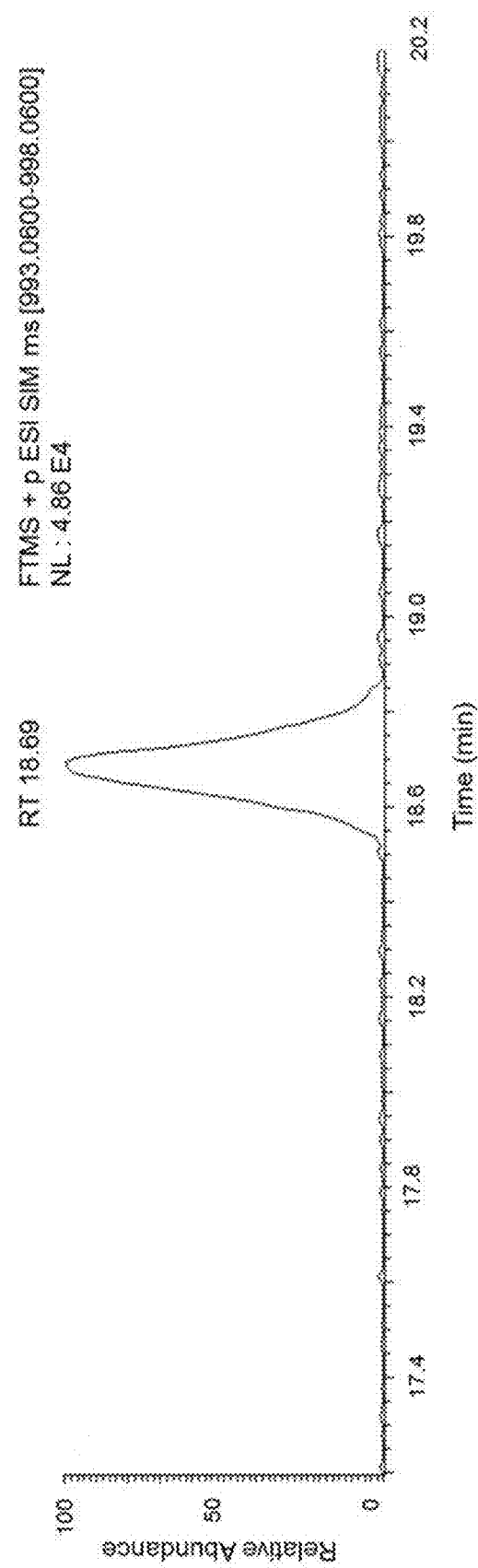
Figure 6B:
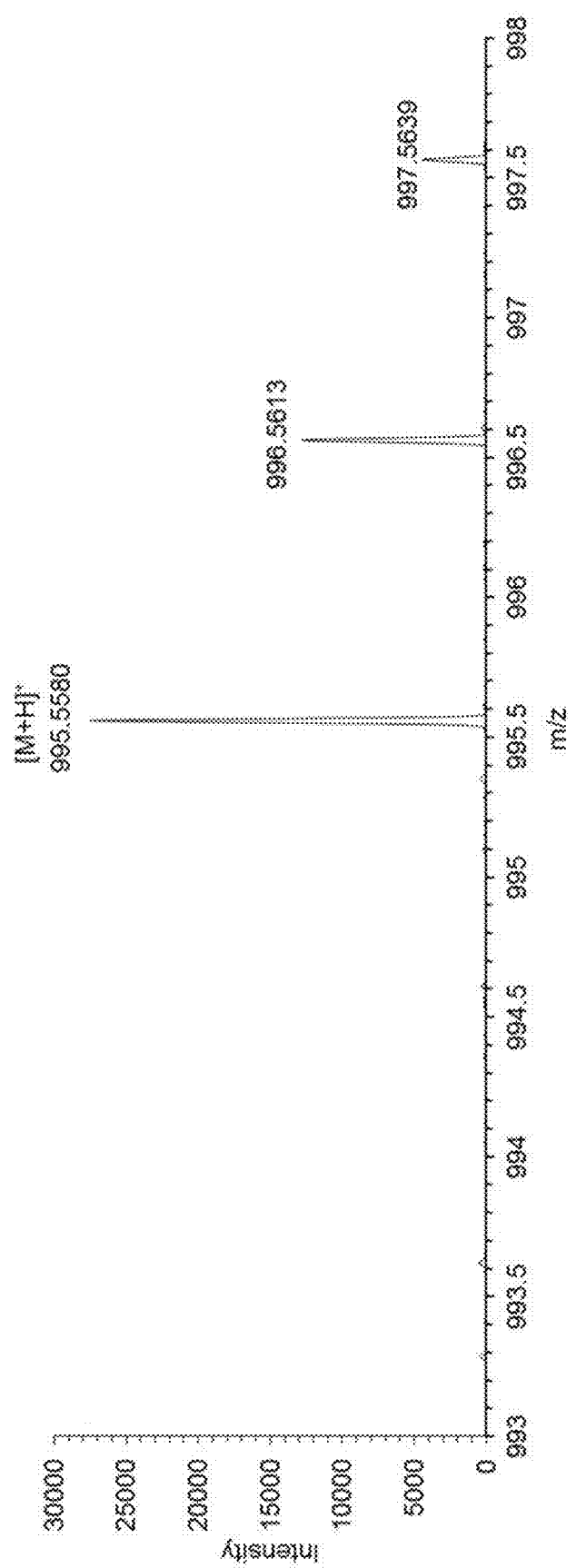

To apply the preconcentration method developed for quantification of low amounts of MC-LR in water, LC-SIM-MS calibration curves were constructed after the purification and preconcentration of the MC-LR samples (FIGS. 5A-5B). FIGS. 6A-6B show the EIC and mass spectrum of a 20 ng/L solution of MC-LR after 50x preconcentration. The concentration of MC-LR solution after preconcentration was ~1 µg/L, and LC-SIM-MS can be readily used to analyze such concentrations of MC-LR as demonstrated previously (FIGS. 2-3).

Figure 7A:
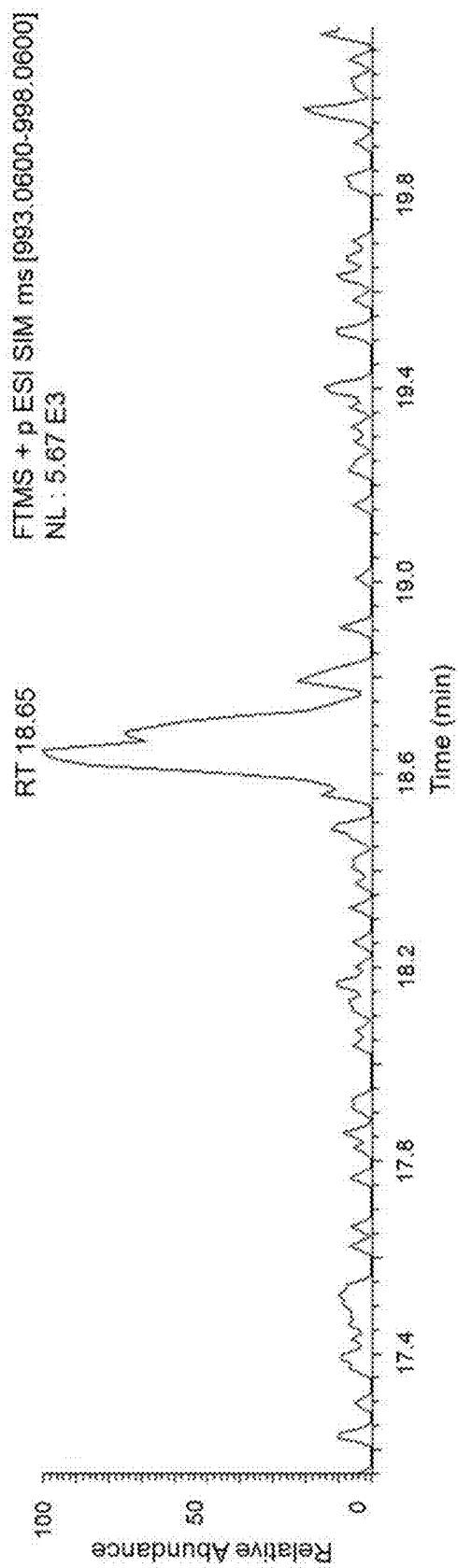
Figure 7B:
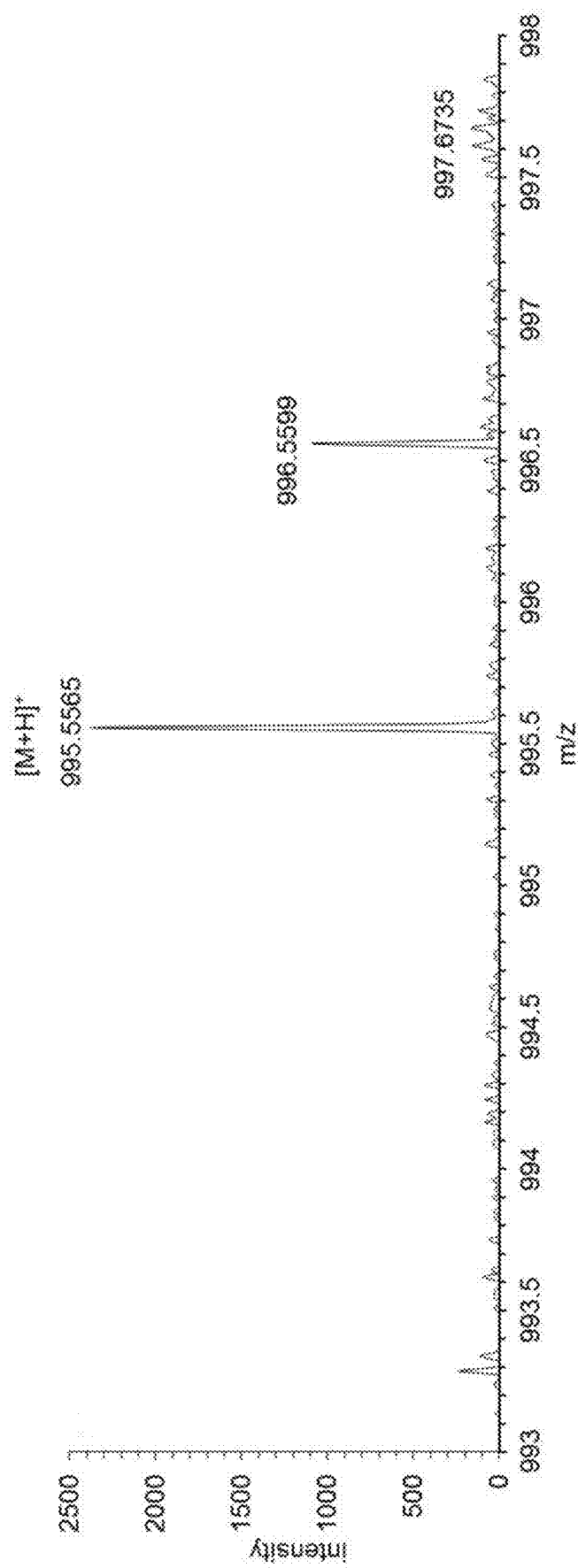

The calibration curve shown in FIG. 5A was obtained for SPE purified MC-LR samples in tap water for quantification of MC-LR in the concentration range between 500 pg/L and 35 ng/L. These concentrations are the initial concentrations of the sample before preconcentration, and the final concentration range after preconcentration was ~25 ng/L-1.75 µg/L. The calibration curve is linear with an $R^2$ value of 0.9987 over this concentration range. SPE purification and preconcentration of the samples prior to LC-SIM-MS analysis permitted detection of MC-LR in very dilute solutions (LOD~300 pg/L). FIGS. 7A-7B show the EIC and mass spectrum for the LOQ of MC-LR (500 pg/L) with preconcentration performed before analysis.

The calibration curve shown in FIG. 5A was validated using a blind standard (Table 2). After triplicate LC-SIM-MS analyses, it was calculated using this calibration curve that the concentration of MC-LR in the unknown samples were 22.77 ng/L (7.92% RSD) and 25.45 ng/L (2.21% RSD) while the actual concentrations were 22.50 ng/L and 25.00 ng/L, respectively. These results indicate that MC-LR can be accurately preconcentrated and quantified in tap water. Therefore, the calibration curve obtained by LC-SIM-MS after preconcentration of MC-LR samples can be used to quantify low (ng/L to pg/L) concentrations of MC-LR in tap water reliably.

Another calibration curve (FIG. 5B) was constructed for quantification of MC-LR in river water in the concentration range between 2 ng/L and 35 ng/L. The concentrations of MC-LR in the four spiked river water samples calculated using this calibration curve were 1.62 ng/L, 4.28 ng/L, 10.35 ng/L, and 20.76 ng/L (Table 3), showing ≤8.11% RSD in comparison to initial concentrations of MC-LR. The LOD of MC-LR in the spiked river water samples was 500 pg/L while MC-LR LOQ was 2.00 ng/L. An increase of MC-LR LOQ in river water in comparison to tap water indicates the suppression of MC-LR ionization at low concentration levels in river water. Without wishing to be bound by theory, it is believed that this may be due to the matrix effects from the other components present in river water samples. Nevertheless, low concentrations of MC-LR were accurately and reproducibly quantified in river water samples.

The validation experiments demonstrate that the developed SPE and LC-ESI-SIM-MS methods can be used for the quantification of MC-LR in complex samples, such as tap and river water.

Validation of Calibration Curves Using Complex MC-LR Samples

Calibration curves shown in FIG. 3 and FIGS. 5A-5B were then applied to quantify MC-LR in more complex samples. Initially, MC-LR was spiked in tap water to prepare a 25.00 ng/L solution of MC-LR, which was then purified by SPE and preconcentrated. Using LC-SIM-MS and the calibration curve in FIG. 5A, it was determined that the concentration of MC-LR in tap water was 25.45 ng/L (2.21% RSD). This result indicates that MC-LR can be accurately preconcentrated and quantified in tap water.

Figure 8:
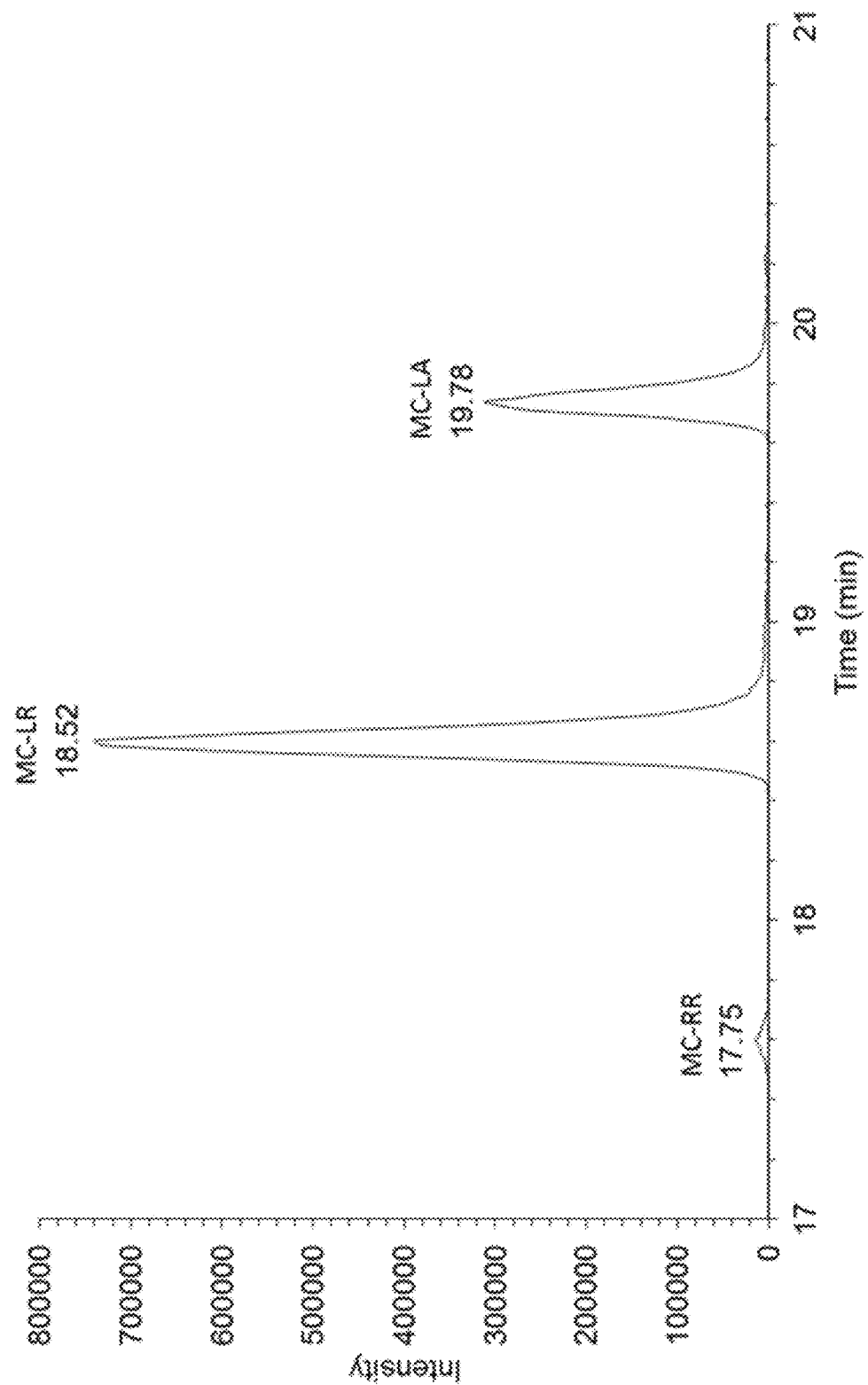
Figure 9A:
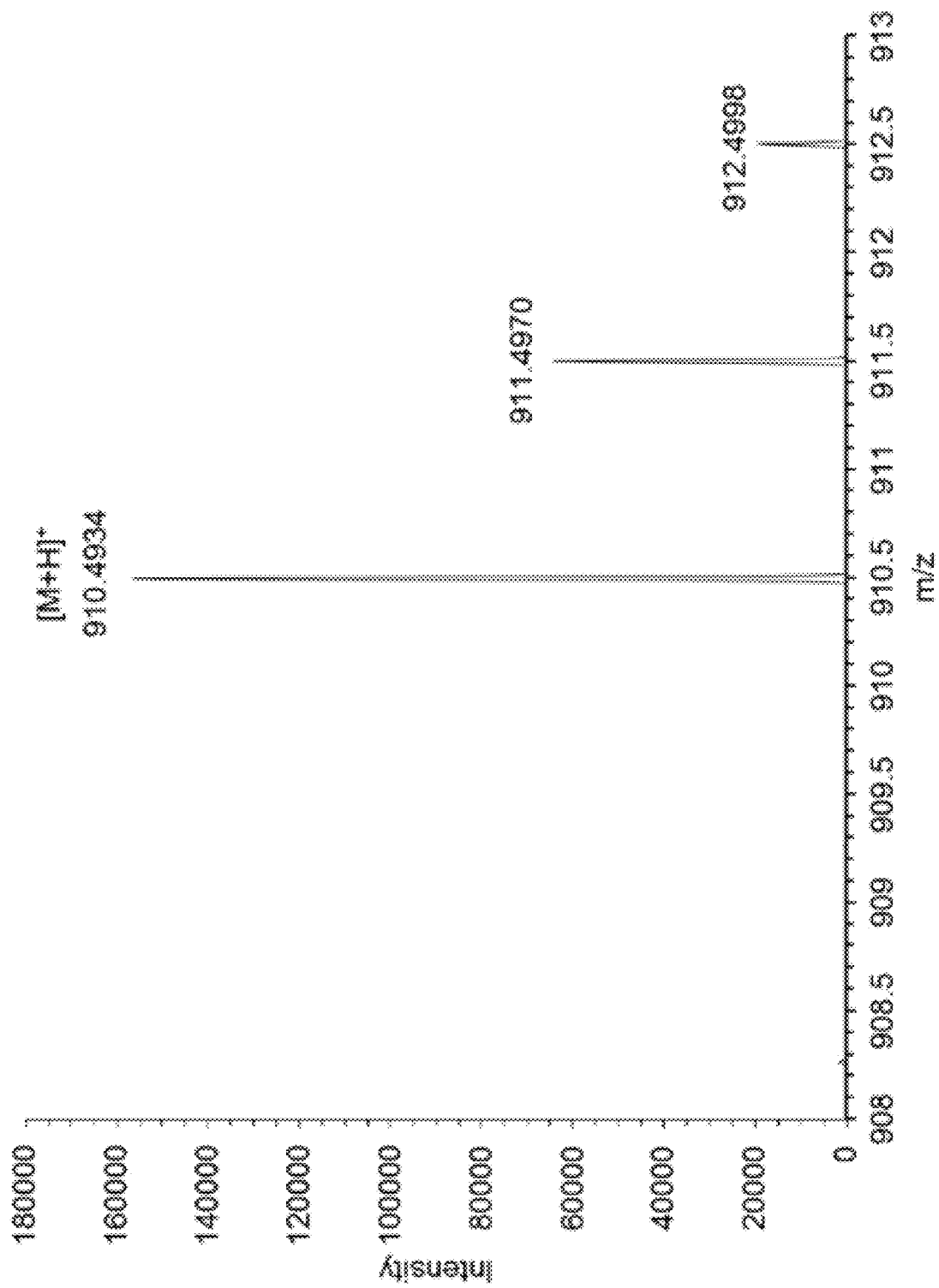
Figure 9B:
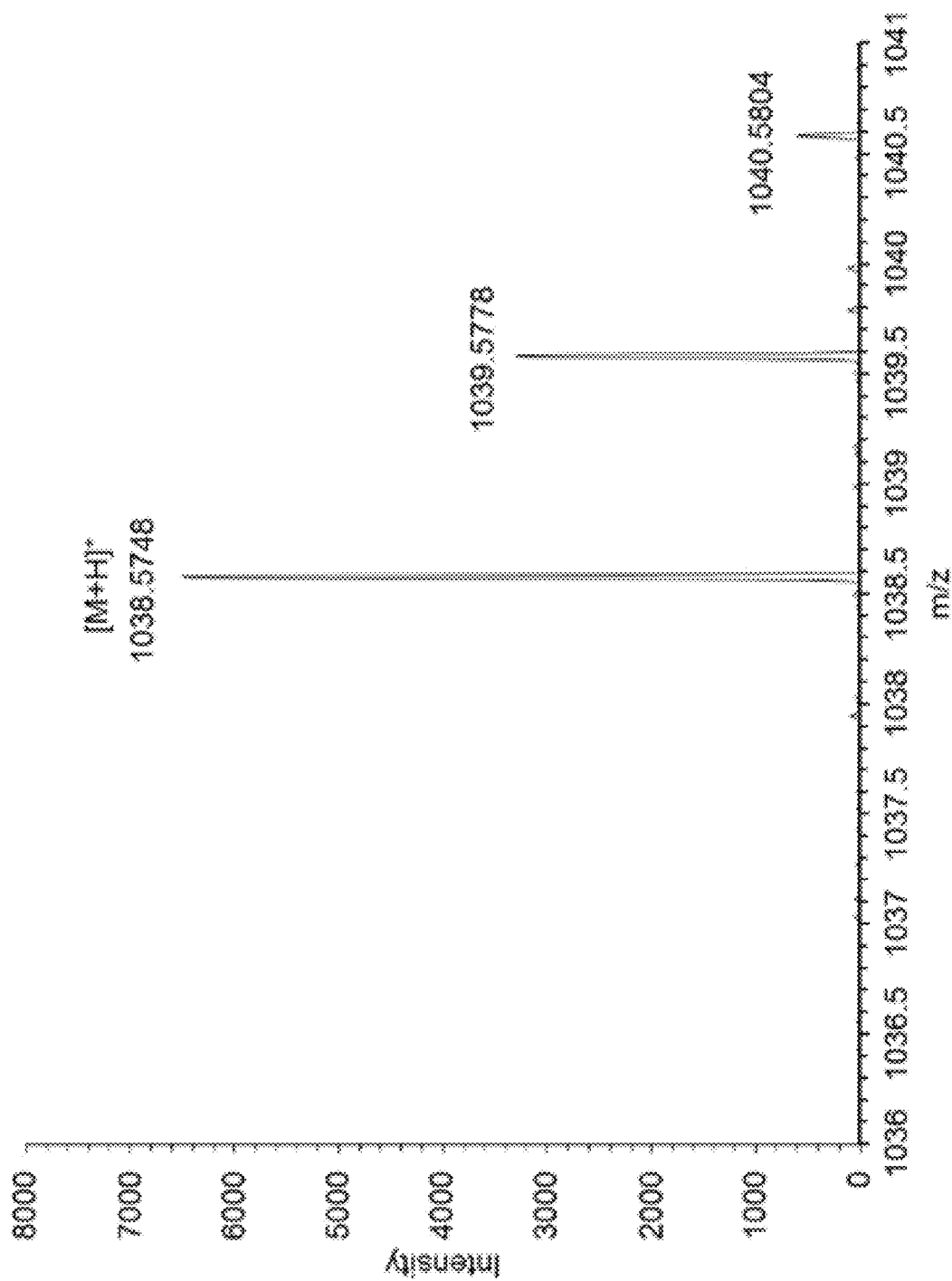

Next, the 10 µg/L solutions of MC-LR, MC-RR, and MC-LA were analyzed individually using LC-SIM-MS of their singly-charged ions whose m/z values are shown in Table 1. FIG. 8 shows the overlaid EICs for MC-RR ($t_R$=17.72 min), MC-LR ($t_R$=18.52 min), and MC-LA ($t_R$=19.78 min). FIGS. 9A-9B shows mass spectra of MC-LA and MC-RR, and m/z values of their singly charged ions were measured with excellent mass accuracies that are <2 ppm (Table 1). Quantification of MC-LR was then performed in a mixture containing 1 µg/L of MC-LR, 1 µg/L of MC-LA, and 10 µg/L MC-RR. The concentration of MC-RR in this solution was higher than the concentration of other MCs due to the low MS peak intensity of its singly charged ion (m/z 1038.5748) at 1 µg/L. Since pure stock solutions of MCs were used for preparation of the mixture, sample purification using SPE was not necessary before the LC-SIM MS analysis. The concentration of MC-LR in the mixture with other MCs was measured using LC-SIM-MS of MC-LR ion with m/z 995.56 and the calibration curve in FIG. 3 was 0.97 µg/L (Table 2), showing 2.18% RSD in comparison to initial concentration of MC-LR (1.00 µg/L). This demonstrated that the developed LC-ESI-SIM-MS method can be used for the quantification of MC-LR in the presence of other MCs without matrix effects occurring.

Quantification of MC-LR Using LC-MS/MS

Figure 10A:
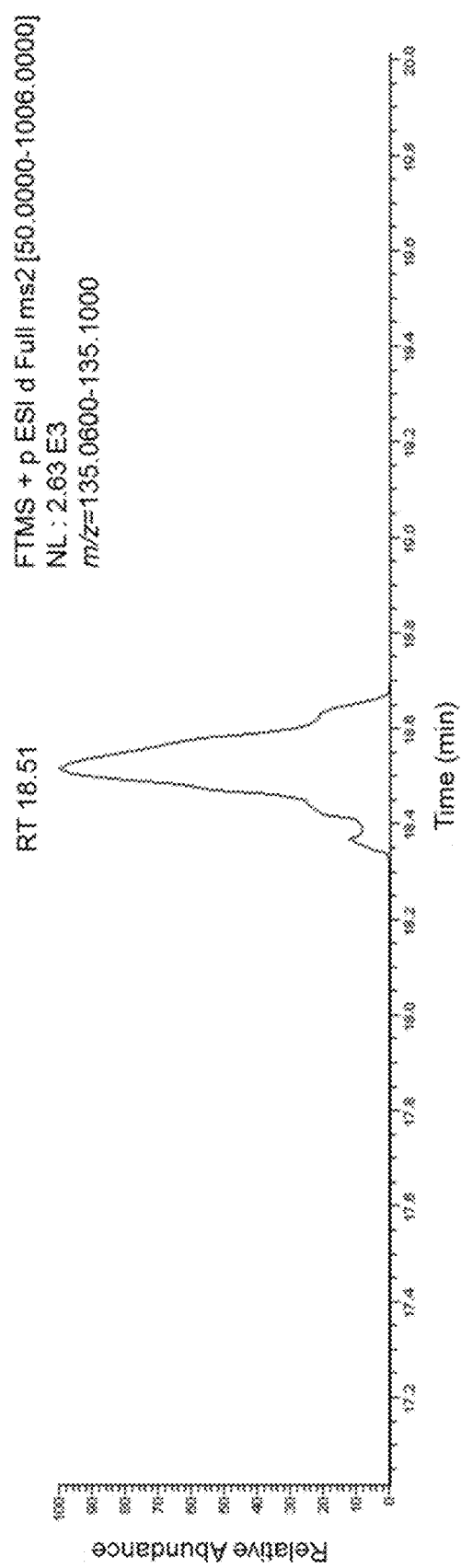
Figure 10B:
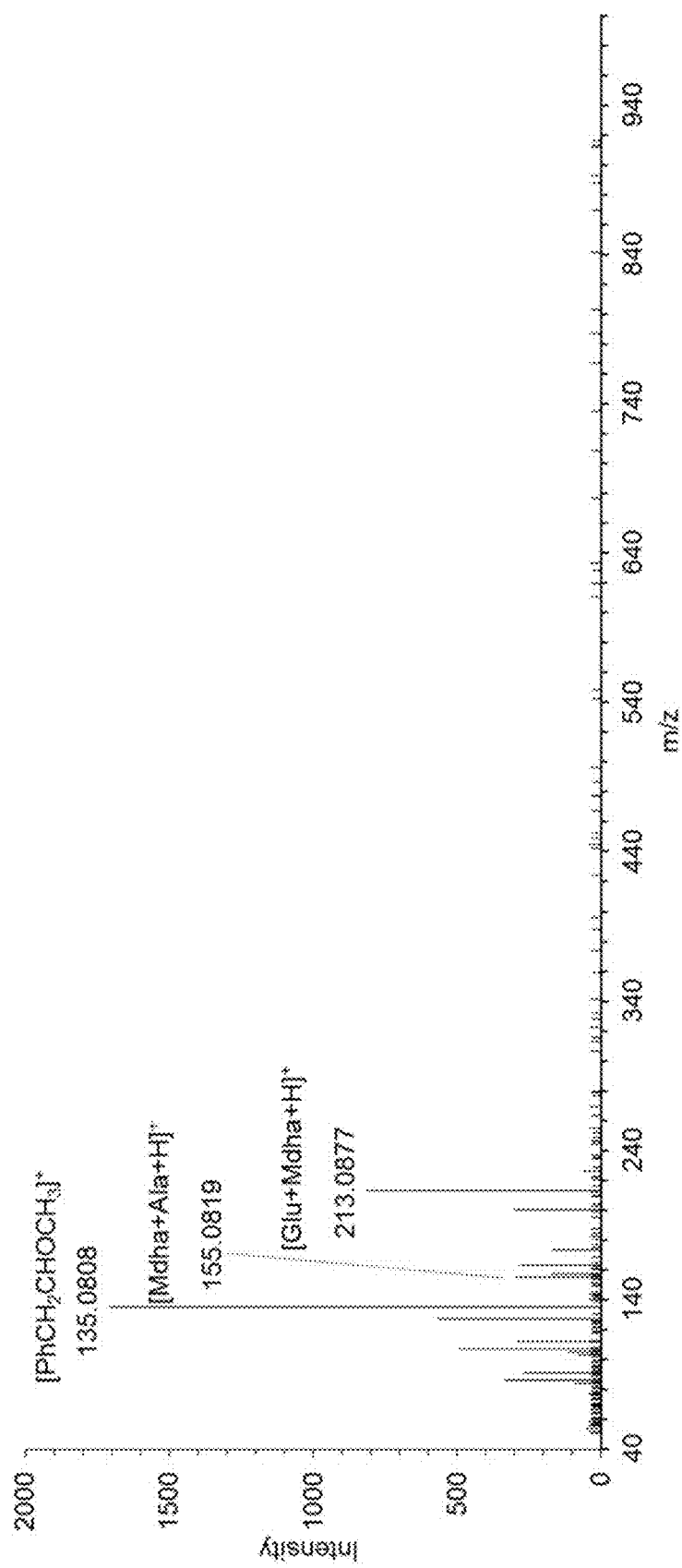
Figure 11:
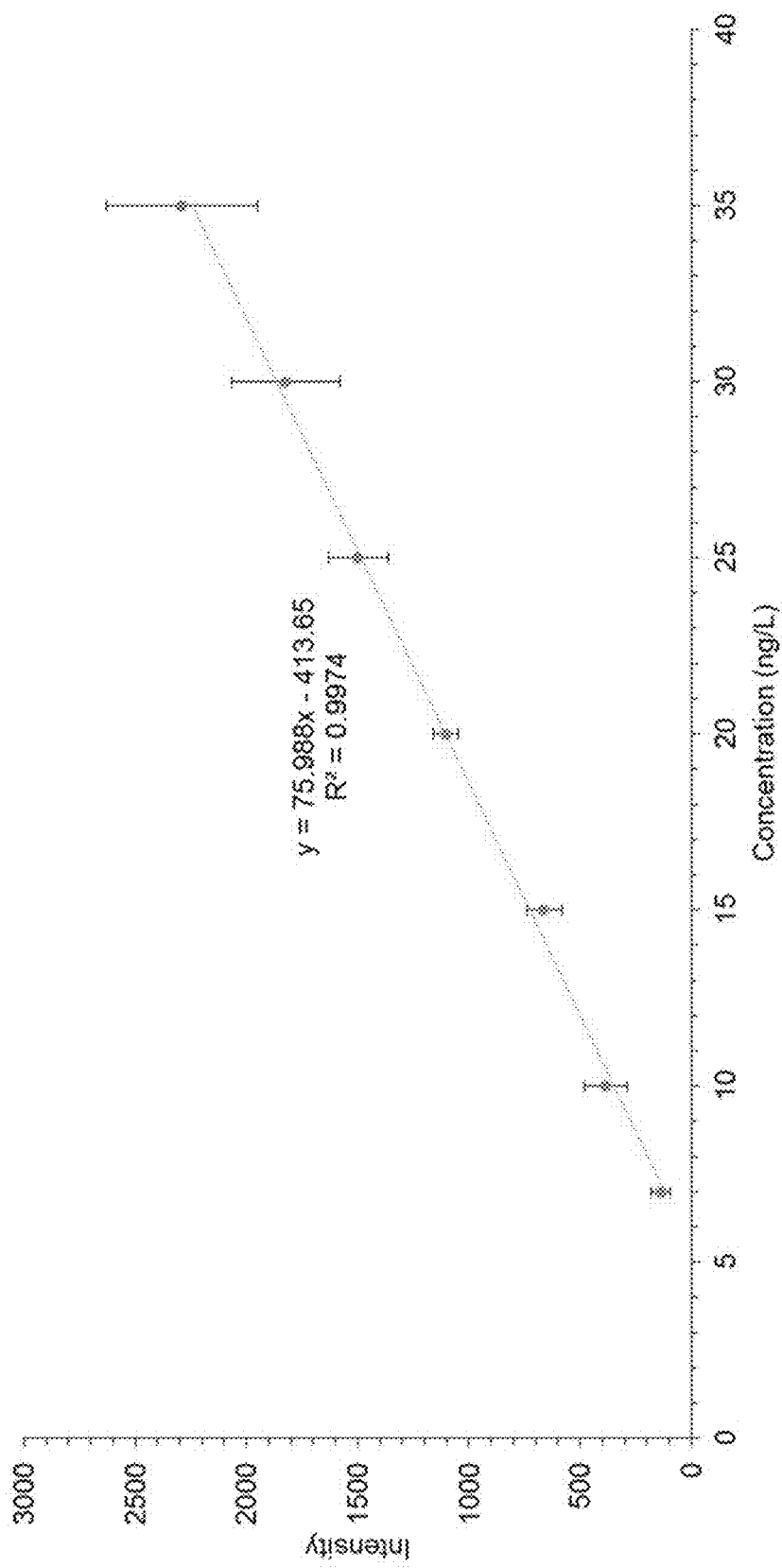

Since the Orbitrap Fusion MS can select ions using SIM and analyze their fragments by MS/MS, the quantification of MC-LR was also performed using LC-MS/MS. Initially, LC-MS/MS was used to analyze aqueous solutions of MC-LR that were not preconcentrated. FIG. 10 shows the EIC of MC-LR fragment ion with m/z 135.0808 and MS/MS spectrum of precursor MC-LR ion (m/z 995.5587) obtained using HCD. The ESI-MS/MS intensities of the MC-LR fragment ion with m/z 135.0808 were determined for standard solutions of MC-LR, and used to construct the LC-MS/MS calibration curve shown in FIG. 11. This calibration curve showed excellent linearity ($R^2$=0.9999) over the concentration range 200 ng/L-10 µg/L. The LOD of MC-LR using LC-MS/MS was ~100 ng/L, and the LOQ of MC-LR was determined to be 200 ng/L. The LOQ of MC-LR using LC-MS/MS is higher than the LOQ measured using LC-SIM-MS (25 ng/L). However, LC-MS/MS is useful for structural characterization and identification of MC variants, and can avoid potential isobaric interferences during the quantification of MC-LR.

Figure 12:
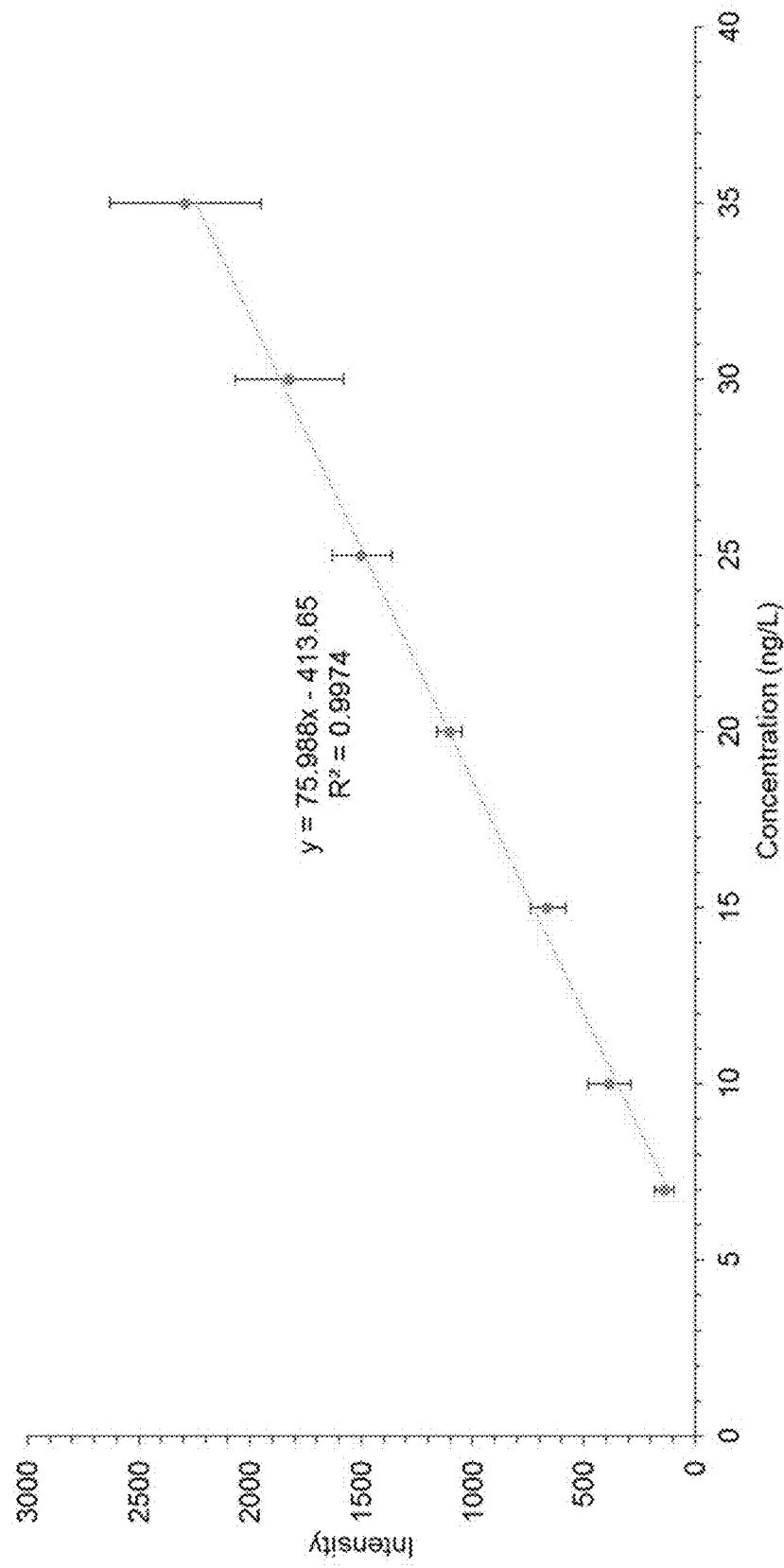

FIG. 12 shows the calibration curve constructed using LC-MS/MS for MC-LR solutions with concentrations between 7 ng/L and 35 ng/L, which were preconcentrated 50× yielding final concentration of the standards from ~350 ng/L to ~1.75 µg/L. The calibration curve is linear ($R^2$=0.9974), with a LOQ of 7 ng/L. The LOD of MC-LR using sample preconcentration and LC-MS/MS was ~5 ng/L. The LOQ of MC-LR using LC-MS/MS to analyze preconcentrated MC-LR samples was higher than the LOQ measured using LC-SIM-MS (500 pg/L). LC-SIM-MS was more sensitive for the quantification of low-concentration MC-LR samples than LC-MS/MS. However, the Orbitrap Fusion Tribrid MS can quantify MC-LR at the concentrations that are lower than the maximum concentration of total MCs in drinking water advised by EPA (≤0.3 µg/L) by both LC-SIM-MS and LC-MS/MS. The LOQ of MC-LR by LC-MS/MS may be improved by using LIT instead of orbitrap for quantification. Additional optimizations of HPLC separation conditions and MS acquisition methods may help improving LOQs of MC-LR by both LC-MS and LC-MS/MS further.

A Comparison of Present MC-LR Quantification Results with Literature Data

Due to the differences in the sample complexities as well as the instruments and data processing methods used, it is not straightforward to accurately compare the figures of merit (e.g., LOQs, LODs, and SPE recoveries) of the present methods to those reported previously for the quantification of MC-LR. The present example demonstrates that an HPLC-Orbitrap Fusion MS system provides excellent LOQ and LOD of MC-LR with and without sample preconcentration. Table 6 (FIG. 20) shows a comparison of SPE percent recoveries, LODs and LOQs of MC-LR obtained by different LC-ESI-MS and LC-ESI-MS/MS methods, where the circled methods and the results are from the examples herein. Note that most of the LOD and LOQ values in Table 6 are shown in µg/L (ppb), while some are shown in ng/L (ppt).

Additionally, the present SPE purification method exhibits excellent recovery of MC-LR. The MC-LR preconcentration method described in this example is applicable for detection and quantification of MC-LR by LC-MS (or other techniques) in drinking water and more complex, environmental water samples. Importantly, LC-SIM-MS and high-mass accuracy capabilities of an orbitrap mass spectrometer are useful for the targeted quantitative analyses of microcystins. The HPLC-Orbitrap Fusion MS system can also be applied for qualitative and quantitative analyses of multiple microcystins in the full scan mode.

Conclusion

Reproducible and sensitive LC-ESI-SIM-MS and LC-ESI-MS/MS methodologies based on external calibration were developed for the quantification of MC-LR in aqueous solutions, tap water, and a mixture with MC-LA and MC-RR using an HPLC-Orbitrap Fusion MS System. The described sample purification and preconcentration method based on SPE reproducibly and accurately recovered MC-LR from aqueous solutions and tap water for consequent quantitative analyses. MC-LR was detected and quantified using LC-ESI-SIM-MS at high-pg/L and low-ng/L concentrations with and without preconcentration before the analyses, respectively. The LC-ESI-MS/MS method also enabled quantification of MC-LR in the ng/L concentration range. Based on the present results, HPLC-Orbitrap Fusion MS system and preconcentration method developed is useful for efficient LC-MS and LC-MS/MS qualitative and quantitative analyses of MC-LR and other microcystins in water.

Example 2—HPLC Method for the Separation of MCs

A method was developed to separate multiple microcystins in a mixture. FIGS. 13A-13B show the solvent parameters and conditions for the HPLC method utilized in this example, where the solvents were acetonitrile in Pump B and 0.1% formic acid in Pump A.

Figure 14:
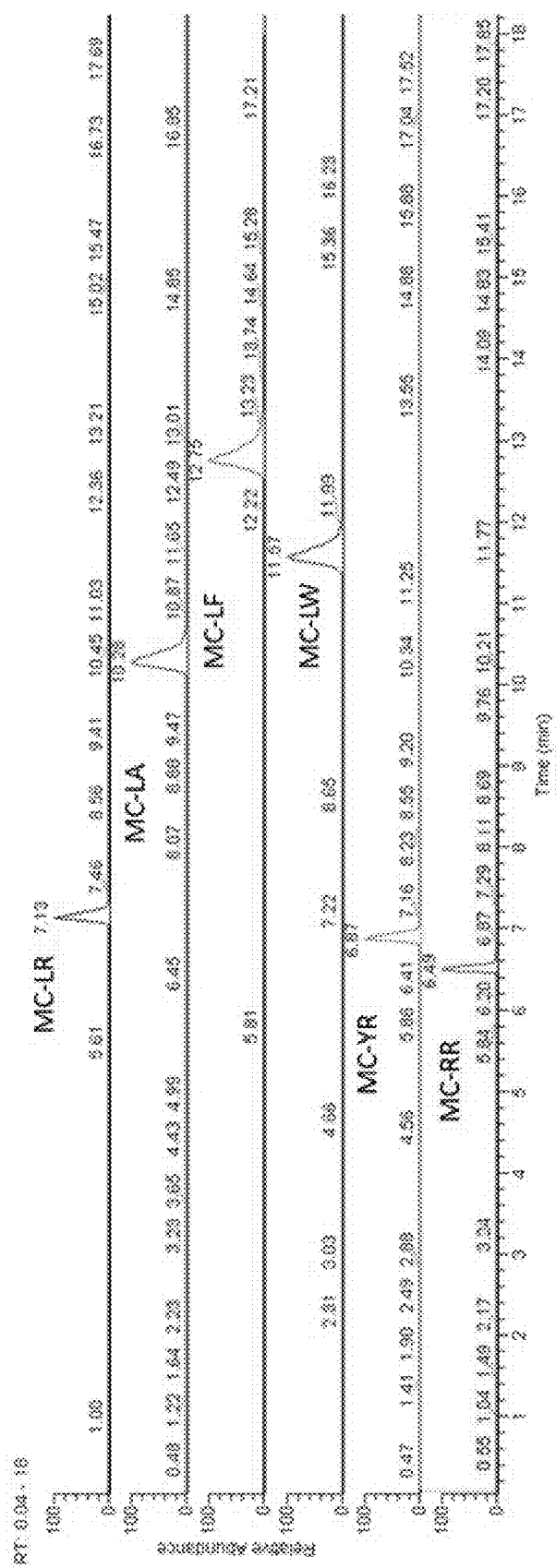
Figure 15A:
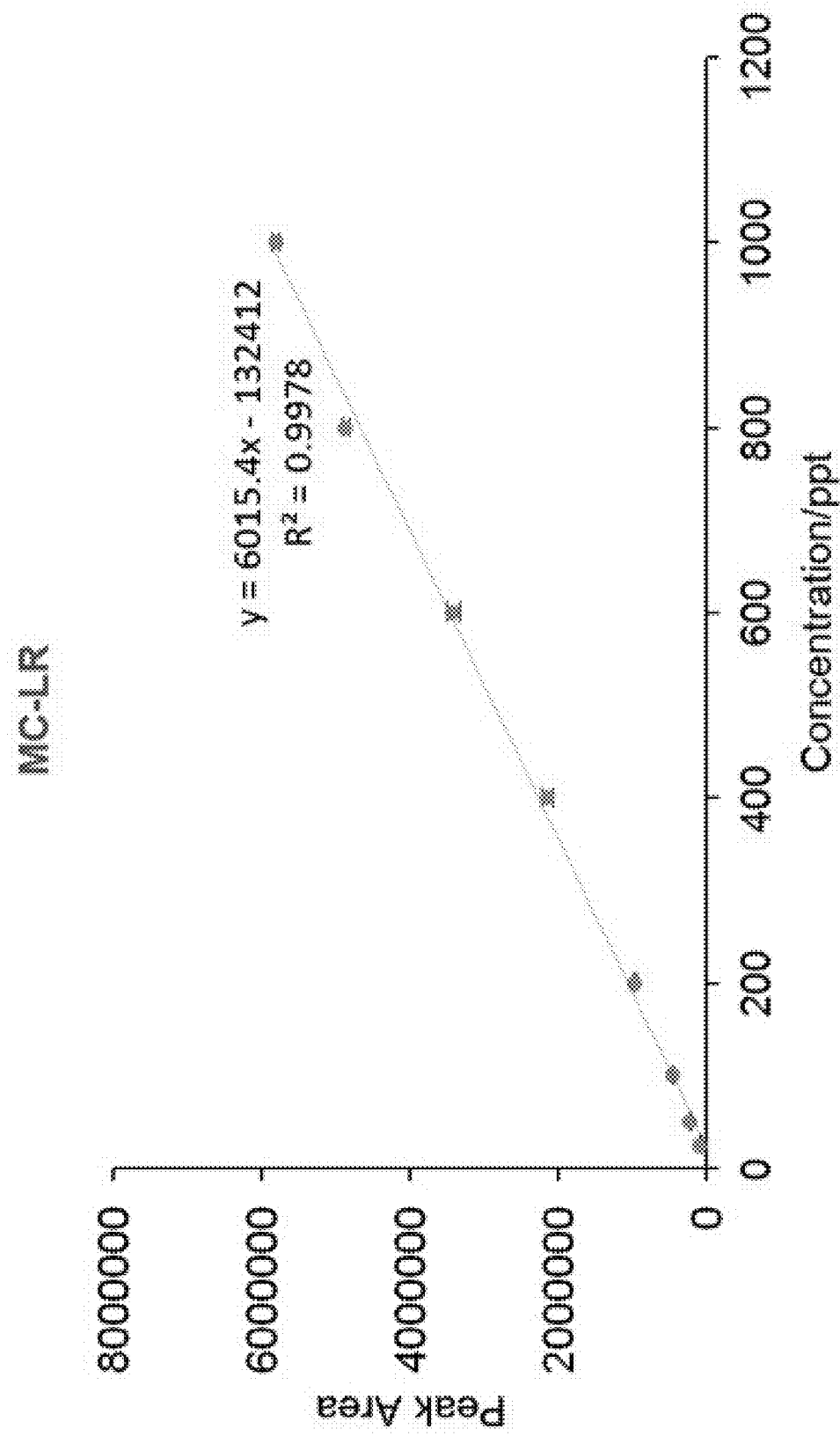
Figure 15B:
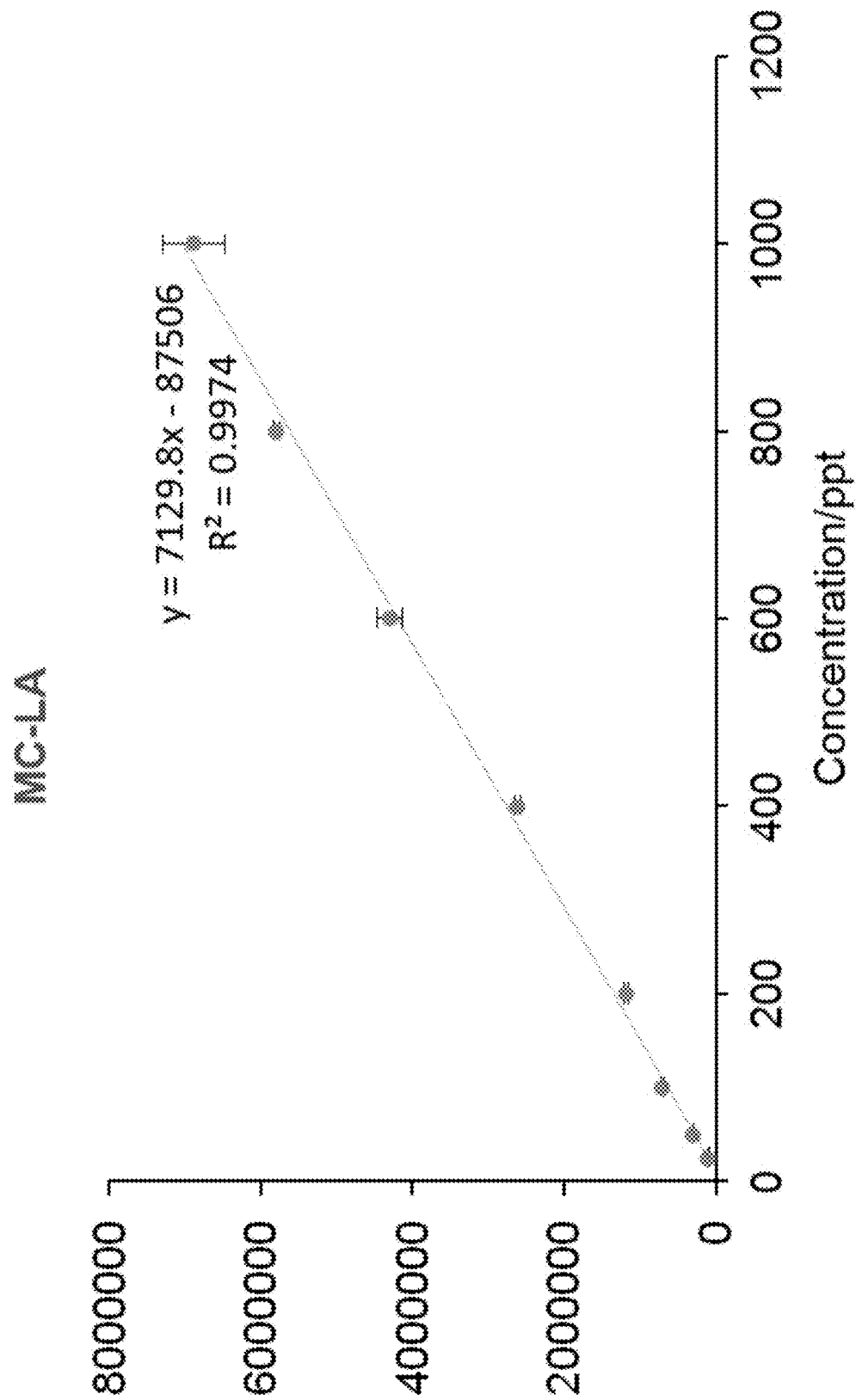
Figure 15C:
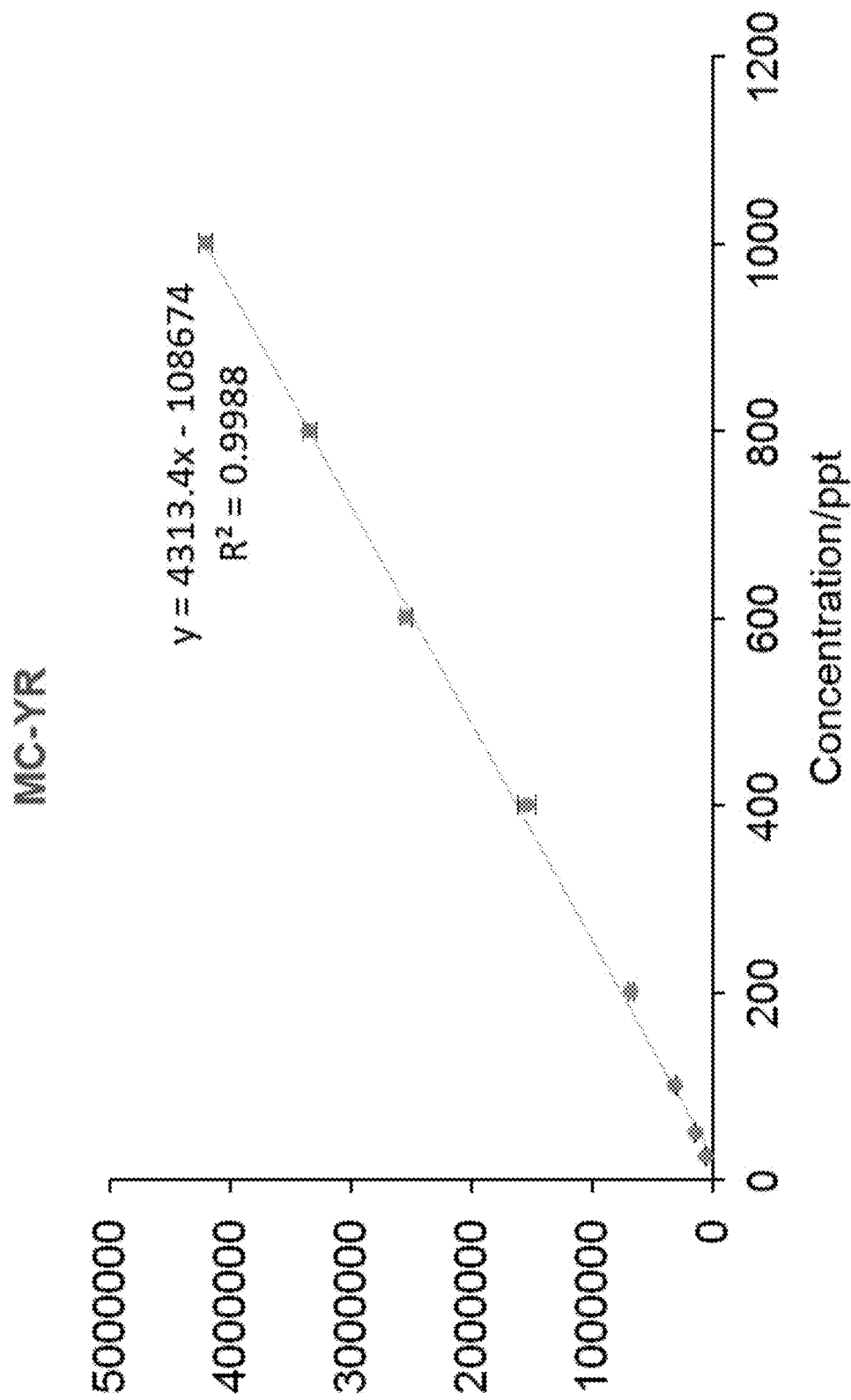
Figure 15D:
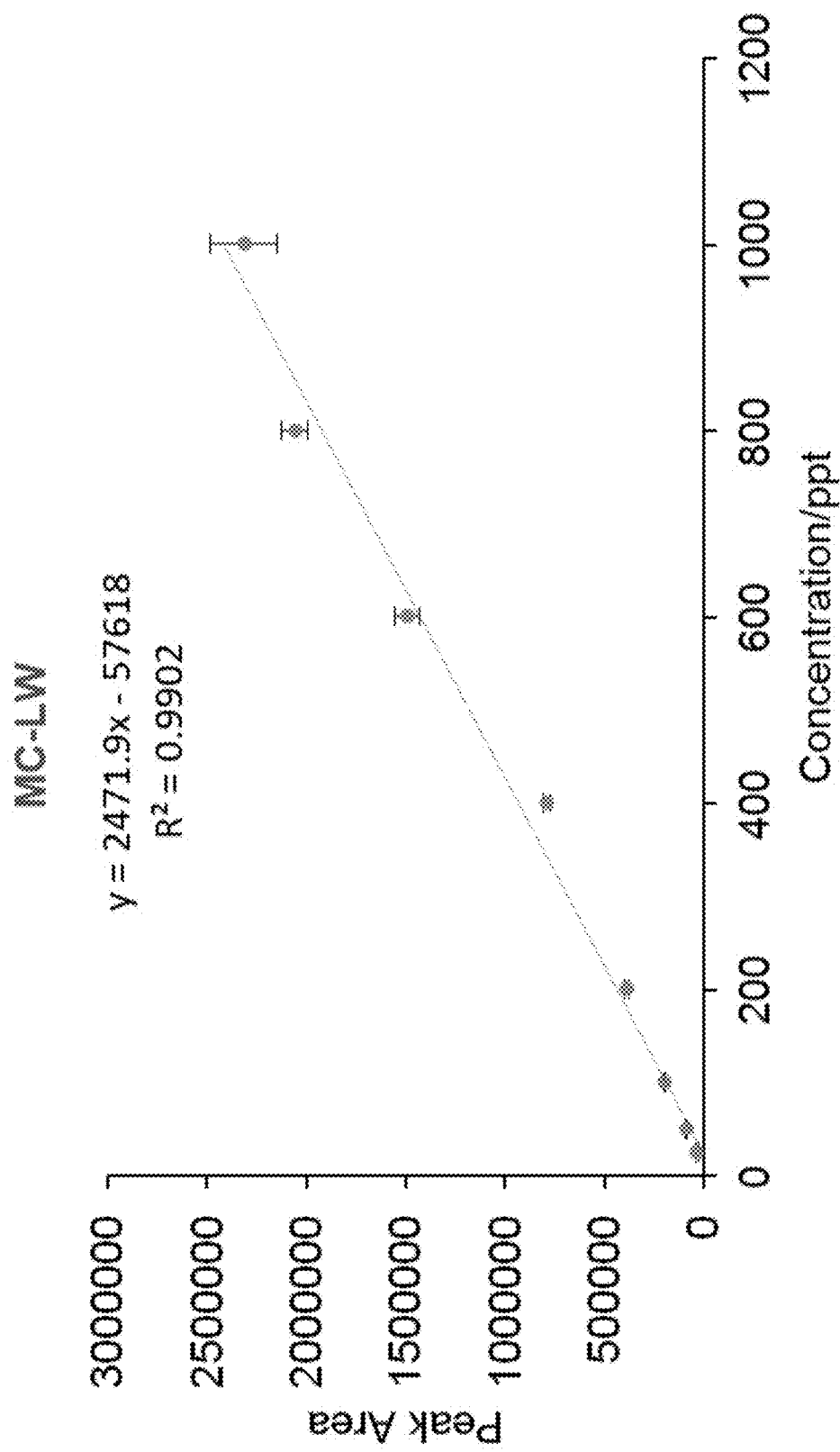
Figure 15E:
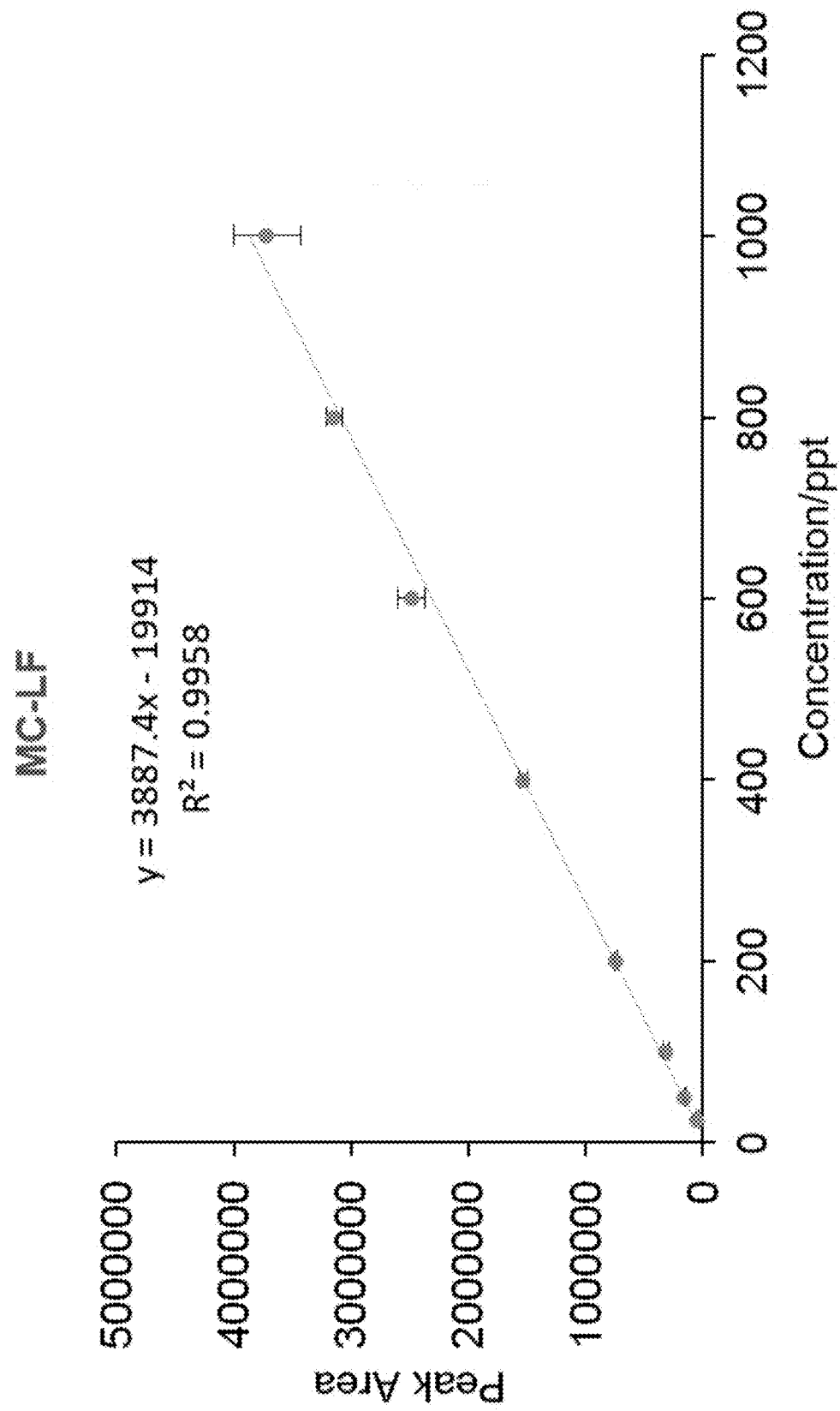
Figure 15F:
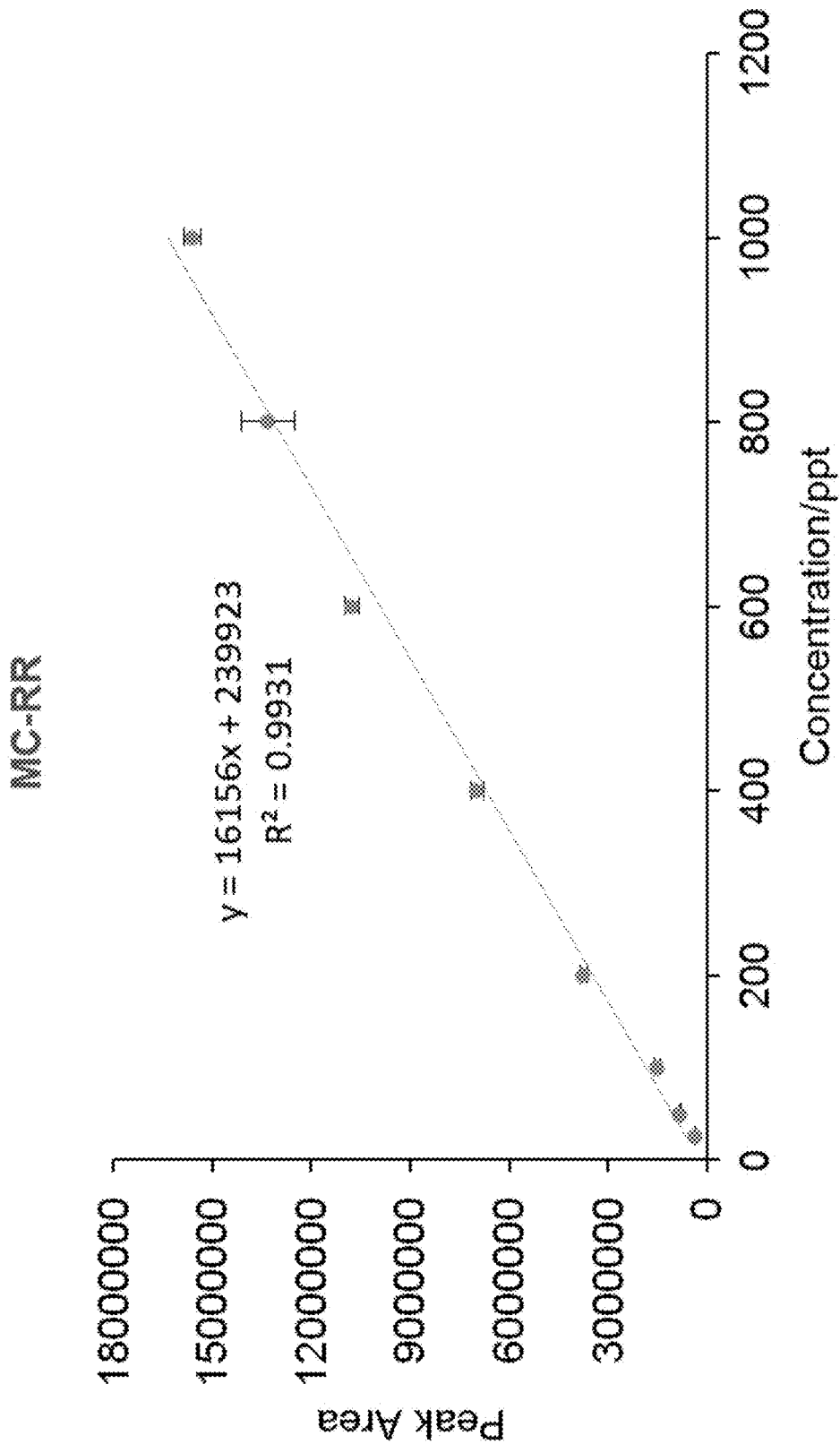
Figure 17A:
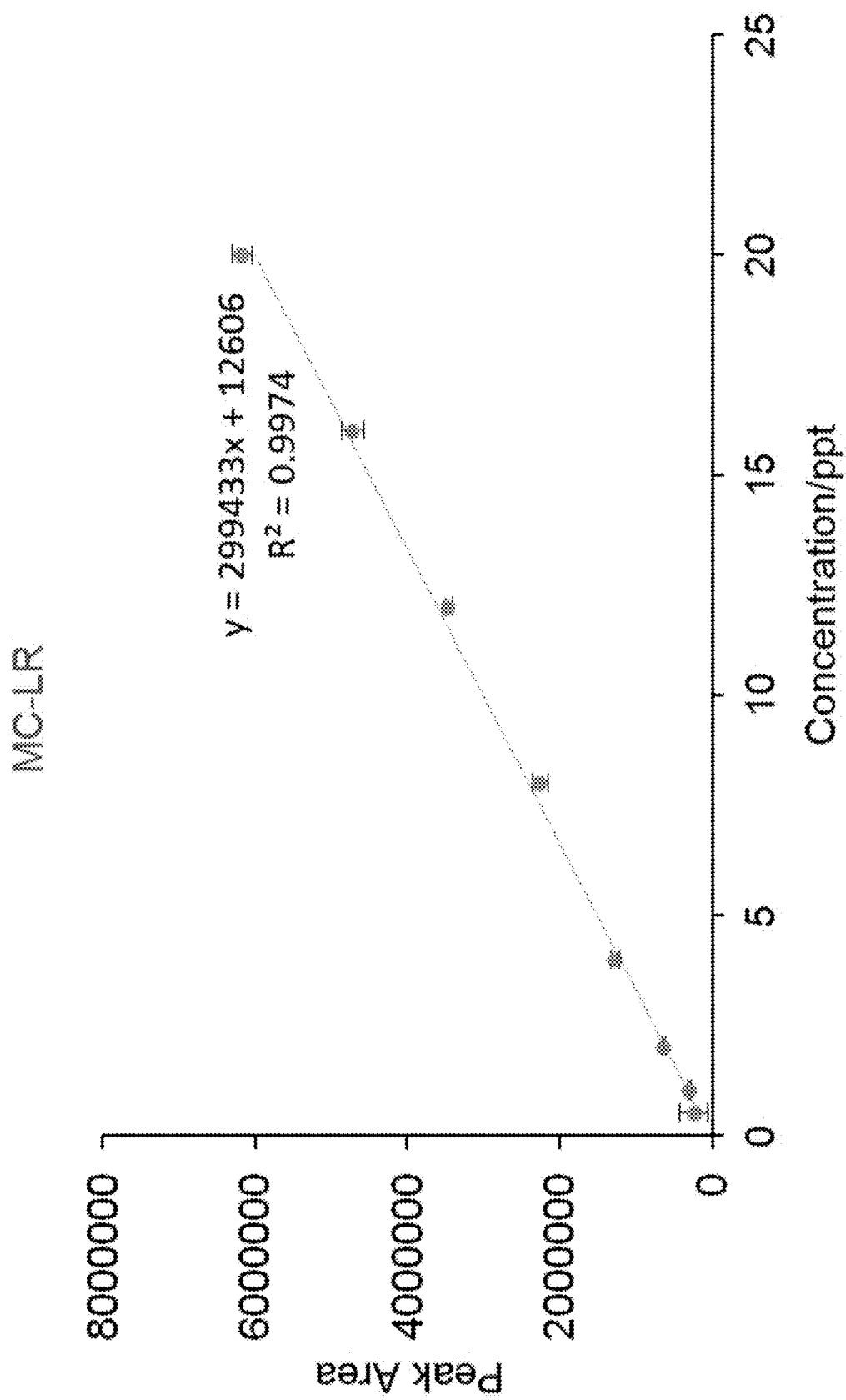
Figure 17B:
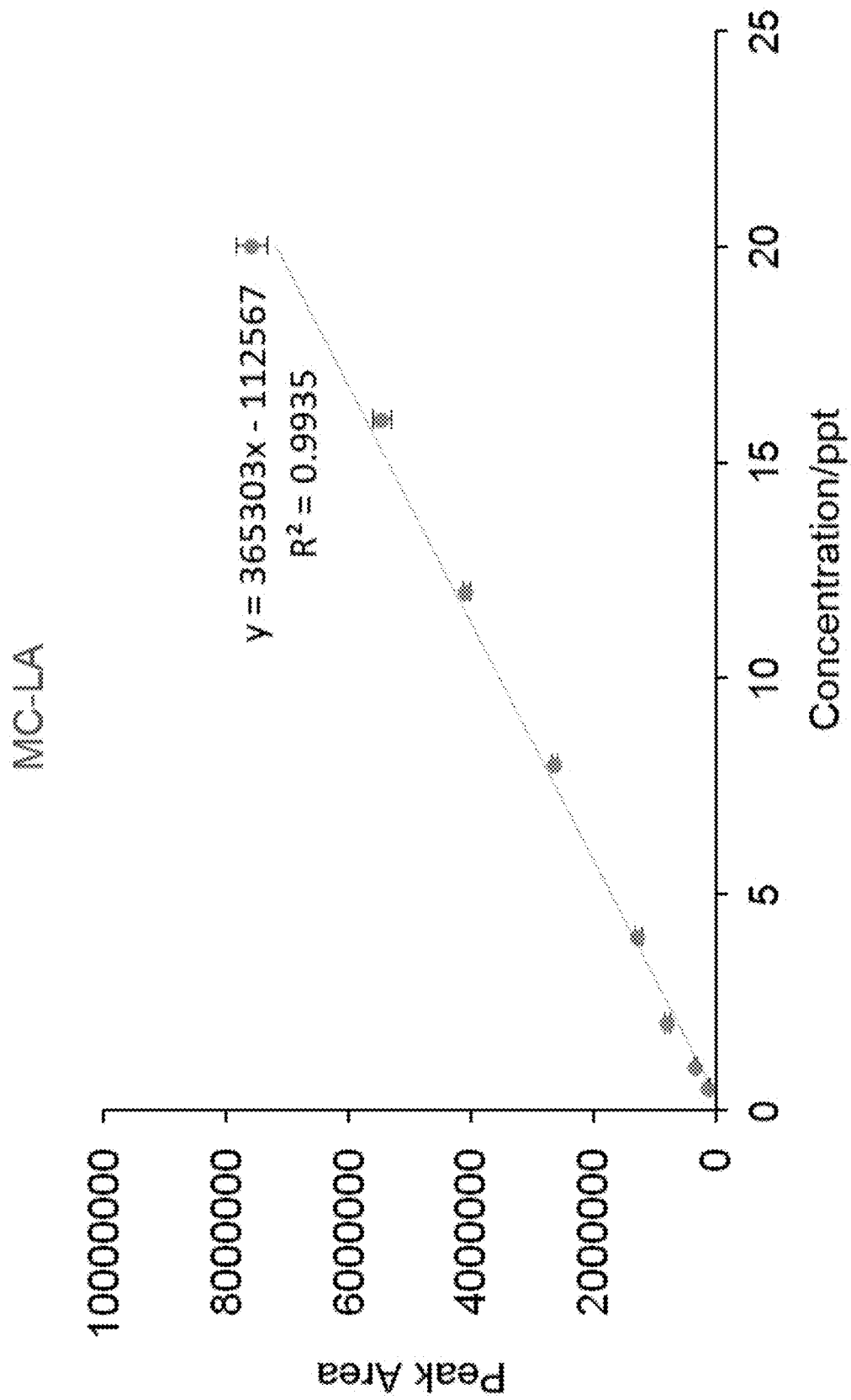
Figure 17C:
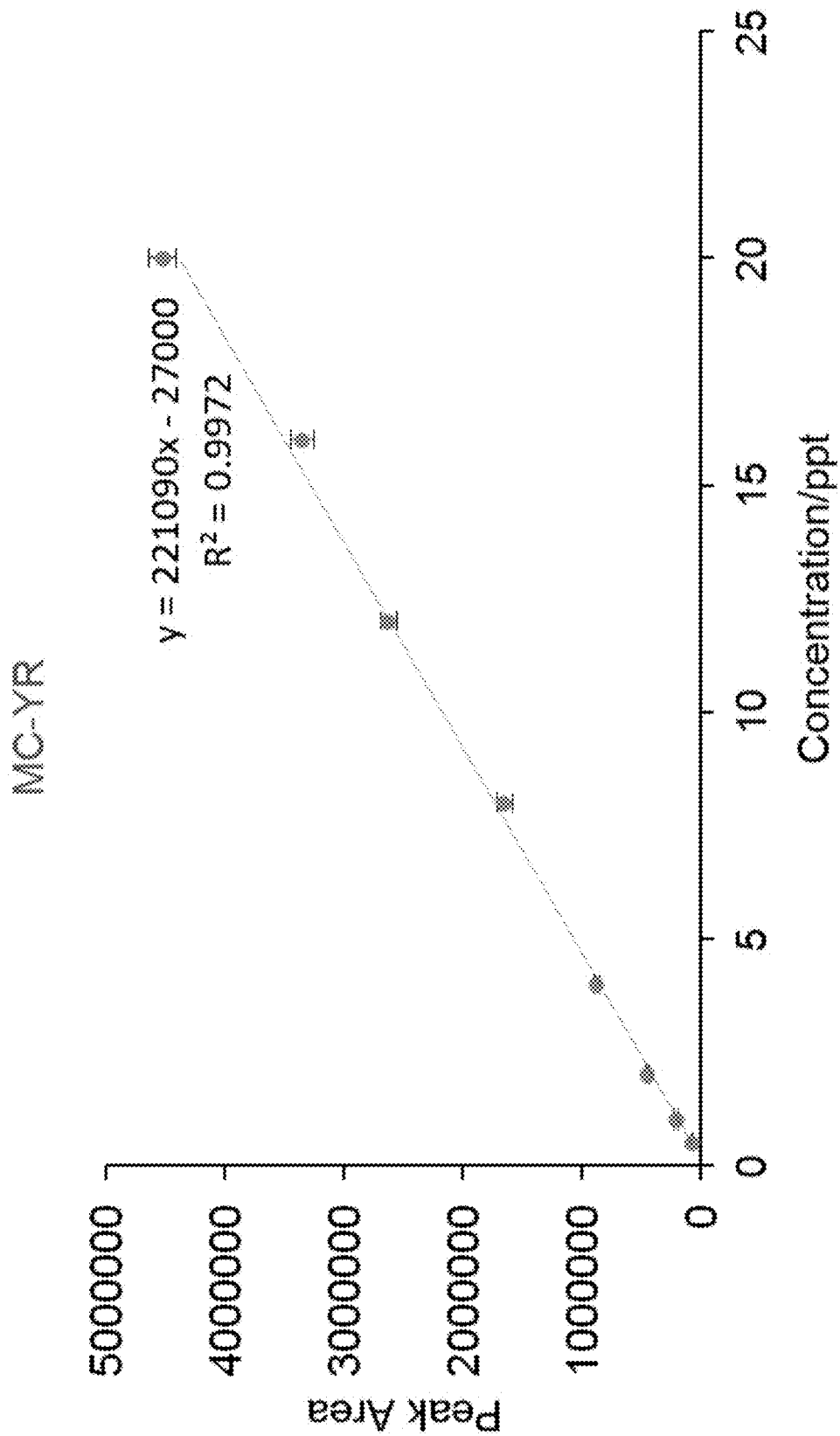
Figure 17D:
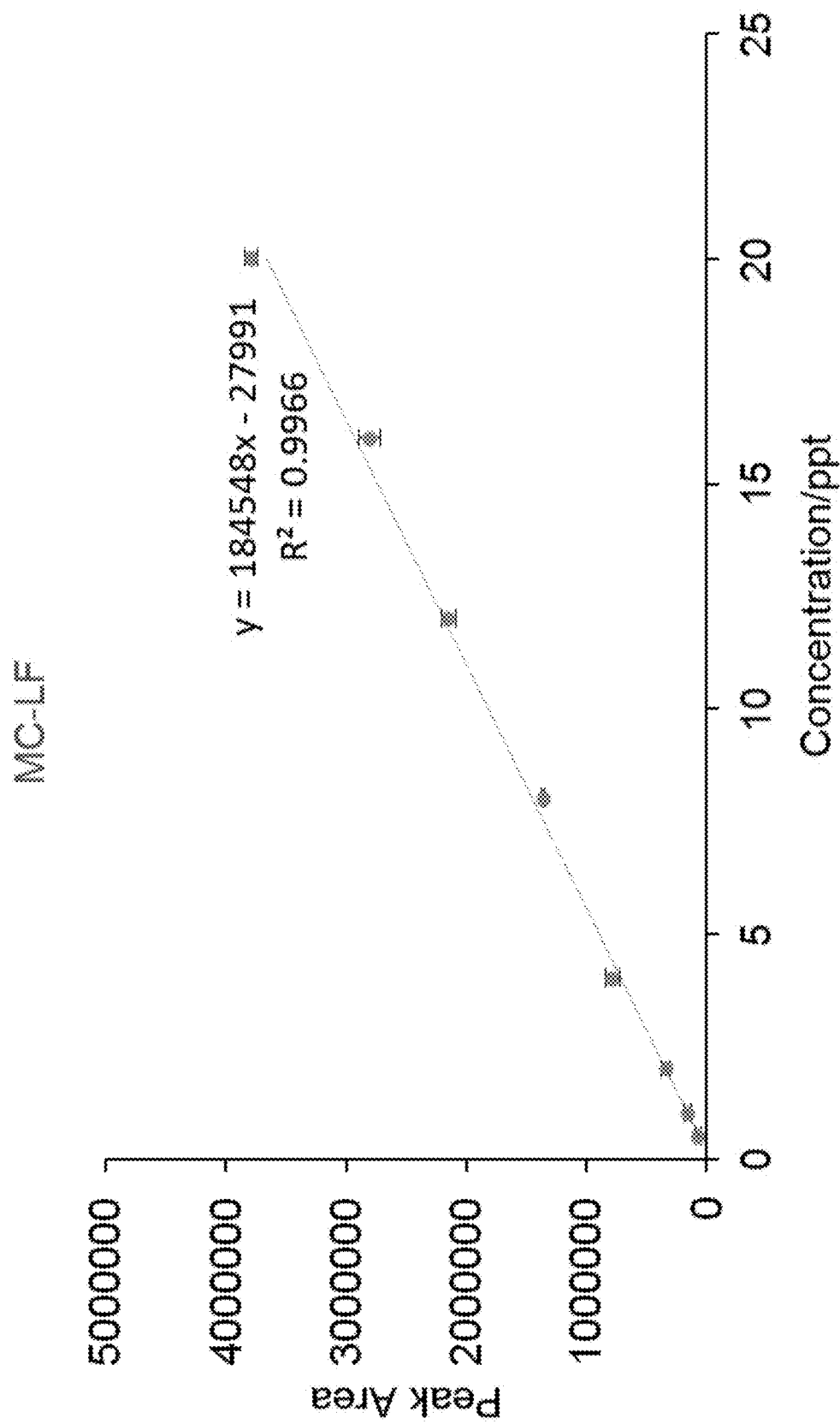
Figure 17E:
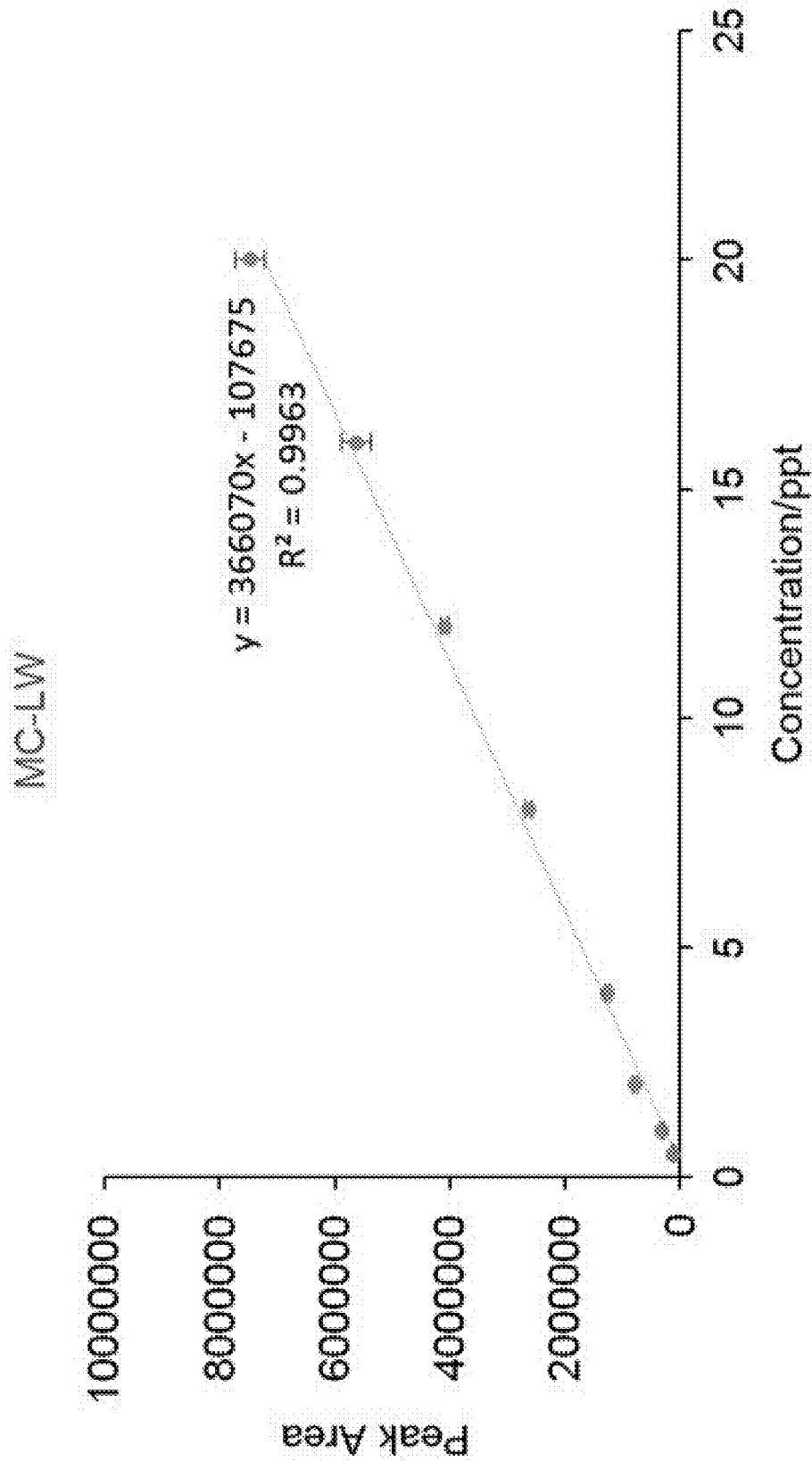
Figure 17F:
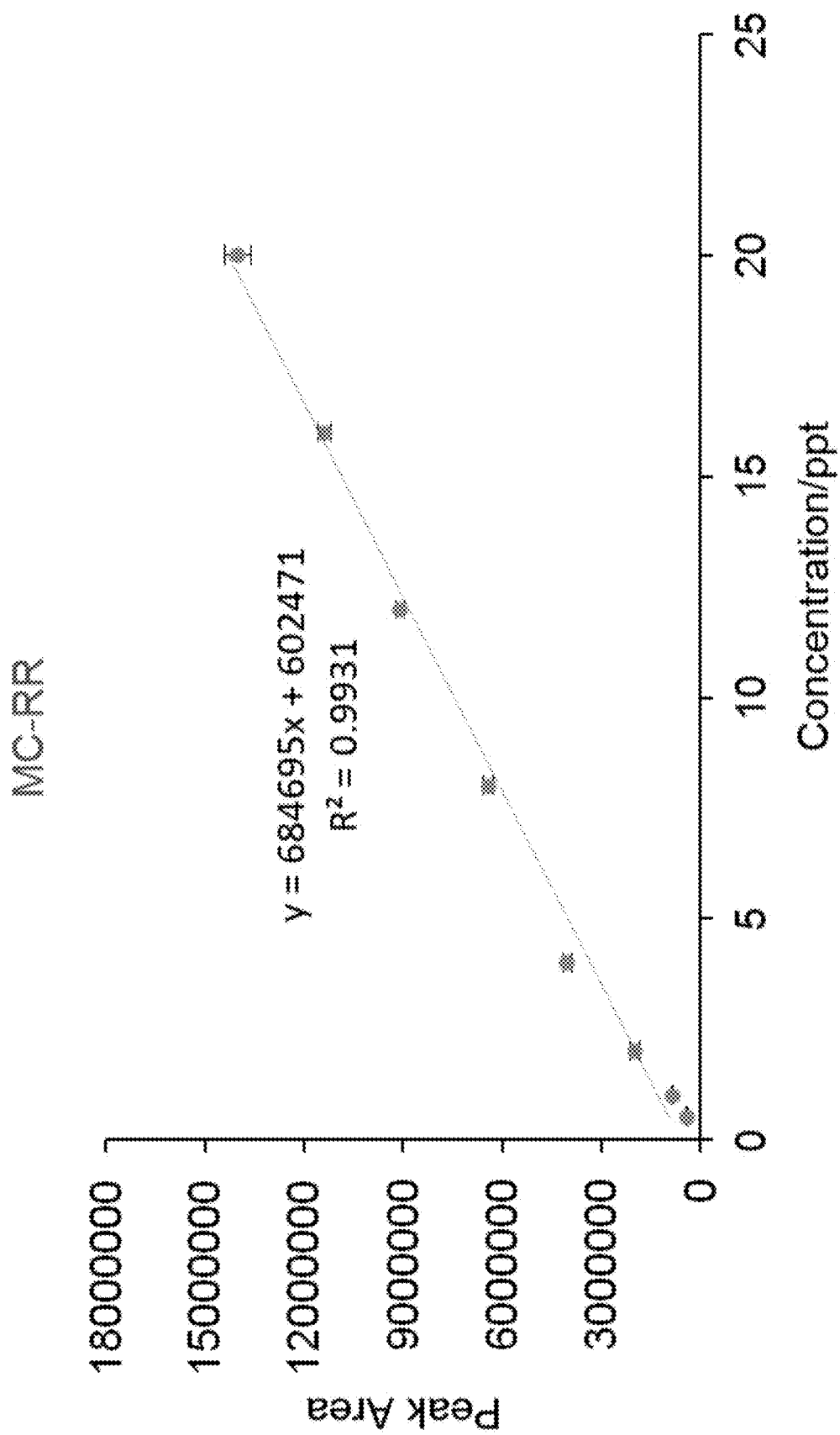

FIG. 14 shows ion chromatograms for a mixture of MCs. FIGS. 15A-15F show the calibration curves without preconcentration (25 pt to 1 ppb). FIG. 16 shows Table 5, displaying the solid-phase extraction recovery data using one SPE cartridge. FIGS. 17A-17F show the calibration curves with preconcentration (500 ppq to 20 ppt). As seen from these results, the method was able to separate six MC species (MC-LR, MC-LA, MC-LF, MC-LW, MC-YR, and MC-RR) with significantly improved LOQs.

Example 3—Solid-Phase Extraction and Quantification of Microcystins from Plasma and Serum Using LC-MS Sensitive, accurate, and reproducible sample preparation and solid-phase extraction (SPE) methods were developed through stepwise optimization in order to extract six common microcystins (MCs; MC-LR, MC-YR, MC-RR, MC-LA, MC-LF, and MC-LW) from spiked mouse plasma and human serum. MCs were quantified using high-performance liquid chromatography-orbitrap-mass spectrometry (HPLCorbitrap-MS). High SPE recoveries with low RSDs for extraction of MCs from mouse plasma and human serum show that the developed methods are accurate and precise. The established method consumes only 40 µL of plasma or serum for extraction of MCs for their subsequent quantification at ng/L concentrations. MCs were quantified with LODs and LOQs in ng/L or µg/L concentrations in spiked plasma and serum samples using SPE-LC-MS. The methods were applied to quantify MC-LR in plasma collected from mice administered MC-LR.

Protein precipitation and SPE are common techniques for purification of MCs from plasma and serum. However, prior studies have not achieved high and reproducible recoveries of MCs extracted from biofluids. Enzyme-linked immunosorbent assay (ELISA) can be used to quantify MCs in serum. ELISA has the advantage of being faster, easier, and cheaper, but has poor reproducibility (i.e., higher relative standard deviations (RSDs)) as well as relatively high limits of detection and quantification. Additionally, it cannot distinguish between different MCs variants. While HPLC-MS has been used to quantify MCs extracted from plasma and serum, the method described in this example includes an aspect of sample preparation which allows for better limits of detection and quantification.

ELISA detects MCs by using an antibody to bind the ADDA moiety present in all MCs (currently there are >150 variants of MCs). MCs are detected by a colorimetric assay and quantification is achieved based on color change of the solution. SPE-LC-MS first extracts MCs from plasma and serum using SPE. The MCs are then separated by LC and analyzed with MS. Quantification is achieved by measuring the peak areas of the MC-related ions in the chromatogram. Sample preparation and SPE protocols provide more accurate and sensitive MC quantification using LC-MS. High SPE recoveries with low RSDs for extraction of MCs from mouse plasma and human serum show that the developed methods are accurate and precise.

Exposure to microcystins (MCs) during harmful algal blooms (HABs) has gained a great deal of attention due to human and animal health and safety concerns. Sensitive and precise analytical strategies for MC quantification in biofluids are essential for accurate assessment of potential health effects. In this example, sample preparation and solid-phase extraction (SPE) protocols were developed to analyze MC-LR, MC-YR, MC-RR, MC-LA, MC-LF, and MC-LW in mouse plasma and human serum using LC-MS and LC-MS/MS. The average recoveries of all MCs from mouse plasma and human serum ranged from 90.4-106.9% and 90.0-104.8%, respectively, with relative standard deviations (RSDs)≤6.3% and ≤5.0%. Quantification of MCs in spiked plasma and serum was achieved at ng/L or µg/L concentrations using an HPLC coupled to an Orbitrap Fusion MS in selected-ion monitoring (SIM) mode. Additionally, an UHPLC binary gradient with multiple reaction monitoring (MRM) MS/MS method was used for the separation and detection of MCs extracted from plasma and serum using a triple quadrupole (QqQ) MS. The sample preparation and SPE methods were applied in a proof-of-concept study to quantify MC-LR extracted from plasma of mice that had been orally administered MC-LR. The LC-MS results indicated that increased MC-LR dosage leads to a larger amount of MC-LR in plasma. The described sample preparation, SPE, and LC-MS methods can be implemented to quantify MCs in plasma and serum.

Introduction

Figure 21:
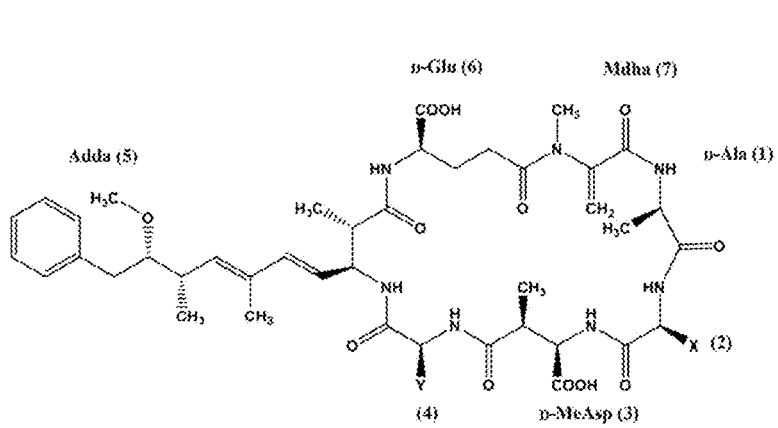
Figure 22A:
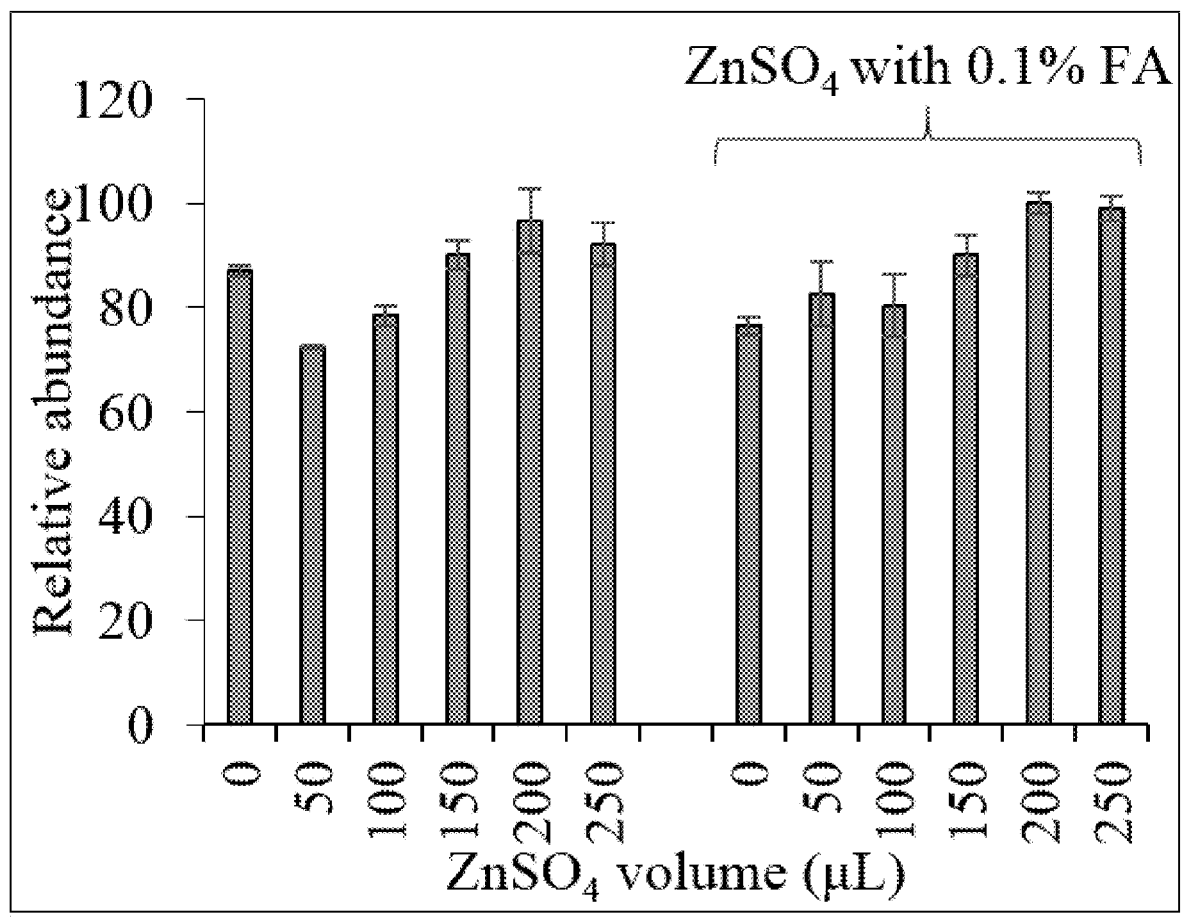
Figure 22B:
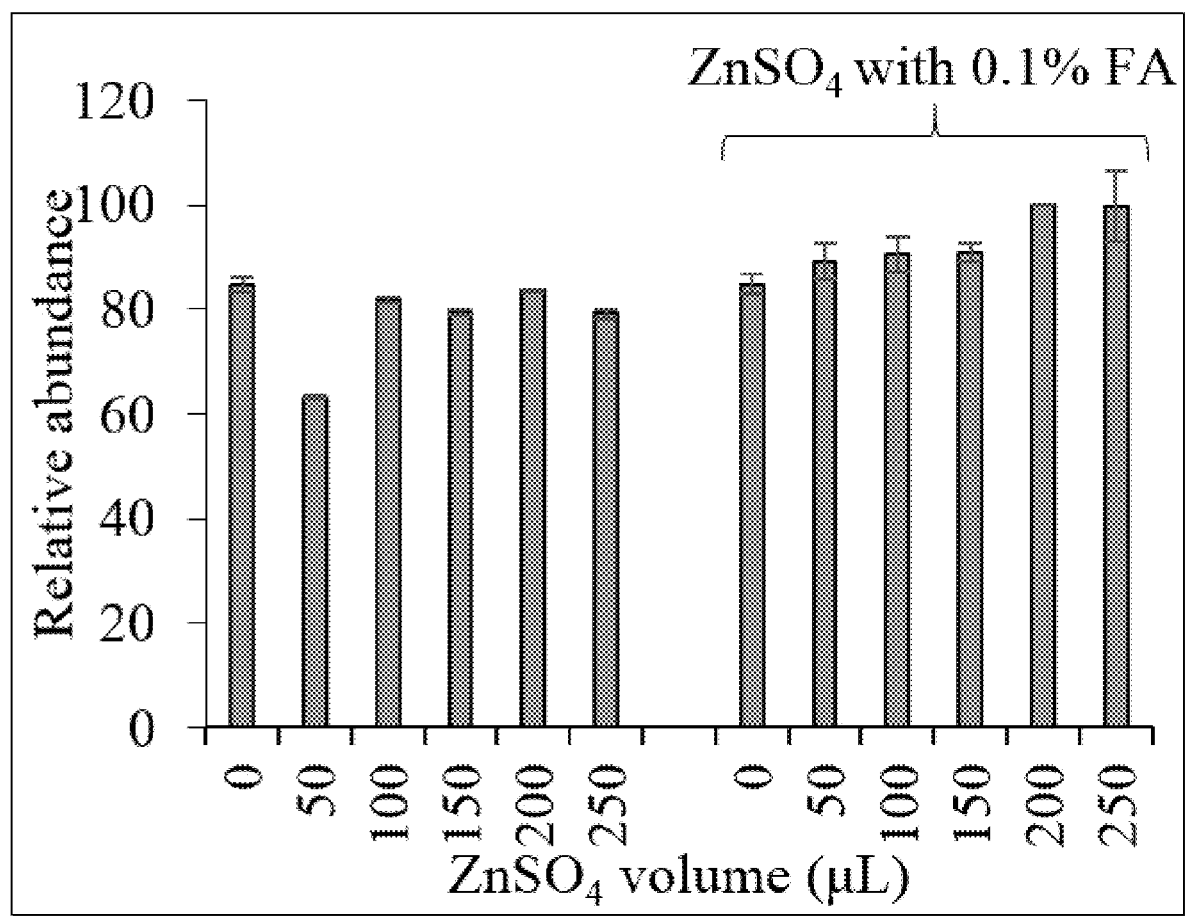
Figure 22C:
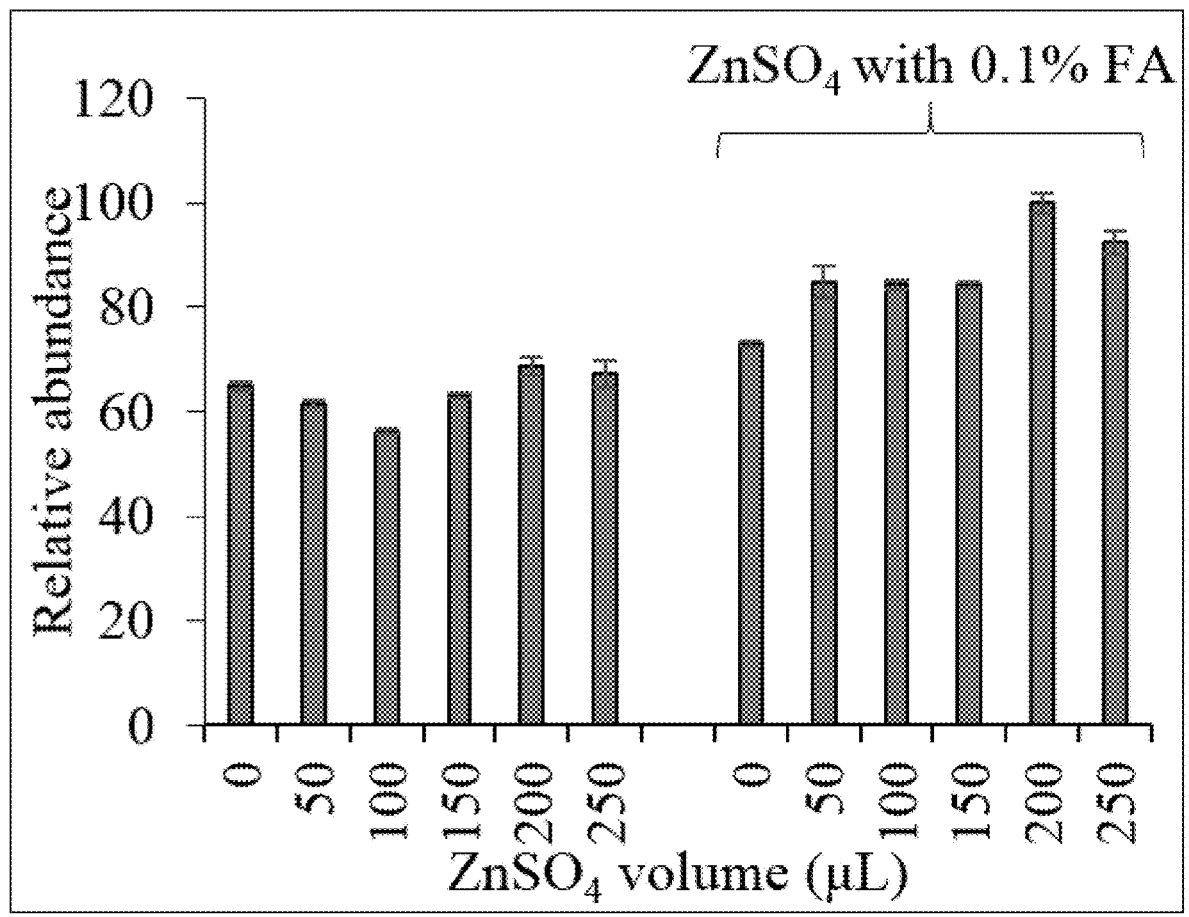
Figure 22D:
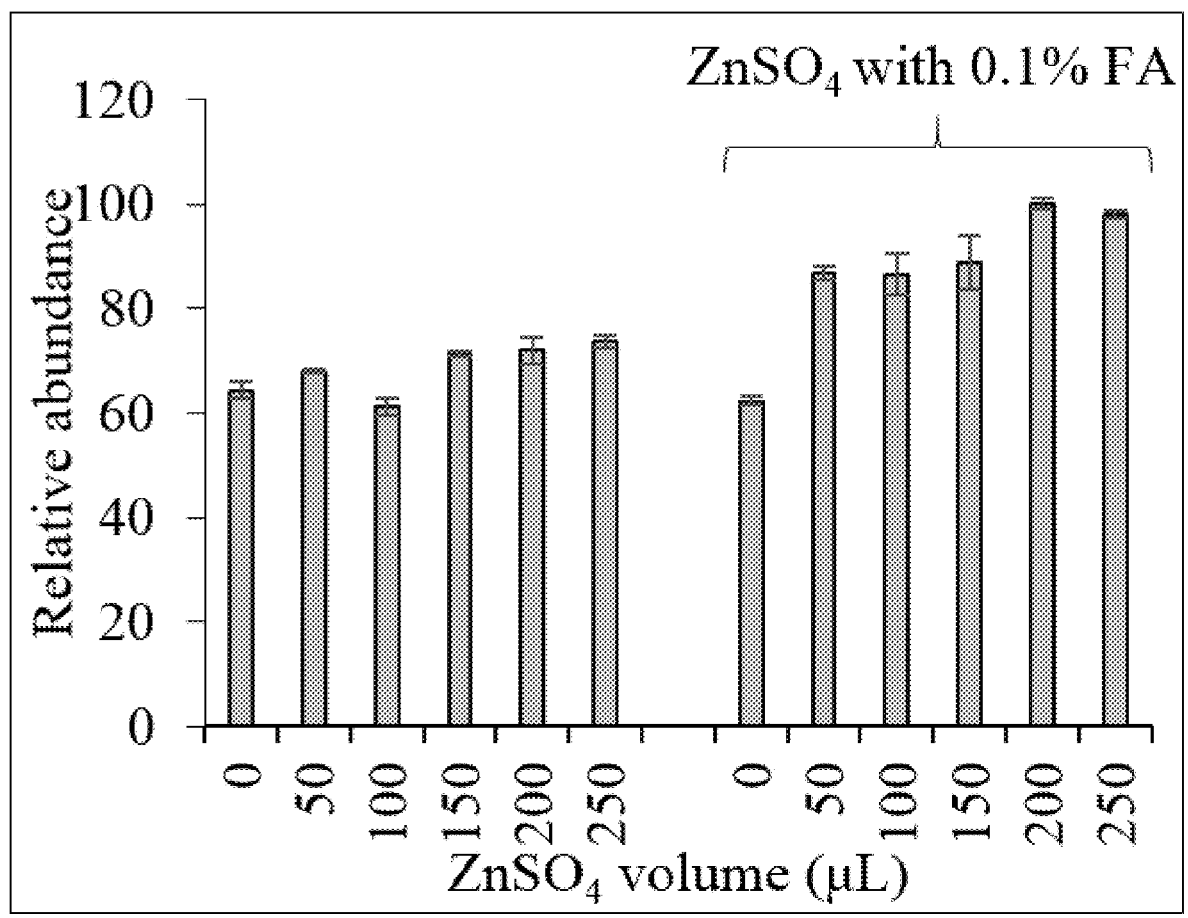
Figure 22E:
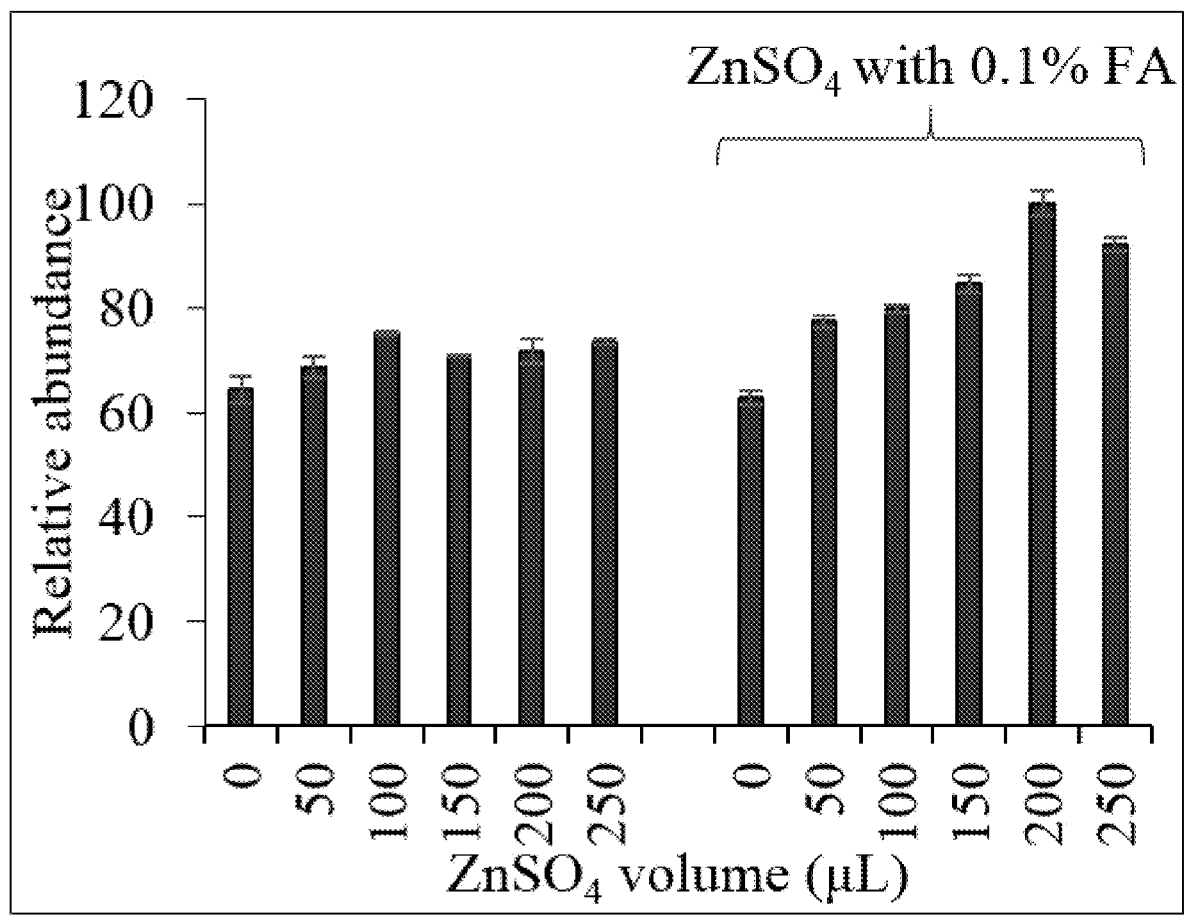
Figure 22F:
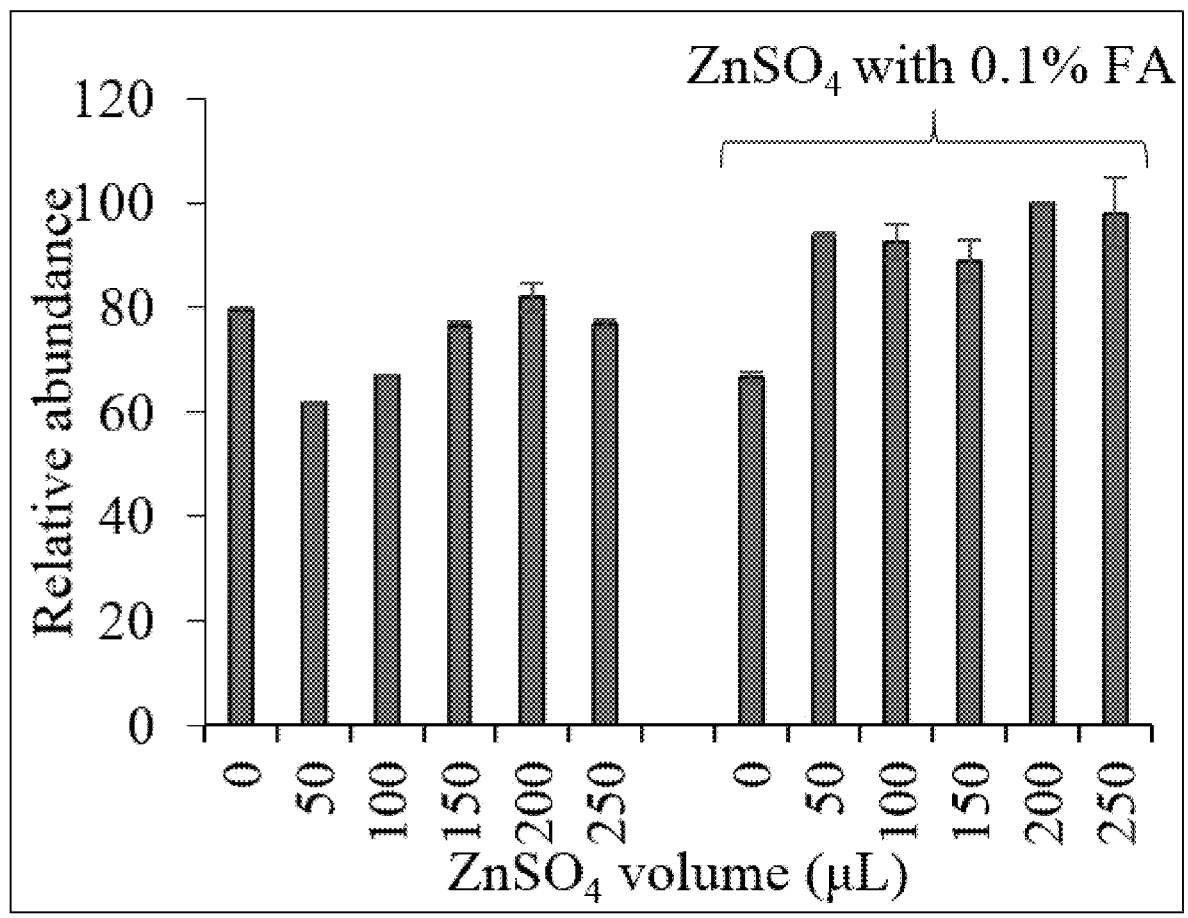
Figure 23A:
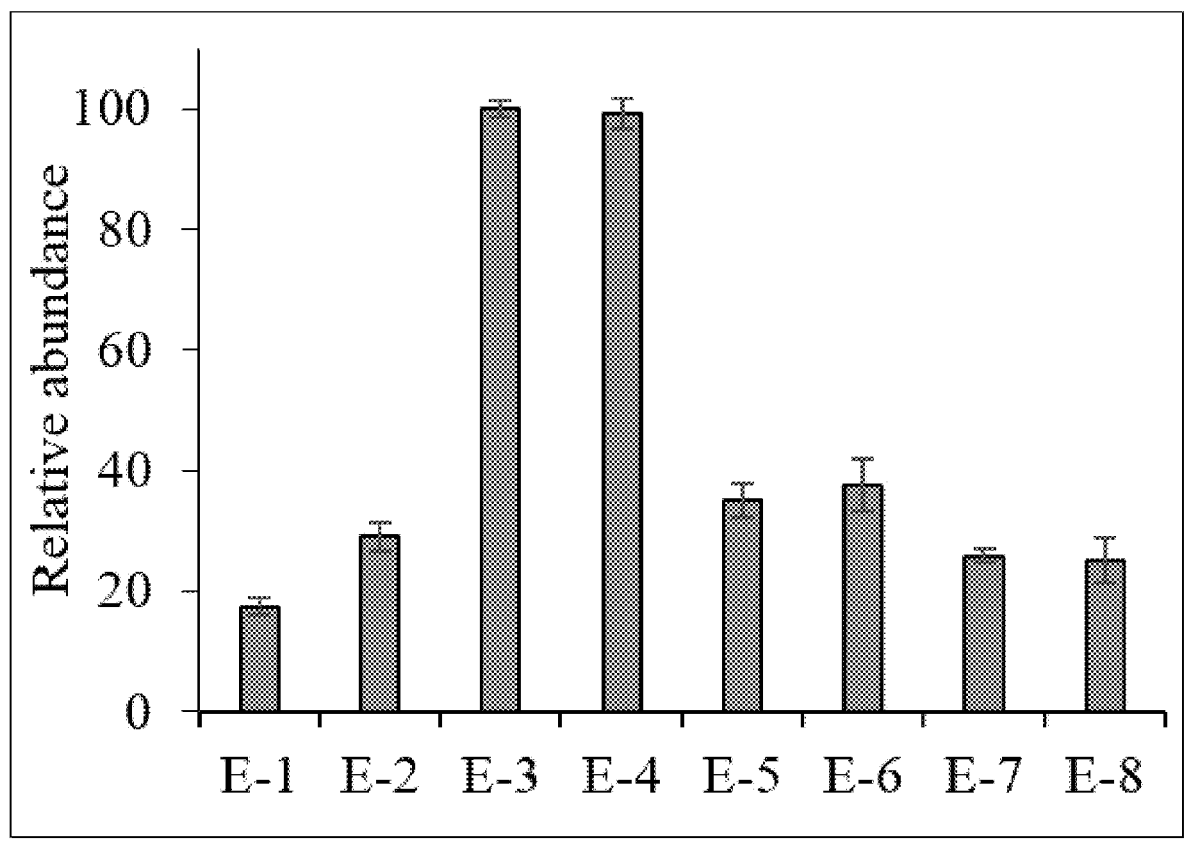
Figure 23B:
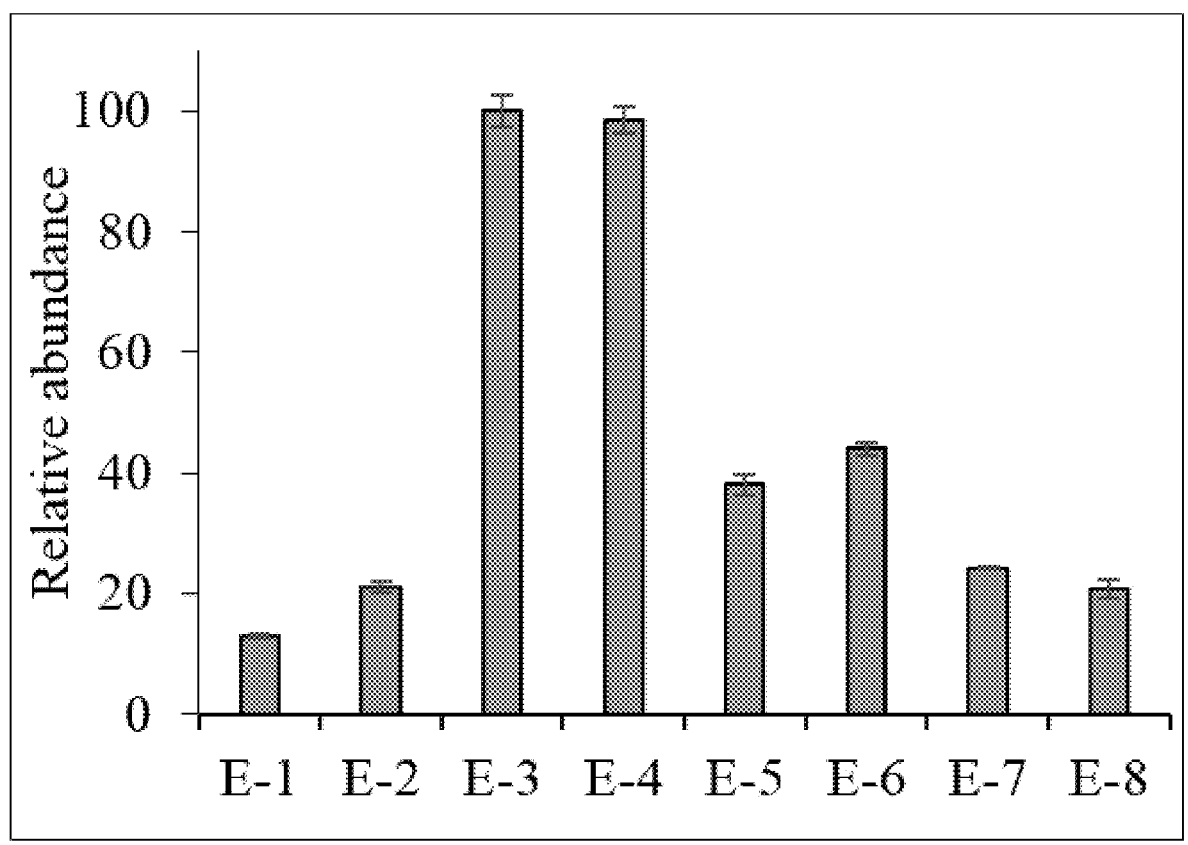
Figure 23C:
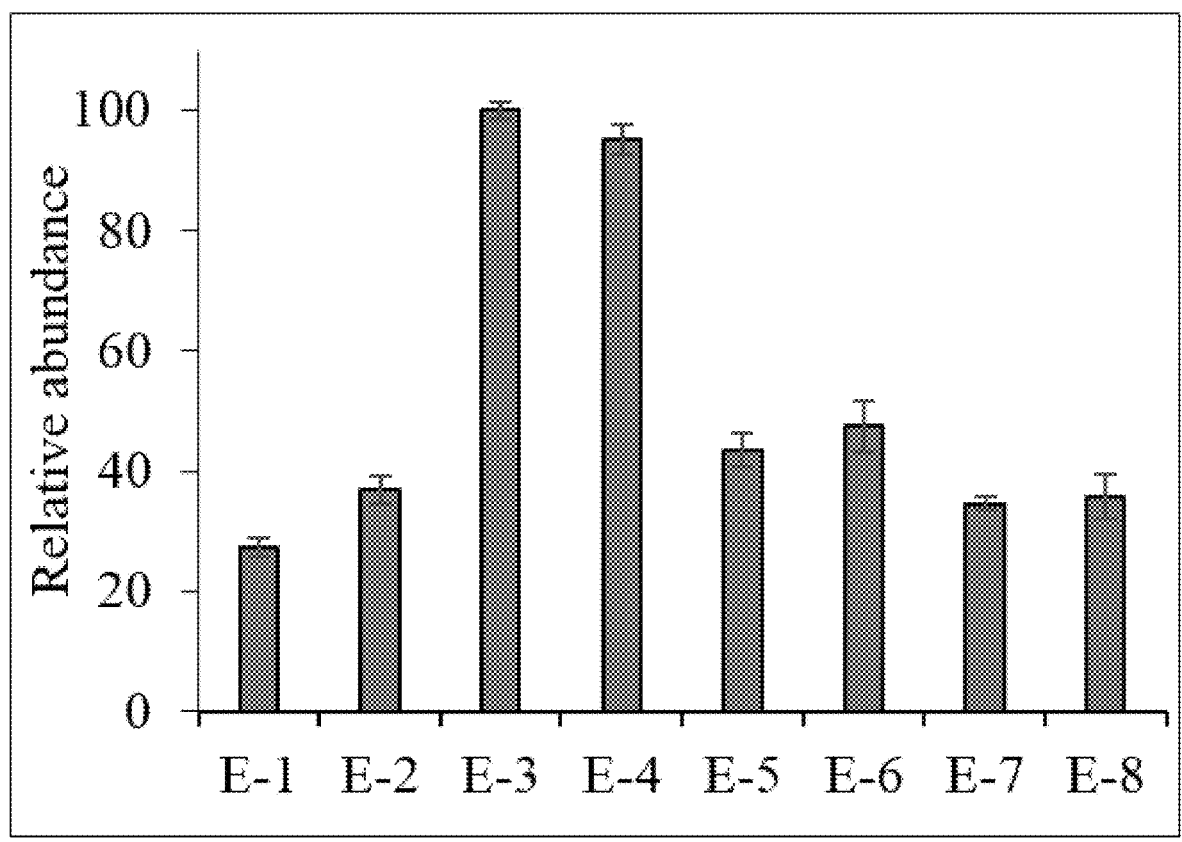
Figure 23D:
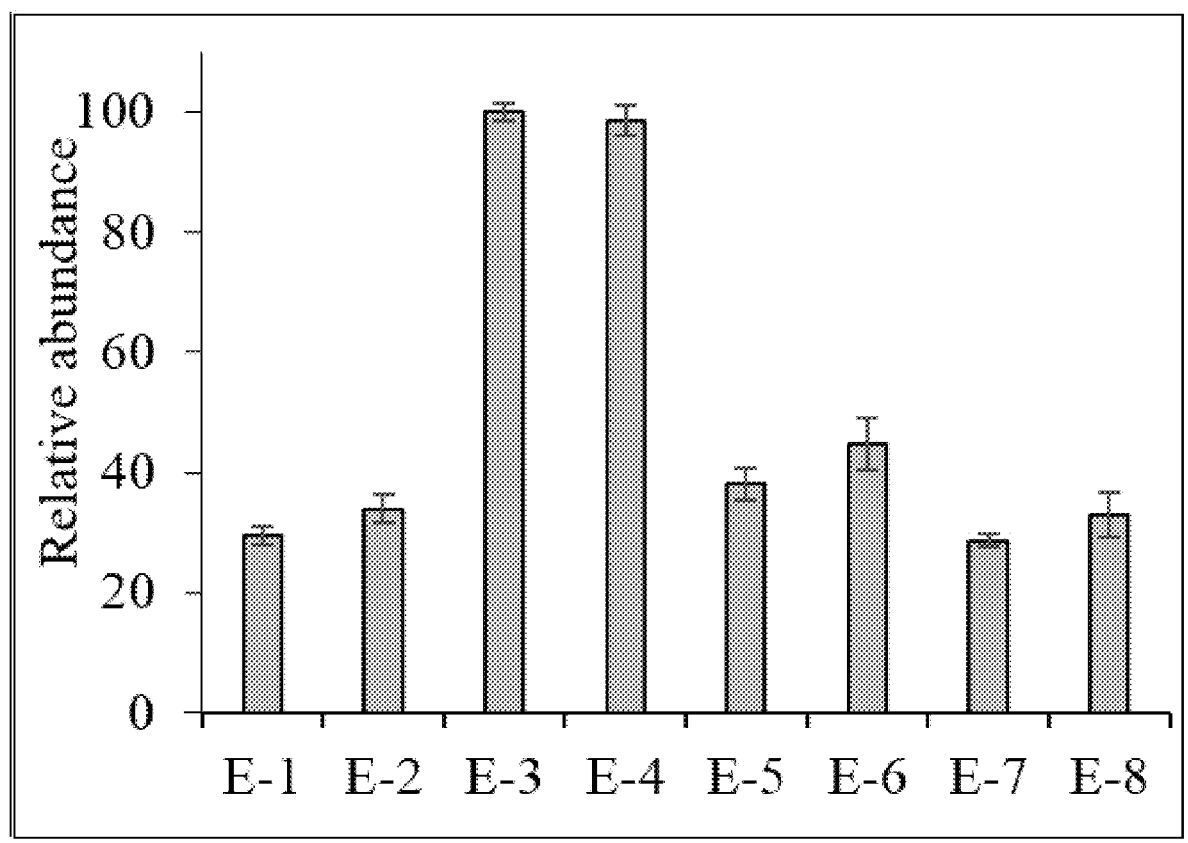
Figure 23E:
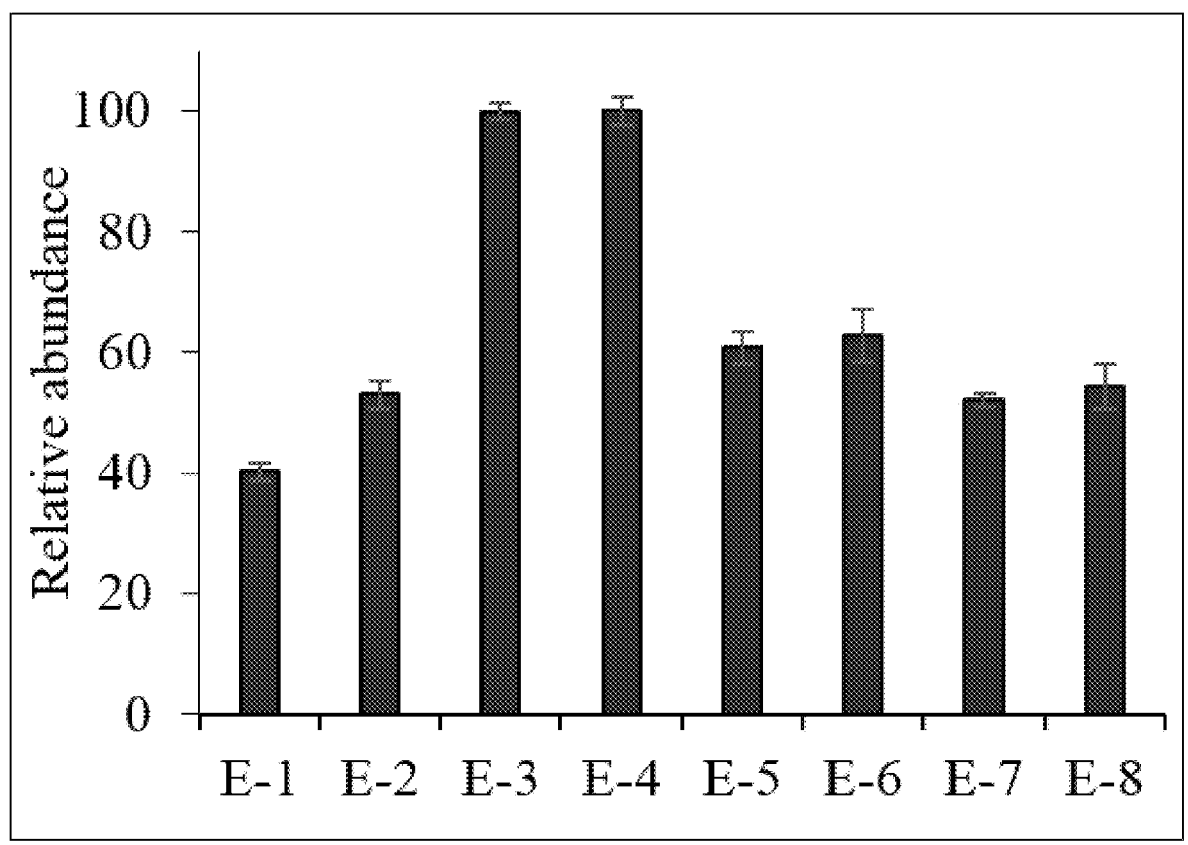
Figure 23F:
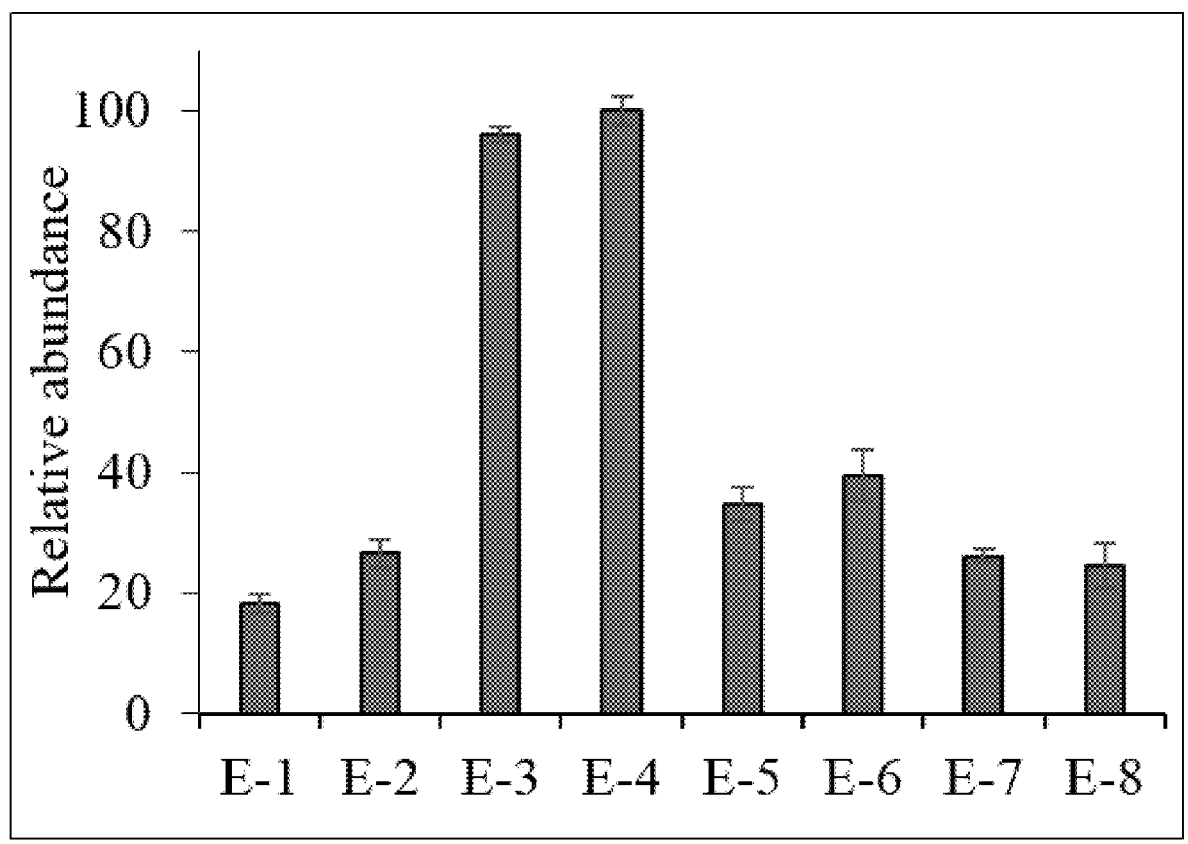

The tremendous growth of cyanobacterial blooms in eutrophic bodies of water and in residential water supplies is a global environmental concern. Cyanobacterial species, such as *Anabaena*, *Microcystis*, *Nostoc*, and *Planktothrix*, produce cyanotoxins, the most common of which are microcystins (MCs). MCs are hepatotoxic cyclic heptapeptides (FIG. 21) which contain the amino acid ADDA (3-amino-9-methoxy-2,6,8-trimethyl-10-phenyldeca-4,6-dienoic acid). To date, over 200 MC congeners have been identified. The congeners are mostly variable in the second and fourth amino acid positions (FIG. 21), or due to side-chain modifications.

Exposure to cyanobacterial toxins produces a variety of human and animal health effects that depend on the route, intensity, and time of exposure. Cyanotoxins can accumulate in aquatic organisms and transfer to higher trophic levels through the food chain. Other significant sources of cyanobacterial toxin exposure are contaminated drinking water and recreational use of water bodies during cyanobacterial blooms.

The toxicity of MCs is due to inhibition of protein phosphatases 1 and 2A, which leads to cancer, hemorrhage, or failure of the liver. Exposure to MCs was linked to human deaths in Brazil due to contamination of water used for hemodialysis. Health effects such as gastrointestinal syndromes, skin damage, respiratory problems, and allergic reactions have also been reported. The acute toxicity of MCs to mammals has been studied based on different doses and administration routes using laboratory mice and rats. MC levels in plasma or serum are often used to assess MC exposure, and most studies have been associated with the detection and quantification of MCs in human, rat, and mouse plasma and serum. Although symptoms related to cyanobacterial toxins have been sporadically reported for decades, prolonged exposure to low levels of MCs is likely to be unnoticed.

Analyses of MCs in biofluids are challenging because of small sample volumes, low MC concentrations, and complex matrices. In addition, MCs are often bound to proteins or peptides in blood, which is problematic for quantification methods because bound MCs may not be detected. Complex matrices can also interfere with MC detection and will lower signal reproducibility and increase the limits of detection (LODs) and quantification (LOQs). Therefore, a purification step is necessary to optimize MC detection and quantification. Protein precipitation and solid-phase extraction (SPE) are the most common purification techniques for MCs in plasma and serum. However, prior studies have not been able to reproducibly achieve high MC recoveries. It is therefore necessary to develop a method to accurately and precisely attain low LODs and LOQs of MCs in plasma and serum.

In this example, sample preparation protocols and SPE methods were developed and validated for the purification of six common MCs (FIG. 21) from mouse plasma and human serum. MCs were detected using two LC-MS systems: HPLC-orbitrap-MS and UHPLC-triple quadrupole (QqQ)-MS/MS. The optimized sample preparation and SPE methods were applied to detect and quantify MC-LR in plasma samples collected from mice that were administered MC-LR using HPLC-orbitrap-MS with internal standard calibration.

Materials and Reagents

HPLC-grade acetonitrile, methanol, and water, and certified ACS-grade zinc sulfate ($ZnSO_4$) were purchased from Fisher Scientific (Pittsburgh, Pa., USA). LC-MS-grade acetonitrile and water from Fisher Scientific were used for UHPLC-MS/MS. Reagent-grade (≥95%) formic acid (FA), 2 mL clear glass vials, and glass inserts were obtained from Sigma (St. Louis, Mo., USA). 3 mL and 10 mL syringes were purchased from Becton, Dickinson and Company (Franklin Lakes, N.J., USA). Standard solutions of MC-LR (500 mg/L), MC-LA (500 mg/L), and MC-RR (100 mg/L) were from Cayman Chemical Company (Ann Arbor, Mich., USA). Solid standards of MC-LW, MC-LF, and MC-YR were purchased from Enzo Life Sciences (Farmingdale, N.Y., USA). A solution of deuterium-labelled MC-LR ($C_2D_5$-monoethyl ester MC-LR, Cambridge Isotope Laboratories, Tewksbury, Mass., USA) was used as an internal standard (MC-IS, 100 mg/L stock solution) for quantification of MC-LR. Sep-Pak C18 Plus Light SPE Cartridges were from Waters (Milford, Mass., USA), and the heated vacuum concentrator Vacufuge plus was from Eppendorf (Hamburg, Germany)

Sample Preparation

Optimization of Extraction of MCs from Spiked Plasma and Serum

Frozen mouse plasma and human serum samples were thawed from −80° C. to room temperature and vortexed. MC stock solutions (MC-LR, MC-RR, MC-LA, MC-LF, MC-LW and MC-YR) and MC-IS were diluted with methanol to prepare MC standard solutions.

The optimized sample preparation for extraction of MCs was the same for mouse plasma and human serum. 40 µL of the biofluid was transferred into a 50 mL centrifuge tube. 200 µL of 100 mM $ZnSO_4$ was added to the solution, and the solution was diluted with HPLC-grade water and acidified to 0.1% FA for a total volume of 2 mL. SPE was performed on the plasma and serum samples as follows: the SPE cartridge was conditioned with 2 mL of 90:10 methanol:water (v/v) containing 0.1% FA and equilibrated with 2 mL of 0.1% FA. The sample was loaded onto the cartridge and washed with 2 mL of 0.1% FA. The MCs were eluted using methanol containing 0.1% FA. The solvent was evaporated using a vacuum concentrator and the residue was redissolved in 100 µL of 90:10 methanol:water (v/v) containing 0.1% FA for LC-MS analyses.

For initial optimization experiments, recovery experiments, and quantification using internal calibration standards, plasma, and serum samples were spiked with the MC mixture. Samples were analyzed on both HPLC-orbitrap-MS and UHPLC-QqQ-MS/MS systems.

Collection of Mouse Plasma and Extraction of MC-LR

All animal experiments were conducted in accordance with the National Institutes of Health Guide for the Care and Use of Laboratory Animals using protocols approved by the University of Toledo, Health Science Campus, Institutional Animal Use and Care Committee. Ten-week-old male $Lepr^{db}$/J mice weighing 40-45 g were obtained from Jackson Laboratories and gavaged with vehicle (300 µL of 0.9% saline), 50 µg MC-LR per kg bodyweight (50 µg/kg MC-LR), or 100 µg/kg MC-LR for 5 weeks. These doses approximate the currently accepted no observed adverse effect level (NOAEL) of 40 µg/kg established after 13-week MC-LR administration. Plasma samples were collected by cardiac puncture in K3-EDTA microtubes (Sarstedt, Newton, N.C., USA) after the final dose and stored at −80° C. until batch analysis. The samples were thawed and vortexed. 40 µL of plasma samples were spiked with a constant amount of MC-IS (4 µL of 100 µg/L solution). MC-LR calibration standards were prepared in control mouse plasma in the range of 0.25 µg/L to 30 µg/L by spiking different amounts of MC-LR and a constant amount of internal standard (4 µL of 100 µg/L solution). The samples and calibration standards were prepared and SPE was performed using the optimized methods. These samples were analyzed on the LC-orbitrap-MS system.

Liquid Chromatography and Mass Spectrometry

HPLC-Orbitrap-MS

The HPLC-MS system consisted of an Orbitrap Fusion Tribrid mass spectrometer with an electrospray ionization (ESI) source (Thermo Fisher Scientific, San Jose, Calif., USA) and an HPLC system (Shimadzu Technologies, Addison, Ill., USA) containing two LC-20AD pumps, a DGU-20A3 degasser, a SIL-20A HT autosampler, and a CBM-20A system controller. Chromatographic separation was achieved by reversed-phase XBridge C8 column (3.0×100 mm, 3.5 µm, Waters, Milford, Mass.) with a C8 guard column (3.0×20 mm, 3.5 µm, Waters, Milford, Mass.). The LC-MS method was previously developed. Briefly, mobile phase A (0.05% FA in water) and mobile phase B (acetonitrile containing 0.05% FA) were pumped at a flow rate of 0.3 mL/min. The column was equilibrated with 20% of mobile phase B for 30 minutes prior to initial injection. Optimized separation of MCs was obtained using a gradient that started with 20% B and increased to 60% B from 0.1 to 2 minutes, 70% B from 2 to 7 minutes, and 90% B from 7 to 12 minutes, and then decreased to 20% B from 12 to 14 minutes. The column was re-equilibrated for 6 min at 20% B. All analytes were separated in a total run time of 20 min and the sample injection volume was 20 µL.

MS and MS/MS were performed simultaneously and ESI-selected-ion monitoring (SIM)-MS in positive ion mode was used for quantification of MCs as described in the previous study. MS/MS was performed by fragmenting MC precursor ions with higher-energy collision-induced dissociation (HCD) and analyzing fragments with a linear ion trap mass analyzer. The ADDA fragment ion $[C_6H_5-CH_2CH(OCH_3)]^+$ at m/z 135.08 was used for identification of MCs in MS/MS mode. Seven SIM channels were used per run. Singly-charged protonated ions ($[M+H]^+$) of MC-LR (m/z 995.56), MC-LA (m/z 910.49), MC-LW (m/z 1025.53), MC-LF (m/z 986.52), MC-YR (m/z 1045.54), and MC-IS (m/z 1028.62), and the doubly-charged protonated ($[M+2H]^{2+}$) ion of MC-RR (m/z 519.79) were monitored with mass accuracy <3.0 ppm and used for quantification. All samples were analyzed in triplicate. MS data were acquired and analyzed using Xcalibur software (Thermo Scientific) and the extracted-ion chromatogram (EIC) peak areas of monoisotopic MC ions were used for data calculation.

UHPLC-OqO-MS/MS

MCs extracted from plasma and serum were also detected using UHPLC-QqQ-MS/MS (LCMS-8050, Shimadzu, Columbia, Md., USA). The UHPLC system consisted of two LC-20AD XR pumps, two DGU-20A3R degasser units, a SIL-20AC XR autosampler, a CTO-20A column oven, and a CBM-20A system controller. Liquid chromatography separations were performed with an Acquity HSS T3 C18 column (1.8 µm, 3.0×50 mm, Waters) and an Acquity HSS T3 C18 guard column (1.8 µm, 2.1×5 mm, Waters) heated to 45° C. The mobile phase consisted of 0.1% FA in water (mobile phase A) and acetonitrile containing 0.1% FA (mobile phase B). The injection volume was 20 µL and a flow rate of 0.4 mL/min was used. The column was equilibrated with 10% B prior to LC-MS injection. The gradient started at 10% B, increased to 25% B from 0.01 to 0.05 minutes, increased to 95% B from 0.05 to 4.80 minutes, maintained at 95% B from 4.80 to 5.00 minutes, and decreased to 10% B from 5.00 to 5.01 minutes. The column was equilibrated at 10% B for 4.99 minutes.

The UHPLC was coupled to a QqQ-MS/MS with an ESI source operating in positive ion mode with multiple reaction monitoring (MRM). The ESI source and instrument parameters were optimized prior to LC-MS. The following working conditions were applied to MS analyses: interface voltage, conversion dynode, and detector voltages were 4.0, 10.0 and 1.96 kV, respectively. Interface, desolvation line, and heatblock temperatures were 300, 125, and 400° C., respectively. Nebulizing, drying, and heating gas flow rates were 2.0, 10.0, and 10 L/min, respectively. Pressure of Ar in the collision-induced dissociation cell was 270 kPa. The mass resolution at the first (Q1) and third (Q3) quadrupoles were set to unit resolution. The loop time was 0.424 s and dwell time was 50.0 msec. Seven MRM channels were used per run for MC-LR, MC-RR, MC-LF, MC-LW, MC-YR, MC-LA, and MC-IS, and transitions were m/z 995.50→135, m/z 519.90→135, m/z 986.40→135, m/z 1025.45→135, m/z 1045.55→135, m/z 910.60→135, and m/z 1028.50→135, respectively. The Q1 pre bias voltages for MC-LR, MC-RR, MC-LF, MC-LW, MC-YR, MC-LA, and MC-IS were −22, −26, −22, −38, −30, −34, and −38 V, respectively, while Q3 pre bias voltages were −26, −26, −26, −14, −30, −22, and −15 V, respectively. The collision energies (CEs) for MC-LR, MC-RR, MC-LF, MC-LW, MC-YR, MC-LA, and MC-IS were −55, −32, −51, −54, −55, −53, and −33 V respectively. The data was processed using Lab Solutions software (Shimadzu, Columbia, Md., USA), and MRM peak areas were used for data analyses.

LODs, LOQs, and Recovery Determination

For all samples, LODs and LOQs were obtained experimentally by detecting monoisotopic MC ions from spiked mouse plasma and human serum with signal-to-noise ratios in the EICs of ~3 and 10, respectively. For sample preparation and SPE optimization, relative abundances of the MC ions were compared using the EIC areas of the MC monoisotopic peaks for LC-orbitrap-MS and MRM peak areas for LC-QqQ-MS/MS. EIC peak areas of the monoisotopic peak and MRM peak areas of each MC ion in the extracted samples and controls were compared to find the SPE recoveries of MCs using LC-orbitrap-MS and LC-QqQ-MS/MS, respectively.

Results and Discussion

Optimization of MC Extraction from Mouse Plasma Samples

Separation of MCs was achieved by HPLC in a twenty-minute run and MCs were analyzed using ESI-SIM-MS. The retention times were 5.65 (MC-RR), 5.88 (MC-YR), 6.02 (MC-LR), 6.36 (MC-IS), 7.38 (MC-LA), 8.20 (MC-LW), and 8.53 (MC-LF) minutes (data not shown). An LC-MS method was used to analyze MCs on the Shimadzu LC-MS 8050 instrument, and the retention times were 2.05 (MC-RR), 2.41 (MC-YR), 2.49 (MC-LR), 2.76 (MC-IS), 3.43 (MC-LA), 3.86 (MC-LW), and 4.01 (MC-LF) minutes. MRM transitions to m/z ~135 were detected for all MC precursor ions and the peak areas of this fragment were used for data calculations.

Initially, a sample preparation method was developed for the extraction of MCs from mouse plasma. MCs were spiked into 40 µL of plasma to yield 12.5 µg/L concentrations of each MC. Different amounts of 100 mM $ZnSO_4$ solution were introduced to spiked plasma samples in 50 µL increments to optimize $ZnSO_4$ concentration (FIG. 22). The samples were diluted to 2 mL with HPLC-grade water. For another set of samples, after adding $ZnSO_4$, samples were diluted with water and acidified to 0.1% FA to investigate the effect of acidity (FIG. 22). SPE was performed based on our previously developed method to extract MCs in water.

Samples were analyzed using both HPLC-orbitrap-MS and UHPLC-QqQ-MS/MS. Relative abundances of the measured MC ions were compared, and the results (FIG. 22) indicated that $ZnSO_4$ improved the extraction efficiency of MCs from mouse plasma. MS and MS/MS signals of all MCs were the highest after adding 200 µL of 100 mM $ZnSO_4$ solution into 40 µL of plasma. An increase in signal was also observed when samples were acidified with FA (FIG. 22). A possible rationalization for these results are that $ZnSO_4$ and low pH conditions release MCs bound to proteins. Some proteins were shown to bind covalently to MCs via a Michael addition to the Mdha residue of the MCs, and MCs can also bind to proteins through hydrophobic interactions. Therefore, it is important to release MCs that are bound to plasma and serum proteins. Zinc binds with high affinity to specific sites of proteins and is highly competitive with other molecules and ions. Zinc has coordination numbers from two to eight, enabling it to bind a wide variety of ligands in proteins and peptides through N, O, and S donors of the side-chains of histidine, glutamate, aspartate, and cysteine. Therefore, zinc ions may help to release protein-bound MCs by displacing the MCs. Proteins denature at low pH and $Zn^{2+}$ ions can more easily access MC binding sites in the presence of FA. Considering the effect of $ZnSO_4$ and sample acidity on the extraction efficiency of MCs from mouse plasma, sample preparation was conducted in the presence of 200 µL of 100 mM $ZnSO_4$ and 0.1% FA.

Extraction and Recovery of MCs from Mouse Plasma

The SPE steps were optimized to achieve the best MC recoveries. Several solvents have been used for MC extraction in plasma, and a consensus has not been reached on which is the best. Some investigations found that the efficiency of eluting solvents depended on various factors, such as the water content of the sample and eluent polarity. Thus, various water/methanol/acetonitrile ratios and solvent acidities were tested for elution of MCs from the SPE cartridges. Different equilibration and elution solvents (Table 4) were tested by maintaining the conditioning and washing steps as 90:10 (v/v) methanol:water containing 0.1% FA and 0.1% FA, respectively. As shown in FIG. 23, the highest extraction efficiencies for all MCs were observed with methanol containing 0.1% FA as the elution solvent and 0.1% FA as the equilibration solvent (E-3).

TABLE 4

Equilibration and elution solvents tested for SPE of MCs from mouse plasma

| Solvent combination | Equilibration solvent | Elution solvent |
|---|---|---|
| E-1 | 0.1% FA | Methanol |
| E-2 | Water | Methanol |
| E-3 | 0.1% FA | Methanol + 0.1% FA |
| E-4 | Water | Methanol + 0.1% FA |
| E-5 | 0.1% FA | 90:10 Methanol:water + 0.1% FA |
| E-6 | Water | 90:10 Methanol:water + 0.1% FA |
| E-7 | 0.1% FA | 90:10 Acetonitrile:water + 0.1% FA |
| E-8 | Water | 90:10 Acetonitrile:water + 0.1% FA |

Reversed-phase C18 SPE cartridges have excellent retention capacity for proteins and peptides via hydrophobic interactions. MCs have hydrophobic and hydrophilic regions and may exist as charged molecules under acidic condition. In the elution step of SPE, the retained MCs should be completely desorbed by using as little eluent as possible. Methanol has the ability to elute proteins and peptides from reversed-phase SPE cartridges while hydrophobic molecules are retained on the cartridge. In addition, any free silanol groups can exhibit cation-exchange properties, and adjustment of the pH of the elution solvent is necessary to disrupt these interactions with charged analytes. Here, acidified methanol was used to elute MCs while minimizing matrix interferences (FIG. 23). MCs showed lower signal responses for other elution solvents, possibly due to matrix compounds coeluting with target analytes, which can cause a change in the MS response of the MCs by ion suppression. 0.1% FA was selected as the washing solvent. Clean extracts might be obtained by washing with organic solvents, but MCs may also elute and recovery will be reduced. The comparison of different elution solvents (FIG. 23) demonstrated that acidified methanol was the most effective solvent for MC extraction from plasma using a C18 SPE cartridge.

The accuracy and precision of the SPE method was determined after optimizing the sample preparation and SPE steps. The average percent recovery was calculated by using three SPE cartridges to extract MCs at two concentration levels (Table 5). 40 µL aliquots of mouse plasma were spiked with MCs to prepare samples containing 1 µg/L and 10 µg/L of each MC. SPE was performed as described above and the samples were analyzed in triplicate by both LC-orbitrap-MS and LC-QqQ-MS/MS. Controls were prepared using the same sample preparation and SPE procedures, but MCs were spiked in redissolved control samples after SPE. Table 5 summarizes the average recoveries and RSDs of MCs analyzed using LC-orbitrap-MS. For all MCs, recoveries ranged from 90.4-106.9% and relative standard deviations were ≤6.3%. Similar recoveries (90.7-101.9% with RSDs ≤4.9%) were observed when samples were analyzed with LC-QqQ-MS/MS (Table S1). Low RSDs and high recoveries confirmed the good precision and accuracy of the extraction method.

TABLE 5

Percent recoveries and RSDs of MCs after SPE purification of solutions containing 1 µg/L and 10 µg/L of six MCs in mouse plasma analyzed using HPLC-orbitrap-MS

| Concentration (µg/L) | MC variant | Cartridge 1 Recovery (%) | Cartridge 1 RSD (%) | Cartridge 2 Recovery (%) | Cartridge 2 RSD (%) | Cartridge 3 Recovery (%) | Cartridge 3 RSD (%) |
|---|---|---|---|---|---|---|---|
| 1 | MC-LR | 97.7 | 2.1 | 98.6 | 4.4 | 102.9 | 3.3 |
|  | MC-RR | 95.0 | 3.1 | 95.5 | 3.3 | 102.3 | 2.6 |
|  | MC-LA | 91.5 | 3.7 | 90.4 | 3.3 | 96.0 | 2.5 |
|  | MC-LF | 97.2 | 2.6 | 94.5 | 2.8 | 102.6 | 3.0 |
|  | MC-LW | 94.6 | 3.9 | 94.2 | 2.5 | 100.4 | 1.5 |
|  | MC-YR | 101.0 | 2.5 | 93.1 | 2.7 | 95.9 | 3.4 |
|  | MC-IS | 100.2 | 4.7 | 102.6 | 2.6 | 101.8 | 3.2 |
| 10 | MC-LR | 95.3 | 4.4 | 104.6 | 3.8 | 97.4 | 3.9 |
|  | MC-RR | 93.3 | 3.7 | 103.2 | 2.6 | 102.1 | 3.3 |
|  | MC-LA | 94.5 | 3.7 | 97.6 | 3.5 | 101.1 | 4.8 |
|  | MC-LF | 96.6 | 4.1 | 106.9 | 2.0 | 100.3 | 2.5 |
|  | MC-LW | 93.8 | 3.9 | 103.3 | 2.4 | 96.3 | 1.7 |
|  | MC-YR | 92.4 | 2.5 | 102.5 | 1.2 | 93.2 | 6.3 |
|  | MC-LS-IR | 91.1 | 3.4 | 99.7 | 3.8 | 91.9 | 4.0 |

Quantification of MCs in Spiked Mouse Plasma

MCs were quantified in spiked mouse plasma after optimization of sample preparation and SPE. The matrix-matched internal calibration curves were constructed in the range of 0.5 µg/L to 20 µg/L for MC-RR, MC-YR, and MC-LR, and 1.0 µg/L to 20 µg/L for MC-LA, MC-LF, and MC-LW. Samples were analyzed in triplicate using LC-orbitrap-MS. Table 6 shows linearity of calibration curves with $R^2 \geq 0.998$ for MC-LR, MC-RR, and MC-YR, while $R^2$ was ≥0.9906 for MC-LA, MC-LW, and MC-LF. LODs and LOQs were ~0.08 µg/L and ~0.3 µg/L, respectively, for MC-LR, MC-RR, and MC-YR, and ~0.3 µg/L and ~1.0 µg/L for MC-LA, MC-LF and MC-LW. The plasma sample volume can be increased to achieve lower LODs and LOQs. Arginine residues in MC-LR, MC-YR, and MC-RR improve their ionization, and those MCs exhibit lower LODs and LOQs than MC-LA, MC-LF, and MC-LW.

TABLE 6

Internal standard calibration curve equations, $R^2$ values, LODs, and LOQs for MC-spiked plasma samples

| MC variant | Equation of calibration curve | $R^2$ | LOD (µg/L) | LOQ (µg/L) |
|---|---|---|---|---|
| MC-LR | y = 0.4096x + 0.0106 | 0.9958 | 0.08 | 0.30 |
| MC-RR | y = 1.113x + 0.0453 | 0.996 | 0.08 | 0.30 |
| MC-LA | y = 0.255x + 0.0049 | 0.9937 | 0.30 | 1.00 |
| MC-LF | y = 0.1144x + 0.0024 | 0.9906 | 0.30 | 1.00 |
| MC-LW | y = 0.156x + 0.0026 | 0.9895 | 0.30 | 1.00 |
| MC-YR | y = 0.2944x + 0.0023 | 0.9958 | 0.08 | 0.30 |

Internal standard calibration curves were validated using MC-spiked samples at concentrations of 1.0 µg/L, 2.5 µg/L, 5.0 µg/L, and 10.0 µg/L for each MC (Table 7). The calculated MC concentrations in the analyzed samples, as well as corresponding RSDs and percent errors, are shown in Table 7. Low RSDs (≤8.7%) at all concentration levels indicate that the method is precise and MCs can be quantified in the concentration range shown in the calibration curves (Table 7). MC quantities determined at lower concentrations (1.0 µg/L) had errors ≤12.9%. At higher MC concentrations (2.5, 5.0, and 10.0 µg/L), the errors were ≤7.7%.

TABLE 7

Validation of calibration curves for quantification of MCs in spiked mouse plasma. Calibration curves were used for quantification.

| Actual concentration (µg/L) | MC variant | Measured concentration (µg/L) | RSD (%) | Error (%) |
|---|---|---|---|---|
| 1.0 | MC-LR | 0.96 | 1.7 | 4.3 |
|  | MC-RR | 1.07 | 1.6 | 7.0 |
|  | MC-LA | 0.96 | 8.9 | 7.2 |
|  | MC-LF | 0.90 | 8.1 | 9.7 |
|  | MC-LW | 0.87 | 8.7 | 12.9 |
|  | MC-YR | 0.89 | 5.4 | 7.0 |
| 2.5 | MC-LR | 2.65 | 4.4 | 3.2 |
|  | MC-RR | 2.59 | 2.7 | 3.6 |
|  | MC-LA | 2.39 | 8.1 | 4.3 |
|  | MC-LF | 2.58 | 8.3 | 6.0 |
|  | MC-LW | 2.31 | 6.0 | 7.7 |
|  | MC-YR | 2.64 | 5.3 | 5.7 |
| 5.0 | MC-LR | 5.23 | 4.5 | 1.8 |
|  | MC-RR | 5.25 | 2.3 | 5.0 |
|  | MC-LA | 5.17 | 3.5 | 3.5 |
|  | MC-LF | 5.24 | 6.5 | 4.7 |
|  | MC-LW | 4.91 | 4.4 | 4.6 |
|  | MC-YR | 5.34 | 6.4 | 6.9 |
| 10.0 | MC-LR | 10.16 | 2.1 | 1.6 |
|  | MC-RR | 10.17 | 1.9 | 1.7 |
|  | MC-LA | 10.56 | 2.5 | 5.6 |
|  | MC-LF | 10.74 | 5.7 | 7.4 |
|  | MC-LW | 10.50 | 4.8 | 5.0 |
|  | MC-YR | 10.34 | 2.0 | 3.4 |

Internal standard calibration curves for quantification of MC-LR, MC-RR, and MC-YR showed better linearity ($R^2 \geq 0.998$) than for MC-LA, MC-LF, and MC-LW ($R^2 \geq 0.9906$). The internal standard is expected to be the most effective for quantification of MC-LR since it is ethylated and deuterated MC-LR. Compared to MC-LA, MC-LF, and MC-LW, MC-RR, and MC-YR have more properties similar to MC-IS due to the arginine moiety. Therefore, calibration curves for quantification of MC-LR, MC-RR, and MC-YR show better linearity than those for MC-LA, MC-LF, and MC-LW, and MC-LR, MC-RR, and MC-YR can be quantified with lower percent error (Table 6 and Table 7).

Extraction and Recovery of MCs from Human Serum

The method developed for SPE of MCs from mouse plasma was used to extract MCs from human serum. The sample preparation steps were tested by adding FA and different amounts of 100 mM $ZnSO_4$ solution. Samples were analyzed using both LC-orbitrap-MS and LC-QqQ-MS/MS. Similar to plasma samples, the highest signal response was observed for serum samples with 200 µL of 100 mM $ZnSO_4$ and acidified to 0.1% FA.

The accuracy of sample preparation and SPE procedures was analyzed by calculating the average percent recoveries of 1 µg/L and 10 µg/L MC solutions. SPE was performed using three cartridges for each concentration and analyzed in triplicate by both LC-orbitrap-MS and LC-QqQ-MS/MS. Matrix-matched controls were prepared using the same sample preparation and SPE procedures, but MCs were spiked in redissolved samples after SPE. Detailed LC-MS results are shown in Table 8. The average recovery range for all MCs was found to be 90.0-104.8% using both instruments and RSDs were ≤5.0%, which shows accurate and precise extraction of MCs from serum.

TABLE 8

Percent recoveries and RSDs of MCs after SPE purification of solutions containing 1 µg/L and 10 µg/L of six MCs in human serum analyzed using HPLC-orbitrap-MS

| Concentration (µg/L) | MC Variant | Cartridge 1 Recovery (%) | Cartridge 1 RSD (%) | Cartridge 2 Recovery (%) | Cartridge 2 RSD (%) | Cartridge 3 Recovery (%) | Cartridge 3 RSD (%) |
|---|---|---|---|---|---|---|---|
| 1 | MC-LR | 101.3 | 2.6 | 94.4 | 3.6 | 99.4 | 4.3 |
|   | MC-RR | 97.3 | 4.7 | 102.2 | 3.0 | 104.8 | 3.7 |
|   | MC-LA | 98.9 | 5.0 | 99.2 | 2.1 | 101.1 | 2.1 |
|   | MC-LF | 92.8 | 2.9 | 94.3 | 2.9 | 93.6 | 3.6 |
|   | MC-LW | 90.9 | 2.5 | 95.8 | 4.0 | 92.1 | 3.2 |
|   | MC-YR | 96.4 | 3.4 | 100.5 | 3.2 | 100.2 | 1.9 |
|   | MC-IS | 97.4 | 3.4 | 99.0 | 3.3 | 95.9 | 2.0 |
| 10 | MC-LR | 92.1 | 1.4 | 92.8 | 3.8 | 93.7 | 2.9 |
|   | MC-RR | 95.8 | 1.5 | 94.2 | 2.6 | 90.7 | 0.7 |
|   | MC-LA | 94.2 | 1.9 | 96.1 | 2.9 | 90.0 | 4.5 |
|   | MC-LF | 99.6 | 2.1 | 99.4 | 2.7 | 95.8 | 1.2 |
|   | MC-LW | 100.2 | 2.4 | 97.9 | 4.0 | 93.3 | 2.7 |
|   | MC-YR | 100.2 | 3.2 | 93.7 | 2.1 | 97.9 | 2.4 |
|   | MC-LS-IR | 97.4 | 3.4 | 99.0 | 3.3 | 95.9 | 2.0 |

Quantification of MCs Extracted from Human Serum

Quantification of MCs extracted from serum was evaluated by constructing matrix-matched internal calibration curves (Table 9). The calibration curve range for MC-LR, MC-RR, and MC-YR was from 0.5 µg/L to 20 µg/L, and for MC-LA, MC-LW, and MC-LF, the range was from 1 µg/L to 20 µg/L. Calibration curves had $R^2 \geq 0.9953$ for MC-LR, MC-RR, and MC-YR, and $R^2 \geq 0.9883$ for MC-LA, MC-LW, and MC-LF. This difference may arise because the internal standard is more suitable for the quantification of MC-LR, MC-RR, and MC-YR, as discussed above. The LODs and LOQs for MC-LR, MC-RR, and MC-YR were ~0.08 µg/L and ~0.3 µg/L, respectively, while the LODs and LOQs for MC-LA, MC-LW, and MC-LF were ~0.3 µg/L and ~1.0 µg/L (Table 9).

TABLE 9

Calibration curve equations, $R^2$ values, LODs, and LOQs for MC-spiked serum samples

| MC variant | Equation of calibration curve | $R^2$ | LOD (µg/L) | LOQ (µg/L) |
|---|---|---|---|---|
| MC-LR | y = 0.3639x + 0.0069 | 0.9974 | 0.08 | 0.30 |
| MC-RR | y = 1.2167x + 0.0602 | 0.9955 | 0.08 | 0.30 |
| MC-LA | y = 0.3182x + 0.0025 | 0.9926 | 0.30 | 1.00 |
| MC-LF | y = 0.1451x + 0.0053 | 0.9883 | 0.30 | 1.00 |
| MC-LW | y = 0.219x − 0.0016 | 0.9935 | 0.30 | 1.00 |
| MC-YR | y = 0.2911x + 0.0056 | 0.9953 | 0.08 | 0.30 |

To validate the method, MCs were quantified in spiked human serum samples at four concentration levels (1 µg/L, 2.5 µg/L, 5.0 µg/L, and 10.0 µg/L). The calculated concentrations, percent errors, and RSDs are listed in Table 10. The errors were ≤12.9% at 1.0 µg/L concentration level of MCs, which was similar to the results reported for quantification of MCs in plasma samples. At higher concentrations, error was ≤8.0%. Low RSDs (≤7.2%) indicate the excellent precision of the method. Therefore, the developed methods can be used to accurately quantify MCs in human serum samples

TABLE 10

Validation of calibration curves for quantification of MCs in spiked human serum

| Actual concentration (µg/L) | MC variant | Measured concentration (µg/L) | RSD (%) | Error (%) |
|---|---|---|---|---|
| 1.0 | MC-LR | 1.05 | 3.2 | 4.8 |
|   | MC-RR | 1.05 | 2.2 | 5.0 |
|   | MC-LA | 1.10 | 6.5 | 10.3 |
|   | MC-LF | 1.10 | 6.8 | 10.5 |
|   | MC-LW | 1.16 | 4.1 | 12.9 |
|   | MC-YR | 1.08 | 2.0 | 7.8 |
| 2.5 | MC-LR | 2.65 | 5.1 | 5.9 |
|   | MC-RR | 2.65 | 1.8 | 5.9 |
|   | MC-LA | 2.70 | 3.6 | 7.8 |
|   | MC-LF | 2.69 | 6.9 | 7.8 |
|   | MC-LW | 2.75 | 7.2 | 8.0 |
|   | MC-YR | 2.67 | 2.8 | 6.9 |
| 5.0 | MC-LR | 5.23 | 3.1 | 4.6 |
|   | MC-RR | 5.24 | 2.0 | 4.8 |
|   | MC-LA | 5.25 | 2.2 | 4.9 |
|   | MC-LF | 5.21 | 3.4 | 4.2 |

TABLE 10-continued

Validation of calibration curves for quantification of MCs in spiked human serum

| Actual concentration (μg/L) | MC variant | Measured concentration (μg/L) | RSD (%) | Error (%) |
|---|---|---|---|---|
| | MC-LW | 5.25 | 4.6 | 5.0 |
| | MC-YR | 5.20 | 3.4 | 4.0 |
| 10.0 | MC-LR | 10.29 | 1.8 | 2.9 |
| | MC-RR | 10.28 | 1.3 | 2.8 |
| | MC-LA | 10.37 | 1.4 | 3.7 |
| | MC-LF | 10.27 | 2.7 | 2.7 |
| | MC-LW | 10.34 | 5.1 | 3.4 |
| | MC-YR | 10.29 | 3.1 | 2.9 |

Quantification of MC-LR in Plasma of Mice Treated with MC-LR

Figure 24:
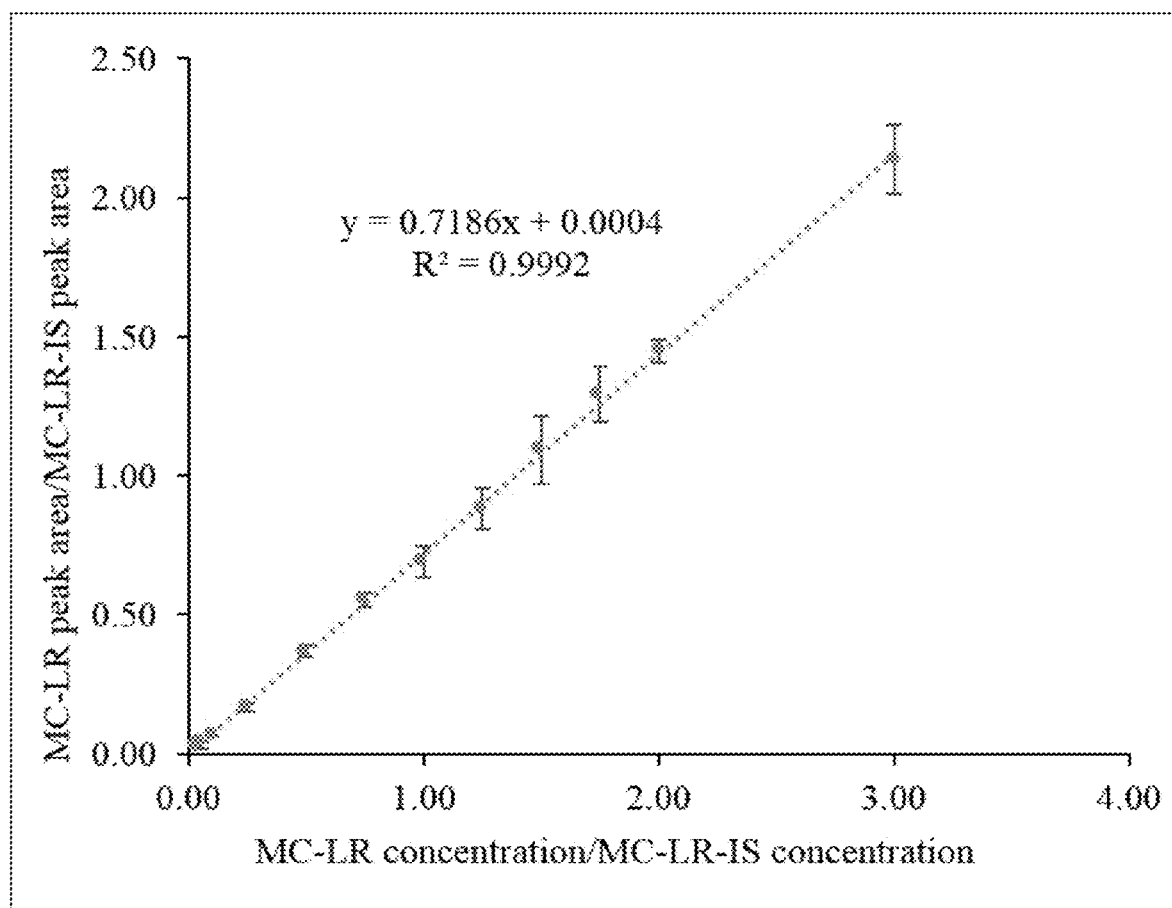
Figure 25:
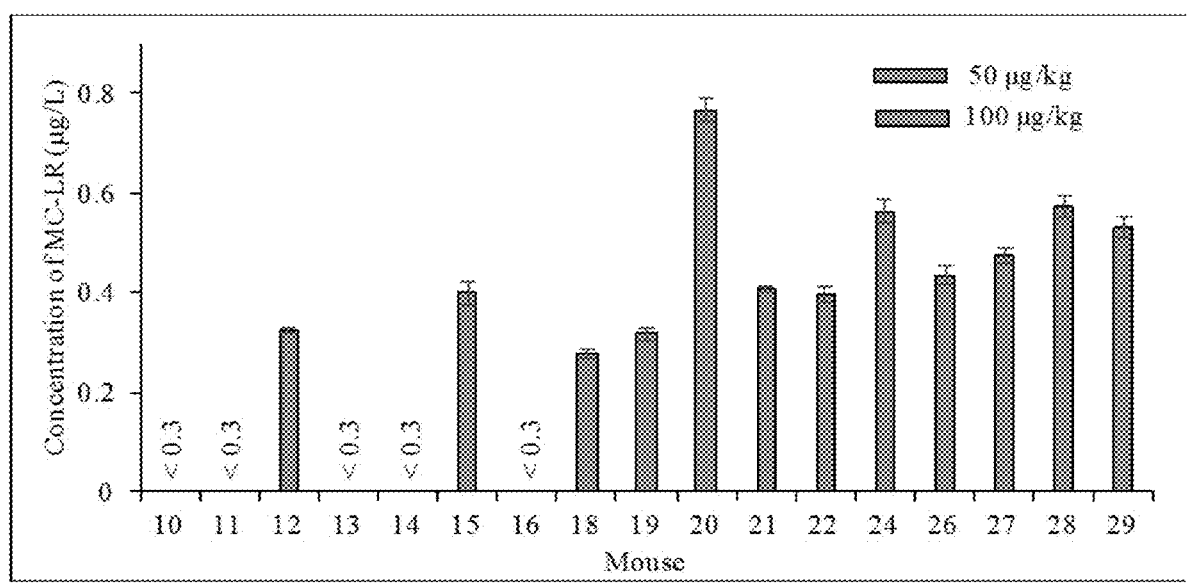

The developed method was applied to quantify MC-LR using plasma samples collected from mice that had been orally administered MC-LR by gavage for five weeks. Experiments started with 29 mice, but mice 17, 23, and 25 perished before data could be collected at the 5-week study end-point. The 26 surviving mice were divided into three groups. Mice 1-9 (n=9) were kept as controls, mice 10-19 (n=9) received 50 μg/kg MC-LR, and mice 20-29 (n=8) received 100 μg/kg MC-LR. Plasma samples were collected at the end of the period. Sample preparation and SPE were performed on plasma samples as detailed above. Samples were analyzed using LC-orbitrap-MS. Matrix-matched internal standard calibration curves were prepared for quantification (FIG. 24). The calibration curve was linear ($R^2 \geq 0.9992$) in the range 0.25 μg/L to 30 μg/L. The concentrations of MC-LR in the analyzed plasma samples are listed in Table 11 and trends are shown in FIG. 25. MC-LR was not detected in control samples. The mice administered 50 μg/kg MC-LR had average MC-LR concentrations of 0.33 μg/L as quantified in four out of nine plasma samples, while the mice administered 100 μg/kg MC-LR had average MC-LR concentrations of 0.52 μg/L (n=8). These results indicate that higher amounts of MC-LR exposure leads to higher levels of MC-LR in plasma. It should also be noted that the $Lepr^{db}/J$ mouse strain used in this proof-of-concept study is a genetic model of non-alcoholic fatty liver disease (NAFLD), and this background may affect plasma levels of MC-LR. Importantly, the MC-LR doses administered were close to the currently accepted NOAEL, suggesting that even low levels of MC-LR exposure may be measured with this methodology.

TABLE 11

Concentration of MC-LR after oral administration in mouse plasma samples

| Mouse | Spiked MC-LR amounts | Gavage time (h) | MC-LR concentration (μg/L) | RSD (%) |
|---|---|---|---|---|
| 10 | 50 μg/kg | 2 | D | — |
| 11 | | 2 | D | — |
| 12 | | 2 | 0.32 | 1.88 |
| 13 | | 2 | D | — |
| 14 | | 4 | D | — |
| 15 | | 4 | 0.40 | 5.60 |
| 16 | | 4 | D | — |
| 18 | | 4 | 0.28 | 3.81 |
| 19 | | 4 | 0.32 | 3.64 |
| 20 | 100 μg/kg | 2 | 0.77 | 3.05 |
| 21 | | 2 | 0.41 | 1.15 |
| 22 | | 2 | 0.40 | 3.62 |
| 24 | | 2 | 0.56 | 3.94 |
| 26 | | 4 | 0.43 | 4.40 |
| 27 | | 4 | 0.47 | 3.23 |
| 28 | | 4 | 0.57 | 3.48 |
| 29 | | 4 | 0.53 | 3.71 |

D: Detected below quantification limit

General Considerations of Developed Methods

Since MCs were extracted from 40 μL aliquots of mouse plasma or human serum and reconstituted using 200 μL of solvent, the sample was diluted 2.5× before injection. The LODs and LOQs of MCs in those biofluids can be improved by increasing the sample volume, and preconcentration will result in improved sensitivity. This is especially significant for human samples, where it is easier to obtain greater volumes of plasma or serum. Concentration levels relevant to human health are ≤0.16 μg/L. Such levels can be achieved using sample preconcentration along with the developed sample preparation and SPE-LC-MS methods.

Conclusions

Sensitive, accurate, and reproducible sample preparation and SPE methods were developed through stepwise optimization in order to extract six common MCs from spiked mouse plasma and human serum. High SPE recoveries with low RSDs for extraction of MCs from mouse plasma and human serum show that the developed methods are accurate and precise. The established method consumes only 40 μL of plasma or serum for extraction of MCs and their subsequent detection at ng/L concentrations. LODs and LOQs can be improved by increasing sample volume. The optimized methods were applied to quantify MC-LR in mice that were orally administrated MC-LR. The results indicated that increasing levels of MC-LR concentration in plasma can be attributed to greater MC-LR exposure.

Example 4—Development and Application of SPE and LC-MS/MS Methods for Quantification of Microcystins in Urine Sensitive, accurate, and reproducible methods for the rapid quantification of six microcystins (MCs; MC-LR, MC-YR, MC-RR, MC-LA, MC-LF, and MC-LW) in mouse urine were developed using solid-phase extraction (SPE) and ultra-high performance liquid chromatography-triple quadrupole-tandem mass spectrometry (UHPLC-QqQ-MS/MS). High recoveries and low relative standard deviations (RSDs) show that the developed methods were accurate and precise. MCs were quantified with limits of detection (LODs) and quantification (LOQs) in ng/L concentrations in spiked urine samples using UHPLC-QqQMS/MS. The methods were applied to quantify MC-LR in urine of mice administered MC-LR. While MCs in urine have been quantified previously using ELISA and HPLC-UV-Vis, this example describes an SPE-LC-MS procedure.

Enzyme-linked immunosorbent assay (ELISA) may be used to quantify MCs in urine. ELISA has the advantage of being faster, easier, and cheaper than SPE-LC-MS. However, ELISA has higher RSDs as well as LODs and LOQs, cannot distinguish between different MCs, and generally does not account for matrix effects in complex samples such as urine. Furthermore, there is no commercially available ELISA kit specific for quantification of MCs in urine. HPLC-UV-Vis has been used to quantify MCs in urine through an indirect quantification of MCs.

ELISA detects MCs by binding the ADDA moiety present in all MCs using an antibody. ELISA cannot distinguish between MCs and ADDA fragments and therefore tends to overreport MC concentration. SPE-LC-MS/MS first extracts MCs from urine using SPE. The MCs are then separated by LC and analyzed with MS/MS. Quantification is achieved by measuring the peak areas in the chromatogram. SPE-LC-MS allows for accurate, sensitive, and reproducible quantification of the MCs with excellent LODs, LOQs, and RSDs.

Microcystins (MCs) are cyanobacterial toxins that cause a variety of human and animal health effects worldwide. Symptoms related to MCs have been sporadically reported for decades, and sensitive and precise analytical strategies for MC quantification in biofluids are important to detect prolonged exposure to MCs. In this example, a solid-phase extraction (SPE) of six MCs (MC-LR, MC-RR, MC-LA, MC-LF, MC-LW, and MC-YR) from mouse urine is described, along with their quantification by ultra-high performance liquid chromatography-triple quadrupole-tandem mass spectrometry (UHPLC-QqQ-MS/MS). Detection and quantification of MCs in urine was also achieved using HPLC-orbitrap-MS in selected-ion monitoring (SIM) mode. Under optimal extraction conditions, the extraction recoveries of MCs from urine samples spiked at two different concentrations (1 μg/L and 10 μg/L) were in the range from 90.4% to 104.3% with RSDs ≤4.7%. Internal standard calibration curves were linear with $R^2 \geq 0.9950$ for MC-LR, MC-RR, and MC-YR, and $R^2 \geq 0.9916$ for MC-LA, MC-LF, and MC-LW. MCs were quantified with LODs and LOQs in ng/L concentrations in spiked urine samples using both systems. The developed methods were applied to quantify urinary concentrations of MC-LR after oral administration to mice. Mice that were administered 50 μg of MC-LR per kg bodyweight had average urine MC-LR concentrations of 1.30 μg/L (n=8), while mice that were administered 100 μg of MC-LR per kg bodyweight had average MC-LR concentrations of 2.82 μg/L (n=8) in urine samples. Increased MC-LR dosage led to larger amounts of MC-LR in mouse urine. The results showed that the developed methods were rapid and effective for the quantification of MCs in mouse urine.

Harmful algal blooms (HABs) occur in eutrophic bodies of water when cyanobacteria proliferate immensely. Such blooms are increasingly common and are likely due to increased nitrate and phosphate concentrations from sewage or fertilizer runoff. They can cause aquatic hypoxia and create dead zones in the water, often irreversibly destroying delicate ecosystems. Furthermore, many of the cyanobacteria in HABs produce toxins, such as microcystins (MCs), that can contribute to the mortality of fish in affected areas. MCs can travel up the food chain and impact an area far greater than their initial purview. HABs directly affect humans when they develop in water bodies used for drinking water or recreation. During the summer of 2014, a cyanobacterial bloom in the Western Lake Erie Basin released MCs into water used for the city of Toledo, Ohio, a state of emergency was declared, and residents were told to not drink the tap water.

MCs are toxic cyclic heptapeptides that include the characteristic amino acid ADDA (3-amino-9-methoxy-2,6,8-trimethyl-10-phenyldeca-4,6-dienoic acid). MCs primarily affect the liver and can cause cancer, hemorrhage, or failure of the organ. There were fifty human deaths when MC-contaminated water was used for the hemodialysis of 130 patients in 1996 in Caruaru, Brazil. The WHO suggests that MC levels in purified drinking water should be below 1 μg/L for safe consumption. However, the EPA recommends no more than 0.3 μg/L for young children, and levels lower than 0.160 μg/L were found in the serum of the deceased patients in Brazil.

MCs commonly enter the body through ingestion and inhalation. Previous studies have detected MCs in the blood, liver, kidney, intestines, feces, and urine of infected. MC levels in plasma or serum are often used to assess MC exposure, and most studies have been associated with the detection and quantification of MCs in human, rat, and mouse plasma and serum. MCs have been detected in urine using enzyme-linked immunosorbent assays (ELISA). ADDA-ELISA uses a colorimetric method to quantify the binding of MCs with an anti-ADDA antibody and report any attached ADDA moiety as an MC-LR equivalent with relative standard deviation (RSD)<15%. Commercially available kits can detect MCs in water or serum, but there are no kits specialized for quantification of MCs in urine.

LC-MS is a powerful detection tool with the advantage of being able to separate and identify different MC congeners, and can be used for accurate and precise quantification of MCs in urine. However, it is necessary to develop a purification method to attain low limits of detection (LODs) and quantification (LOQs) of MCs in complex matrices such as urine. Solid-phase extraction (SPE) is a common method for purification of MCs from water and biofluids, and has been used to extract MCs as well as other toxins from urine. However, an SPE-LC-MS method specifically developed for the purification and quantification of MCs from urine has not been reported. A method tailored for the unique urine profile may improve the detection sensitivity and the LOQ of MCs.

In this example, an SPE method was developed to extract six commons MCs (MC-LR, MC-RR, MC-YR, MC-LA, MC-LF, and MC-LW) from mouse urine. An UHPLC-triple quadrupole (QqQ)-MS/MS method was also developed for their sensitive and reproducible quantification. These techniques, along with the HPLC-orbitrap-MS method described herein, were used to create calibration curves for the quantification of MCs with LOQs ≤0.13 μg/L. The methods were applied to quantify MC-LR in the urine of mice that had been orally administered MC-LR.

Experimental

Reagents

MCs were obtained as analytical standard solutions (500 mg/L of MC-LR, 500 mg/L of MC-LA, and 100 mg/L of MC-RR) from Cayman Chemical Company (Ann Arbor, Mich., USA). MC-LW, MC-LF, and MC-YR were purchased as solids from Enzo Life Sciences (Farmingdale, N.Y., USA). 25 μg of $C_2D_5$-monoethyl ester MC-LR (MC-IS, Cambridge Isotope Laboratories, Tewksbury, Mass., USA) was dissolved in 250 μL of methanol and used as an internal standard for quantification of MC-LR. LC-MS- and HPLC-grade acetonitrile, methanol, and water were purchased from Fisher Scientific (Pittsburgh, Pa., USA). Reagent-grade (≥95%) formic acid (FA) was obtained from Sigma (St. Louis, Mo., USA).

Materials and Instruments

Sep-Pak C18 Plus Light SPE Cartridges with 130 mg sorbent beds were from Waters (Milford, Mass., USA), and 3 mL and 10 mL syringes were purchased from Becton, Dickinson and Company (Franklin Lakes, N.J., USA). 2 mL clear glass vials and glass inserts were obtained from Sigma (St. Louis, Mo., USA). The heated vacuum concentrator was from Eppendorf (Hamburg, Germany).

MCs were separated and quantified using both UHPLC-QqQ-MS/MS and HPLC-orbitrap-MS systems. A Shimadzu LCMS-8050 system (Columbia, Md., USA) was used for UHPLC-QqQ-MS/MS analysis. The UHPLC consisted of two LC-20AD XR pumps, two DGU-20A3R degasser units, a SIL-20AC XR autosampler, a CTO-20A column oven, and a CBM-20A system controller. The column was an Acquity HSS T3 C18 column (3.0×50 mm, 1.8 μm, Waters). An HSS T3 guard column (2.1×5 mm, 1.8 μm, Waters) was used.

The HPLC (Shimadzu Technologies, Addison, Ill., USA) was equipped with two LC-20AD pumps, a DGU-20A3 degasser, a SIL-20A HT autosampler, and a CBM-20A system controller. HPLC separation was performed using a reversed-phase XBridge C8 column (3.0×100 mm, 3.5 μm, Waters, Milford, Mass.) with a C8 guard column (3.0×20 mm, 3.5 μm, Waters, Milford, Mass.). The MS consisted of an Orbitrap Fusion Tribrid mass spectrometer with an electrospray ionization (ESI) source (Thermo Fisher Scientific, San Jose, Calif., USA).

SPE and Urine Sample Preparation 1 mg/L standard solutions of each MC (MC-LR, MC-RR, MC-LA, MC-LF, MC-LW, MC-YR, and MC-IS) were prepared in methanol. MCs were mixed and diluted with water to prepare appropriate spiked concentrations of MCs. For SPE optimization experiments, recovery experiments, and quantification using internal standard calibration, urine samples were spiked with the MC mixture.

Control mouse urine samples were stored at −80° C., thawed to room temperature, and vortexed. For extraction of MCs from mouse urine, 80 μL of urine was transferred into a 50 mL centrifuge tube, spiked with the MC mixture, and diluted to 2 mL with HPLC-grade water. The SPE cartridge was conditioned with 2 mL of 90:10 methanol:water (v/v) containing 0.1% FA and equilibrated with 2 mL of 0.1% FA. The sample was loaded onto the cartridge and washed with 2 mL of 0.1% FA. MCs were eluted with 1.75 mL of 90:10 acetonitrile:water (v/v) containing 0.1% FA. The solvent was evaporated using a vacuum concentrator and the residue was redissolved in 200 μL of 90:10 methanol:water (v/v) containing 0.1% FA for LC-MS analyses.

Mouse Urine Collection and Sample Preparation

All animal experiments were conducted in accordance with the National Institutes of Health Guide for the Care and Use of Laboratory Animals using protocols approved by the University of Toledo, Health Science Campus, Institutional Animal Use and Care Committee. Ten week old male Lepr[db]/J mice weighing 40-45 g were obtained from Jackson Laboratories and gavaged with vehicle (300 μL of 0.9% saline), 50 μg MC-LR per kg bodyweight (50 μg/kg MC-LR), or 100 μg/kg MC-LR for five weeks. These doses approximate the currently accepted no observed adverse effect level (NOAEL) of 40 μg/kg established after 13 week MC-LR administration. Mice were placed into metabolic cages (Harvard Apparatus, Holliston, Mass., USA) immediately after the final MC-LR administration for collection of 24-hour urine samples. Samples were frozen at −80° C. immediately after collection and thawed to room temperature prior to extraction. Samples were vortexed and 80 μL of urine was spiked with a constant amount of MC-IS (4 μL of 100 μg/L solution). MC-LR calibration standards were prepared in control mice urine in the range of 0.125 to 15 μg/L by spiking different amounts of MC-LR and a constant amount of internal standard (4 μL of 100 μg/L solution). Both urine samples and calibration standards were diluted to 2 mL with water. SPE was performed on the samples and calibration standards using the optimized methods. The samples were analyzed in triplicate on the LC-QqQ-MS/MS and LC-orbitrap-MS systems.

Liquid Chromatographic and Mass Spectrometric Conditions

HPLC-QqQ-MS/MS Operating Conditions

Mobile phase A consisted of 0.1% FA in water and mobile phase B was acetonitrile containing 0.1% FA. The column oven temperature was 45° C. and the sample injection volume was 20 μL. A 0.4 mL/min flow rate was used and the column was equilibrated with 10% B prior to injection. The ten-minute optimized gradient started at 10% B and was increased to 25% B in 0.05 minutes, increased to 95% B in 4.75 minutes, maintained at 95% B for 0.2 minutes, and re-equilibrated at 10% B for 4.99 minutes.

ESI was used with LC-MS/MS in positive-ion multiple reaction monitoring (MRM) mode for the identification and quantification of MCs. The monitoring parameters were optimized as follows: ion source spray voltage, 4 kV; conversion dynode, 10.0 kV; detector voltage, 1.96 kV; interface temperature, 300° C.; desolvation line temperature, 125° C.; heatblock temperature, 400° C.; nebulizing gas flow rate, 2.0 L/min; drying gas flow rate, 10.0 L/min; heating gas flow rate, 10.0 L/min; Ar pressure in the collision-induced dissociation cell, 270 kPa. The first and third quadrupoles (Q1 and Q3) were set to unit resolution and the loop time and dwell time were 0.424 s and 50.0 msec, respectively. Seven MRM channels were used per run for MC-LR, MC-RR, MC-LF, MC-LW, MC-YR, MC-LA, and MC-IS. MRM transitions, Q1 pre bias voltages, Q3 pre bias voltages, and collision energies (CEs) for all MCs are shown in Table 12. The data were processed using Lab Solutions (Shimadzu) software and MRM peak areas were used for quantification.

TABLE 12

| | QqQ-MS/MS parameters | | | |
|---|---|---|---|---|
| MC variant | MRM transition | Q1 pre bias (V) | CE (V) | Q3 pre bias (V) |
| MC-LR | 995.50 → 135 | −22 | −55 | −26 |
| MC-RR | 519.90 → 135 | −26 | −32 | −26 |
| MC-LF | 986.40 → 135 | −22 | −51 | −26 |
| MC-LW | 1025.45 → 135 | −38 | −54 | −14 |
| MC-YR | 1045.55 → 135 | −30 | −55 | −30 |
| MC-LA | 910.60 → 135 | −34 | −53 | −22 |
| MC-IS | 1028.50 → 135 | −38 | −33 | −15 |

HPLC-Orbitrap-MS Operating Conditions

MCs extracted from urine were quantified using our previously developed HPLC-orbitrap-MS method. Briefly, the mobile phases consisted of 0.05% FA in water (mobile phase A) and acetonitrile containing 0.05% formic acid (mobile phase B). The flow rate was 0.3 mL/min. The column was equilibrated with 20% B for 30 minutes prior to initial injection. The gradient started with 20% B and was increased to 60% B in 2 minutes, to 70% B in 5 minutes, and to 90% B in 5 minutes, and then was decreased to 20% B in 2 minutes and maintained for 6 minutes. The total run time was 20 min and the sample injection volume was 20 μL.

ESI with selected-ion monitoring (SIM)-MS in positive ion mode was used for quantification of MCs as described above. MS and MS/MS were performed simultaneously and higher-energy collision-induced dissociation (HCD) was used to fragment MC precursor ions. MS ions were detected using the orbitrap mass analyzer and fragment ions were analyzed with a linear ion trap mass analyzer. Seven SIM channels were monitored per run for quantification: six for the singly-charged protonated ions ([M+H]$^+$) of MC-LR (m/z 995.56), MC-LA (m/z 910.49), MC-LW (m/z 1025.53), MC-LF (m/z 986.52), MC-YR (m/z 1045.54), and MC-IS (m/z 1028.62); and one for the doubly-charged protonated ([M+2H]$^{2+}$) ion of MC-RR (m/z 519.79). All samples were analyzed in triplicate. MS data was acquired and analyzed using Xcalibur software (Thermo Scientific) and the extracted-ion chromatogram (EIC) peak areas of monoisotopic MC ions were used for quantification.

LODs, LOQs, and Recovery Determination

All samples were analyzed using both UHPLC-QqQ-MS/MS and HPLC-orbitrap-MS systems. Experimental LODs and LOQs were obtained by detecting MC ions with signal-to-noise ratios of ~3 and 10, respectively. Relative abundances of the MC ions were compared to select the optimum SPE and sample preparation steps. Recoveries of the SPE method were calculated by comparing the MRM and EIC peak areas of corresponding MC ions in the extracted samples and controls using LC-QqQ-MS/MS and LC-orbitrap-MS, respectively.

Results and Discussion

General Considerations

A precise and accurate method using UHPLC-QqQ-MS/MS was developed to separate and quantify MCs in urine. The chromatograms of urine extracts containing MCs obtained in MRM mode are shown in FIGS. 26A-26F. Baseline separation of the seven MCs was achieved in 4.15 minutes using UHPLC, with retention times of 2.05 (MC-RR), 2.41 (MC-YR), 2.49 (MC-LR), 2.76 (MC-IS), 3.43 (MC-LA), 3.86 (MC-LW), and 4.01 (MC-LF) minutes (FIGS. 26A-26F). MRM transitions to fragment ion with m/z 135 were detected for all MC precursor ions and the peak areas of this fragment were used for data calculations. The HPLC-ESI-SIM-MS method was used for separation and quantification of seven MCs using LC-orbitrap-MS. Briefly, separation of MCs was achieved by HPLC in 9 minutes. The retention times were 6.02 (MC-LR), 5.65 (MC-RR), 5.88 (MC-YR), 7.38 (MC-LA), 8.53 (MC-LF), 8.20 (MC-LW), and 6.36 (MC-IS) minutes. The column equilibration time before the next LC run was 11 minutes. These two methods were used for quantification of MCs in urine samples.

Optimization of the Extraction of MCs from Mouse Urine

SPE protocols require conditioning, equilibration, sample loading, washing, and elution steps. These steps were optimized for the extraction of MCs from mouse urine before the LC-MS analyses. A 90:10 methanol:water (v/v) solution containing 0.1% FA was used to condition and 0.1% FA was used to equilibrate the cartridge based on our previous work to extract MCs from water. To optimize elution, different solvent combinations were tested by changing solvent polarity and acidity (Table 13). For each SPE experiment, 200 pg of each MC was spiked into 80 μL of urine to make 2.5 μg/L concentrations of individual MCs in urine. After elution, samples were evaporated and redissolved in acidified methanol for analyses using both LC-QqQ-MS/MS and LC-orbitrap-MS. Relative abundances of the MC ions were compared to obtain the best elution solvent. 90:10 acetonitrile:water (v/v) containing 0.1% FA showed the highest relative abundances of MC ions using both LC-MS systems (FIG. 27) and was chosen as the elution solvent. 90:10 methanol:water with 0.1% FA, the most polar solvent, showed the lowest signal response for all MCs. This indicates that MCs are more soluble in moderately polar solvents.

TABLE 13

Solvent compositions used for optimization of the elution of MCs from mouse urine samples

| Solvent composition | Elution solvent |
|---|---|
| S-1 | Acetonitrile |
| S-2 | Methanol |
| S-3 | Acetonitrile + 0.1% FA |
| S-4 | Methanol + 0.1% FA |
| S-5 | 90:10 Methanol:water + 0.1% FA |
| S-6 | 90:10 Acetonitrile:water + 0.1% FA |

Determination of Percent Recovery of MCs from Mouse Urine

After finding the optimal elution solvent, percent recoveries were calculated for the extraction of each MC from mouse urine. Recoveries were calculated by comparing LC-MS and LC-MS/MS signal responses of MCs in the samples to the signal responses of control samples. Accuracy and reproducibility of the SPE method was determined by using three SPE cartridges for 1 μg/L and 10 μg/L MC concentrations. SPE was performed using the optimized method and the samples were analyzed in triplicate by both LC-QqQ-MS/MS and LC-orbitrap-MS. Controls were prepared by diluting 80 μL of urine to 2 mL with HPLC-grade water and performing SPE. After evaporation and redissolution, MCs were spiked in control samples. Average MC recoveries were calculated from three LC-MS replicates of each concentration using independent cartridges (Table 14). Recoveries for all MCs analyzed on QqQ-MS/MS ranged from 91.2-102.2% with RSDs ≤4.5% (Table 14). Table S1 summarizes the recoveries and RSDs using LC-orbitrap-MS. Recoveries for all MCs in urine at both concentration levels ranged from 90.4-104.3% and RSDs were ≤4.7%. Low RSDs and high average recoveries confirmed the good reproducibility and accuracy of the MC extraction method.

TABLE 14

Percent recoveries and RSDs of seven MCs after their extraction from in mouse urine containing 1 μg/L and 10 μg/L of each MC, obtained using UHPLC-QqQ-MS/MS

| | | Cartridge 1 | | Cartridge 2 | | Cartridge 3 | |
|---|---|---|---|---|---|---|---|
| Concentration (μg/L) | MC Variant | Recovery (%) | RSD (%) | Recovery (%) | RSD (%) | Recovery (%) | RSD (%) |
| 1 | MC-LR | 95.5 | 2.0 | 100.1 | 1.4 | 99.5 | 1.6 |
| | MC-RR | 96.0 | 2.2 | 100.8 | 2.8 | 100.4 | 2.5 |
| | MC-LA | 98.6 | 2.5 | 97.4 | 1.9 | 97.4 | 3.8 |
| | MC-LF | 95.4 | 2.3 | 97.3 | 0.9 | 99.6 | 0.5 |
| | MC-LW | 93.7 | 2.2 | 96.8 | 3.0 | 96.7 | 2.9 |
| | MC-YR | 97.1 | 2.4 | 91.2 | 1.1 | 95.6 | 4.0 |
| | MC-IS | 100.9 | 1.7 | 102.2 | 1.5 | 98.9 | 2.9 |

TABLE 14-continued

Percent recoveries and RSDs of seven MCs after their extraction from in mouse urine containing 1 μg/L and 10 μg/L of each MC, obtained using UHPLC-QqQ-MS/MS

| Concentration (μg/L) | MC Variant | Cartridge 1 | | Cartridge 2 | | Cartridge 3 | |
|---|---|---|---|---|---|---|---|
| | | Recovery (%) | RSD (%) | Recovery (%) | RSD (%) | Recovery (%) | RSD (%) |
| 10 | MC-LR | 95.8 | 2.5 | 93.5 | 2.6 | 94.4 | 3.6 |
| | MC-RR | 91.6 | 2.1 | 95.0 | 3.8 | 92.9 | 1.5 |
| | MC-LA | 100.3 | 3.1 | 100.2 | 3.4 | 99.1 | 3.4 |
| | MC-LF | 94.3 | 3.8 | 94.4 | 2.2 | 93.5 | 3.3 |
| | MC-LW | 97.3 | 2.8 | 98.4 | 2.5 | 100.8 | 3.2 |
| | MC-YR | 96.9 | 3.5 | 95.9 | 4.5 | 96.6 | 1.8 |
| | MC-IS | 97.4 | 2.6 | 95.9 | 2.4 | 96.2 | 3.0 |

Quantification of MCs in Spiked Mouse Urine Samples

The accuracy of the method for quantification of MCs in mouse urine was tested by constructing internal standard calibration curves for each MC in the concentration range from 0.25 μg/L to 10.0 μg/L. Calibration standards were prepared by spiking different amounts of the MCs into 80 μL of urine. Samples were analyzed using HPLC-orbitrap-MS and UPLC-QqQ-MS/MS in triplicate. Calibration curves showed excellent linearity ($R^2 \geq 0.9950$) for MC-LR, MC-RR, and MC-YR (Table 15 and Table 16), with LODs and LOQs of ~0.05 μg/L and ~0.13 μg/L, respectively. The $R^2$ values of calibration curves for quantification of MC-LA, MC-LF and MC-LW were ≥0.9916, with LODs and LOQs of ~0.08 μg/L and ~0.25 μg/L, respectively. Similar LOQs were observed using the UHPLC-QqQ-MS/MS system while LODs slightly improved. Small deviations may be due to differences in ionization or the MRM process of the QqQ system.

TABLE 15

Internal standard calibration curve equations, $R^2$ values, LODs, and LOQs for MC-spiked urine samples analyzed using UHPLC-QqQ-MS/MS

| MC variant | Equation of calibration curve | $R^2$ | LOD (μg/L) | LOQ (μg/L) |
|---|---|---|---|---|
| MC-LR | y = 0.8494x + 0.0675 | 0.9952 | 0.05 | 0.13 |
| MC-RR | y = 1.1238x + 0.3247 | 0.9970 | 0.05 | 0.13 |
| MC-LA | y = 0.5089x + 0.0223 | 0.9938 | 0.13 | 0.50 |
| MC-LF | y = 0.4446x + 0.0054 | 0.9916 | 0.14 | 0.50 |
| MC-LW | y = 0.4321 + 0.0144 | 0.9934 | 0.13 | 0.50 |
| MC-YR | y = 0.4145x + 0.0429 | 0.9950 | 0.05 | 0.13 |

TABLE 16

Internal standard calibration curve equations, $R^2$ values, LODs, and LOQs for MC-spiked urine samples analyzed using HPLC-orbitrap-MS

| MC variant | Equation of calibration curve | $R^2$ | LOD (μg/L) | LOQ (μg/L) |
|---|---|---|---|---|
| MC-LR | y = 0.9973x + 0.0381 | 0.9981 | 0.06 | 0.13 |
| MC-RR | y = 0.911x + 0.0279 | 0.9965 | 0.06 | 0.13 |
| MC-LA | y = 0.8034x + 0.0857 | 0.9965 | 0.13 | 0.50 |
| MC-LF | y = 0.9425x + 0.0465 | 0.9947 | 0.15 | 0.50 |
| MC-LW | y = 0.5797x + 0.0706 | 0.9939 | 0.15 | 0.50 |
| MC-YR | y = 0.7118x + 0.1759 | 0.9961 | 0.06 | 0.13 |

Calibration curves were validated using spiked samples with 0.5 μg/L, 1.0 μg/L, 2.5 μg/L, and 5.0 μg/L MC concentrations. For MCs at 0.5 μg/L and 1.0 μg/L concentrations, the errors were ≤10.6% and had RSDs ≤7.5% (Table 17). At 2.5 μg/L and 5.0 μg/L MC concentrations, the errors were ≤4.5% with RSDs ≤6.9%. Low percent errors and RSDs at all concentration levels indicates that the methods are accurate and precise, and MCs can be quantified in the concentration range shown in the calibration curves.

TABLE 17

Validation of internal standard calibration curves for quantification of MCs in spiked mouse urine

| Actual Concentration (μg/L) | MC Variant | Measured concentration (μg/L) | | RSD (%) | | Error (%) | |
|---|---|---|---|---|---|---|---|
| | | QqQ | orbitrap | QqQ | Orbitrap | QqQ | Orbitrap |
| 0.5 | MC-LR | 0.53 | 0.53 | 6.4 | 4.9 | 1.8 | 5.7 |
| | MC-RR | 0.49 | 0.54 | 1.1 | 7.5 | 1.9 | 8.3 |
| | MC-LA | 0.53 | 0.55 | 3.1 | 4.9 | 1.8 | 9.4 |
| | MC-LF | 0.54 | 0.54 | 7.1 | 7.1 | 7.5 | 8.6 |
| | MC-LW | 0.55 | 0.55 | 1.2 | 7.1 | 9.4 | 10.6 |
| | MC-YR | 0.54 | 0.54 | 2.4 | 5.9 | 7.4 | 7.2 |
| 1.0 | MC-LR | 1.01 | 1.07 | 4.2 | 4.5 | 0.8 | 6.7 |
| | MC-RR | 1.02 | 1.05 | 4.0 | 5.6 | 2.1 | 5.4 |
| | MC-LA | 1.03 | 1.06 | 4.3 | 3.8 | 2.8 | 5.9 |
| | MC-LF | 1.06 | 1.09 | 4.0 | 2.8 | 6.4 | 9.3 |
| | MC-LW | 1.03 | 1.07 | 2.9 | 5.4 | 3.2 | 6.5 |
| | MC-YR | 1.03 | 1.08 | 4.2 | 5.7 | 2.2 | 7.5 |
| 2.5 | MC-LR | 2.53 | 2.55 | 1.3 | 3.8 | 1.3 | 2.1 |
| | MC-RR | 2.07 | 2.47 | 1.2 | 1.5 | 1.2 | 1.1 |
| | MC-LA | 2.57 | 2.58 | 1.7 | 1.8 | 2.6 | 3.1 |
| | MC-LF | 2.60 | 2.58 | 2.5 | 3.5 | 3.9 | 3.1 |
| | MC-LW | 2.56 | 2.61 | 1.2 | 6.9 | 2.2 | 4.5 |
| | MC-YR | 2.50 | 2.56 | 4.4 | 3.6 | 0.2 | 2.4 |
| 5.0 | MC-LR | 5.05 | 5.07 | 2.1 | 1.7 | 1.1 | 1.4 |
| | MC-RR | 5.02 | 5.03 | 2.0 | 2.0 | 0.3 | 0.6 |
| | MC-LA | 5.14 | 5.12 | 2.0 | 3.2 | 2.5 | 2.4 |
| | MC-LF | 5.15 | 5.18 | 2.6 | 3.7 | 2.9 | 3.6 |
| | MC-LW | 5.11 | 5.14 | 1.7 | 3.1 | 2.2 | 2.7 |
| | MC-YR | 4.91 | 5.08 | 3.8 | 3.3 | 1.7 | 1.5 |

When comparing the performance of orbitrap-SIM-MS to QqQ-MS/MS, the SIM chromatogram shows higher background noise, thus increasing the LOD. In contrast, MRM chromatograms had relatively low background and allowed for detection of MC ions at lower concentrations. In the QqQ system, the signal responses for MCs at all concentrations had ≤6.4% RSD while the orbitrap system had ≤7.5% RSD. This indicates that the MC signal responses in the orbitrap were more vulnerable to matrix effects, especially for MCs without the easily-ionizable arginine moiety (MC-LA, MC-LF, MC-LW). Detection and quantification was performed with 5 m/z mass window in orbitrap-MS, and the mass window can be narrowed to minimize matrix effects. However, the results show good selectivity and sensitivity of both MS and MS/MS methods to quantify MCs in mouse urine. The SPE procedure was used to obtain relatively clean extract of MCs, and LODs and LOQs of MCs can be improved by increasing sample volume.

Internal standard calibration curves showed excellent linearity for quantification of MC-LR, MC-RR, and MC-YR ($R^2 \geq 0.9950$) compared to MC-LA, MC-LF and MC-LW ($R^2 \geq 0.9916$). Since the internal standard is ethylated and deuterated MC-LR, it should be the most effective for quantification of MC-LR. MC-IS has more similar properties to MC-RR and MC-YR than to MC-LA, MC-LF, and MC-LW due to the arginine moiety. This may explain the better linearity of calibration curves for quantification of MC-LR, MC-RR, and MC-YR than those for MC-LA, MC-LF, and MC-LW. Additionally, percent errors for quantification of the latter MCs are larger (Table 17).

Quantification of MC-LR in the Urine of Gavaged Mice

The developed method was applied to quantify MC-LR in urine samples collected from mice that were orally administered MC-LR and control mice that were administered 300 µL of 0.9% saline. In total, 26 mouse urine samples were analyzed for MC-LR quantification. Samples were analyzed using HPLC-orbitrap-MS and UHPLC-QqQ-MS/MS. Matrix-matched internal standard calibration curves were prepared for quantification (FIGS. 28A-28B). Calibration curves were linear ($R^2 \geq 0.997$) in the range 0.125 µg/L to 15 µg/L for MC-LR in mouse urine. MC-LR was not detected in the control samples (mice 1-9, n=9). The MC-LR concentrations in the analyzed samples are listed in Table 18 and trends are shown in FIG. 29. Mice 17, 23, and 25 perished before data could be collected at the 5-week study end-point. The mice that were administered 50 µg/kg MC-LR (mice 10-19, n=8) had average MC-LR concentrations of 1.30 µg/L in urine samples. MC-LR was detected in the urine sample of mouse 11 below the quantification limit. The mice that were administered 100 µg/kg MC-LR (mice 20-29, n=8) had 2.82 µg/L in urine. MC-LR excretion in urine was calculated by multiplying the 24-hour urine volume by MC-LR concentration. The average amount of MC-LR excreted by mice 20-29 (3.15 ng) was double the amount of MC-LR excreted by mice 10-19 (1.57 ng). This indicates that higher amounts of MC-LR exposure results in higher levels of MC-LR in urine and might be affected by variable uptake or metabolism of MC-LR.

TABLE 18

Concentration of MC-LR in mouse urine samples. Calibration curves are shown in FIG. 28.

| | | | HPLC-orbitrap-MS | | | UHPLC-QqQ-MS/MS | | |
|---|---|---|---|---|---|---|---|---|
| Mouse | Spiked MC-LR amount | 24-hour urine volume (mL) | MC-LR concentration (µg/L) | RSD | MC-LR excretion (ng/24 hours) | MC-LR concentration (µg/L) | RSD | MC-LR excretion (ng/24 hours) |
| 10 | 50 µg/kg | 1.6 | 1.43 | 2.93 | 2.29 | 1.39 | 3.32 | 1.99 |
| 11 | | 2.8 | D | — | — | D | — | — |
| 12 | | 1.2 | 0.97 | 4.01 | 1.16 | 1.19 | 3.90 | 1.15 |
| 13 | | 1.5 | 1.91 | 2.14 | 2.87 | 2.12 | 3.05 | 4.05 |
| 14 | | 1.6 | 0.72 | 3.00 | 1.15 | 1.17 | 2.42 | 0.85 |
| 15 | | 1.2 | 0.73 | 2.22 | 0.88 | 0.83 | 3.65 | 0.61 |
| 16 | | 0.4 | 1.71 | 1.53 | 0.68 | 1.85 | 2.41 | 3.16 |
| 18 | | 0.4 | 1.63 | 2.64 | 0.65 | 1.52 | 4.01 | 2.48 |
| 19 | | 0.5 | 1.11 | 3.19 | 0.55 | 0.59 | 2.65 | 0.66 |
| 20 | 100 µg/kg | 1 | 2.85 | 2.88 | 2.85 | 3.26 | 2.75 | 3.26 |
| 21 | | 0.9 | 3.91 | 2.72 | 3.52 | 3.35 | 2.89 | 3.01 |
| 22 | | 1.2 | 5.00 | 1.88 | 6.00 | 4.52 | 2.99 | 5.42 |
| 24 | | 1.4 | 2.22 | 2.93 | 3.10 | 2.24 | 3.43 | 3.13 |
| 26 | | 1.8 | 3.09 | 4.17 | 5.55 | 2.31 | 2.85 | 4.15 |
| 27 | | 1.1 | 1.52 | 4.09 | 1.67 | 0.77 | 3.56 | 0.85 |
| 28 | | 0.7 | 3.51 | 2.66 | 2.46 | 2.78 | 3.12 | 1.94 |
| 29 | | 0.9 | 2.05 | 4.21 | 1.85 | 1.79 | 3.23 | 1.61 |

D: detected below the quantification limit <0.13 µg/L

Conclusions

Sensitive, accurate, and reproducible methods for the rapid quantification of six MCs in mouse urine were developed using SPE-UHPLC-QqQ-MS/MS and SPE-LC-orbitrap-MS. High recoveries and low RSDs show that the developed methods were accurate and precise. Only 80 µL of urine were necessary to simultaneously detect and quantify MCs at ng/L concentrations. The method was used to quantify MC-LR in the urine of mice that were orally administrated MC-LR. Higher MC-LR concentrations were found in mice that were given larger doses of MC-LR. Notably, the Lepr$^{db}$/J mouse strain used in this example is a genetic model of non-alcoholic fatty liver disease (NAFLD), and this condition may affect urinary levels of MC-LR. Importantly, this example was designed using MC-LR doses close to the currently accepted NOAEL, indicating that even lower levels of MC-LR exposure may be measured with these methods. These methods are thus useful to quantify MCs and other toxins in the urine of humans and other animals.

Certain embodiments of the methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method for detecting and quantifying a microcystin compound in a sample, the method comprising:
   conditioning a solid-phase extraction cartridge with methanol containing formic acid;
   adding $ZnSO_4$ to a sample of plasma or serum containing a microcystin compound,
   purifying the sample through the solid-phase extraction cartridge to obtain a purified sample,
   conducting a quantitative analysis on the purified sample to quantify the amount of the microcystin compound in the purified sample, wherein the quantitative analysis comprises a liquid chromatography step and a mass spectrometry step; and
   using a calibration curve to determine the concentration of the microcystin compound in the sample.

2. The method of claim 1, wherein the quantitative analysis comprises HPLC-orbitrap-MS.

3. The method of claim 1, wherein the quantitative analysis comprises HPLC-QqQ-MS/MS.

4. The method of claim 1, wherein the purification step comprises: subjecting the sample to a solid-phase extraction SPE purification step,
   wherein the SPE purification step includes:
      equilibrating the conditioned SPE cartridge,
      loading samples into the equilibrated SPE cartridge, and
      eluting the sample;
   and,
   wherein the quantitative analysis comprises analyzing the eluted sample by HPLC-orbitrap-MS or HPLC-QqQ-MS/MS.

5. The method of claim 1, wherein, when the sample contains a microcystin compound in urine, the purifying further comprises eluting the sample with acetonitrile.

6. The method of claim 1, wherein the sample contains multiple microcystin compounds, and the liquid chromatography step separates the multiple microcystin compounds.

7. The method of claim 6, wherein the liquid chromatography step comprises gradient high-performance liquid chromatography.

8. The method of claim 1, wherein the microcystin compound is selected from the group consisting of MC-LR, MC-LA, MC-LF, MC-LW, MC-YR, and MC-RR, and combinations thereof.

9. A method for detecting and quantifying a microcystin compound in a sample, the method comprising:
   purifying a sample of plasma or serum containing a microcystin compound through a solid-phase extraction cartridge to obtain a purified sample;
   conducting a quantitative analysis on the purified sample to quantify the amount of the microcystin compound in the purified sample, wherein the quantitative analysis comprises a liquid chromatography step and a mass spectrometry step;
   using a calibration curve to determine the concentration of the microcystin compound in the sample; and
   when the sample contains a microcystin compound in plasma or serum, adding $ZnSO_4$ to the sample at a concentration of about 100 mM.

10. The method of claim 9, wherein the microcystin compound is selected from the group consisting of MC-LR, MC-LA, MC-LF, MC-LW, MC-YR, and MC-RR, and combinations thereof.

11. A method of preconcentrating mycrocystin in a sample, the method comprising:
   conditioning a solid-phase extraction (SPE) cartridge with methanol containing formic acid;
   loading a sample containing microcystin at a first concentration onto the solid-phase extraction cartridge;
   eluting the sample with methanol containing formic acid, and collecting the eluted sample; and,
   evaporating solvent from the eluted sample to obtain a preconcentrated sample,
   wherein the preconcentrated sample contains microcystin at a second concentration, the second concentration being greater than the first concentration.

12. The method of claim 11, wherein the SPE cartridge is a C18 cartridge.

13. The method of claim 11, wherein the sample comprises a plurality of microcystin species.

14. The method of claim 13, wherein the plurality of microcystin species includes two or more of MC-LR, MC-LA, MC-LF, MC-LW, MC-YR, and MC-RR.

15. The method of claim 11, wherein microcystin is selected from the group consisting of MC-LR, MC-LA, MC-LF, MC-LW, MC-YR, and MC-RR, and combinations thereof.

16. A method of preconcentrating mycrocystin in a sample, the method comprising:
   i) conditioning a solid-phase extraction (SPE) cartridge with methanol containing formic acid;
   ii) loading a sample containing microcystin at a first concentration onto the solid-phase extraction cartridge;
   iii) eluting the sample with methanol containing formic acid, and collecting the eluted sample;
   iv) evaporating solvent from the eluted sample to obtain a preconcentrated sample, wherein the preconcentrated sample contains microcystin at a second concentration, the second concentration being greater than the first concentration; and,
   v) subjecting the preconcentrated sample to LC-MS analysis.

17. The method of claim 16, wherein microcystin is selected from the group consisting of MC-LR, MC-LA, MC-LF, MC-LW, MC-YR, and MC-RR, and combinations thereof.

* * * * *